US011901041B2

(12) United States Patent
Samuels et al.

(10) Patent No.: US 11,901,041 B2
(45) Date of Patent: Feb. 13, 2024

(54) DIGITAL ANALYSIS OF NUCLEIC ACID MODIFICATION

(71) Applicant: Bio-Rad Laboratories, Inc., Hercules, CA (US)

(72) Inventors: Michael Samuels, Windham, NH (US); Jeffrey Olson, Chelmsford, MA (US); Darren R. Link, Lexington, MA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 489 days.

(21) Appl. No.: 14/505,974

(22) Filed: Oct. 3, 2014

(65) Prior Publication Data
US 2015/0099266 A1    Apr. 9, 2015

Related U.S. Application Data

(60) Provisional application No. 61/887,103, filed on Oct. 4, 2013.

(51) Int. Cl.
   *C12P 19/34*    (2006.01)
   *G16B 20/10*    (2019.01)
   *G16B 20/00*    (2019.01)

(52) U.S. Cl.
   CPC ............. *G16B 20/10* (2019.02); *G16B 20/00* (2019.02)

(58) Field of Classification Search
   USPC ......... 435/6.1, 6.11, 91.1, 183; 436/94, 501; 536/23.1, 24.3
   See application file for complete search history.

(56) References Cited

U.S. PATENT DOCUMENTS

| | | | |
|---|---|---|---|
| 2,097,692 | A | 11/1937 | Fiegel |
| 2,164,172 | A | 6/1939 | Dalton |
| 2,636,855 | A | 4/1953 | Schwartz |
| 2,656,508 | A | 10/1953 | Coulter |
| 2,692,800 | A | 10/1954 | Nichols et al. |
| 2,797,149 | A | 6/1957 | Skeggs |
| 2,879,141 | A | 3/1959 | Skeggs |
| 2,971,700 | A | 2/1961 | Peeps |

(Continued)

FOREIGN PATENT DOCUMENTS

| | | |
|---|---|---|
| AT | 140025 T | 7/1996 |
| AT | 140880 T | 8/1996 |

(Continued)

OTHER PUBLICATIONS

"Trisomy" from Wikipedia. Printed on Dec. 9, 2020.*

(Continued)

*Primary Examiner* — Frank W Lu
(74) *Attorney, Agent, or Firm* — Withers Bergman LLP; Thomas C. Meyers

(57) ABSTRACT

In certain aspects, methods of the invention involve performing modification state specific enzymatic reaction of nucleic acid in a sample, determining a value associated with efficiency of the modification state specific enzymatic reaction based on a control, determining an amount of target nucleic acid in the sample, and normalizing the amount of target nucleic acid based on the efficiency value. Based on the normalized amount of target nucleic acid, the method further includes determining whether the normalized amount of target nucleic acid is indicative of a condition.

8 Claims, 6 Drawing Sheets

(56) References Cited

U.S. PATENT DOCUMENTS

| | | |
|---|---|---|
| 3,479,141 A | 11/1969 | Smythe et al. |
| 3,608,821 A | 9/1971 | Simm et al. |
| 3,621,059 A | 11/1971 | Bartlett |
| 3,698,635 A | 10/1972 | Sickles |
| 3,784,471 A | 1/1974 | Kaiser |
| 3,816,331 A | 6/1974 | Brown, Jr. et al. |
| 3,828,085 A | 8/1974 | Price et al. |
| 3,930,061 A | 12/1975 | Scharfenberger |
| 3,960,187 A | 6/1976 | Stock et al. |
| 3,980,541 A | 9/1976 | Aine |
| 3,982,541 A | 9/1976 | L'Esperance, Jr. |
| 4,014,469 A | 3/1977 | Sato |
| 4,022,575 A | 5/1977 | Hansen et al. |
| 4,034,966 A | 7/1977 | Suh et al. |
| 4,059,552 A | 11/1977 | Zweigle et al. |
| 4,091,042 A | 5/1978 | Alexanderson et al. |
| 4,117,550 A | 9/1978 | Folland et al. |
| 4,130,394 A | 12/1978 | Negersmith |
| 4,210,809 A | 7/1980 | Pelavin |
| 4,253,846 A | 3/1981 | Smythe et al. |
| 4,266,721 A | 5/1981 | Sickles |
| 4,279,345 A | 7/1981 | Allred |
| 4,297,345 A | 10/1981 | Howarth |
| 4,315,754 A | 2/1982 | Ruzicka et al. |
| 4,378,957 A | 4/1983 | Malkin et al. |
| 4,383,767 A | 5/1983 | Jido |
| 4,439,980 A | 4/1984 | Biblarz et al. |
| 4,508,265 A | 4/1985 | Jido |
| 4,533,634 A | 8/1985 | Maldonado et al. |
| 4,585,209 A | 4/1986 | Aine et al. |
| 4,618,476 A | 10/1986 | Columbus |
| 4,675,285 A | 6/1987 | Clark et al. |
| 4,676,274 A | 6/1987 | Brown |
| 4,683,195 A | 7/1987 | Mullis et al. |
| 4,683,202 A | 7/1987 | Mullis |
| 4,739,044 A | 4/1988 | Stabinsky |
| 4,757,141 A | 7/1988 | Fung et al. |
| 4,767,515 A | 8/1988 | Scott et al. |
| 4,767,929 A | 8/1988 | Valentine |
| 4,779,805 A | 10/1988 | Jackson et al. |
| 4,795,330 A | 1/1989 | Noakes et al. |
| 4,801,086 A | 1/1989 | Noakes |
| 4,801,529 A | 1/1989 | Perlman |
| 4,829,996 A | 5/1989 | Noakes et al. |
| 4,853,336 A | 8/1989 | Saros et al. |
| 4,856,363 A | 8/1989 | LaRocca et al. |
| 4,859,363 A | 8/1989 | Davis et al. |
| 4,865,444 A | 9/1989 | Green et al. |
| 4,883,750 A | 11/1989 | Whiteley et al. |
| 4,908,112 A | 3/1990 | Pace |
| 4,931,225 A | 6/1990 | Cheng |
| 4,941,959 A | 7/1990 | Scott |
| 4,962,885 A | 10/1990 | Coffee |
| 4,963,498 A | 10/1990 | Hillman et al. |
| 4,981,580 A | 1/1991 | Auer |
| 4,996,004 A | 2/1991 | Bucheler et al. |
| 5,055,390 A | 10/1991 | Weaver et al. |
| 5,091,652 A | 2/1992 | Mathies et al. |
| 5,096,615 A | 3/1992 | Prescott et al. |
| 5,104,813 A | 4/1992 | Besemer et al. |
| 5,122,360 A | 6/1992 | Harris et al. |
| 5,149,625 A | 9/1992 | Church et al. |
| 5,180,662 A | 1/1993 | Sitkovsky |
| 5,185,099 A | 2/1993 | Delpuech et al. |
| 5,188,290 A | 2/1993 | Gebauer et al. |
| 5,188,291 A | 2/1993 | Cross |
| 5,192,659 A | 3/1993 | Simons |
| 5,204,112 A | 4/1993 | Hope et al. |
| 5,207,973 A | 5/1993 | Harris et al. |
| 5,241,159 A | 8/1993 | Chatteriee et al. |
| 5,260,466 A | 11/1993 | McGibbon |
| 5,262,027 A | 11/1993 | Scott |
| 5,270,163 A | 12/1993 | Gold et al. |
| 5,296,375 A | 3/1994 | Kricka et al. |
| 5,304,487 A | 4/1994 | Wilding et al. |
| 5,310,653 A | 5/1994 | Hanausek-Walaszek et al. |
| 5,313,009 A | 5/1994 | Guenkel et al. |
| 5,333,675 A | 8/1994 | Mullis et al. |
| 5,344,594 A | 9/1994 | Sheridon |
| 5,354,670 A | 10/1994 | Nickoloff et al. |
| 5,376,252 A | 12/1994 | Ekstrom et al. |
| 5,378,957 A | 1/1995 | Kelly |
| 5,397,605 A | 3/1995 | Barbieri et al. |
| 5,399,461 A | 3/1995 | Van et al. |
| 5,399,491 A | 3/1995 | Kacian et al. |
| 5,403,617 A | 4/1995 | Haaland |
| 5,413,924 A | 5/1995 | Kosak et al. |
| 5,417,235 A | 5/1995 | Wise et al. |
| 5,427,946 A | 6/1995 | Kricka et al. |
| 5,445,934 A | 8/1995 | Fodor et al. |
| 5,452,878 A | 9/1995 | Gravesen et al. |
| 5,452,955 A | 9/1995 | Lundstrom |
| 5,454,472 A | 10/1995 | Benecke et al. |
| 5,460,945 A | 10/1995 | Springer et al. |
| 5,468,613 A | 11/1995 | Erlich et al. |
| 5,475,096 A | 12/1995 | Gold et al. |
| 5,475,610 A | 12/1995 | Atwood et al. |
| 5,480,614 A | 1/1996 | Kamahori |
| 5,486,335 A | 1/1996 | Wilding et al. |
| 5,498,392 A | 3/1996 | Wilding et al. |
| 5,498,523 A | 3/1996 | Tabor et al. |
| 5,500,415 A | 3/1996 | Dollat et al. |
| 5,503,851 A | 4/1996 | Mank et al. |
| 5,512,131 A | 4/1996 | Kumar et al. |
| 5,516,635 A | 5/1996 | Ekins et al. |
| 5,518,709 A | 5/1996 | Sutton et al. |
| 5,523,162 A | 6/1996 | Franz et al. |
| 5,587,128 A | 12/1996 | Wilding et al. |
| 5,589,136 A | 12/1996 | Northrup et al. |
| 5,602,756 A | 2/1997 | Atwood et al. |
| 5,604,097 A | 2/1997 | Brenner |
| 5,610,016 A | 3/1997 | Sato et al. |
| 5,612,188 A | 3/1997 | Shuler et al. |
| 5,616,478 A | 4/1997 | Chetverin et al. |
| 5,617,997 A | 4/1997 | Kobayashi et al. |
| 5,635,358 A | 6/1997 | Wilding et al. |
| 5,636,400 A | 6/1997 | Young |
| 5,641,658 A | 6/1997 | Adams et al. |
| 5,643,729 A | 7/1997 | Taniguchi et al. |
| 5,655,517 A | 8/1997 | Coffee |
| 5,656,155 A | 8/1997 | Norcross et al. |
| 5,656,493 A | 8/1997 | Mullis et al. |
| 5,661,222 A | 8/1997 | Hare |
| 5,662,874 A | 9/1997 | David |
| 5,670,325 A | 9/1997 | Lapidus et al. |
| 5,681,600 A | 10/1997 | Antinone et al. |
| 5,695,934 A | 12/1997 | Brenner |
| 5,726,026 A | 3/1998 | Wilding et al. |
| 5,726,404 A | 3/1998 | Brody |
| 5,733,526 A | 3/1998 | Trevino et al. |
| 5,739,036 A | 4/1998 | Parris |
| 5,744,366 A | 4/1998 | Kricka et al. |
| 5,750,988 A | 5/1998 | Apffel et al. |
| 5,762,775 A | 6/1998 | DePaoli |
| 5,779,868 A | 7/1998 | Parce et al. |
| 5,783,431 A | 7/1998 | Peterson et al. |
| 5,789,206 A | 8/1998 | Tavtigian et al. |
| 5,813,988 A | 9/1998 | Alfano et al. |
| 5,840,506 A | 11/1998 | Giordano |
| 5,846,719 A | 12/1998 | Brenner et al. |
| 5,849,491 A | 12/1998 | Radomski et al. |
| 5,851,769 A | 12/1998 | Gray et al. |
| 5,858,187 A | 1/1999 | Ramsey et al. |
| 5,858,655 A | 1/1999 | Arnold |
| 5,858,670 A | 1/1999 | Lam et al. |
| 5,863,722 A | 1/1999 | Brenner |
| 5,868,322 A | 2/1999 | Loucks |
| 5,872,010 A | 2/1999 | Karger et al. |
| 5,876,771 A | 3/1999 | Sizer et al. |
| 5,880,071 A | 3/1999 | Parce et al. |
| 5,882,680 A | 3/1999 | Suzuki et al. |
| 5,882,856 A | 3/1999 | Shuber |
| 5,884,846 A | 3/1999 | Tan |
| 5,887,755 A | 3/1999 | Hood, III |

(56) References Cited

U.S. PATENT DOCUMENTS

| | | |
|---|---|---|
| 5,888,746 A | 3/1999 | Tabiti et al. |
| 5,888,778 A | 3/1999 | Shuber |
| 5,904,933 A | 5/1999 | Riess et al. |
| 5,921,678 A | 7/1999 | Desai et al. |
| 5,927,852 A | 7/1999 | Serafin |
| 5,928,870 A | 7/1999 | Lapidus et al. |
| 5,932,100 A | 8/1999 | Yager et al. |
| 5,935,331 A | 8/1999 | Naka et al. |
| 5,942,056 A | 8/1999 | Singh |
| 5,942,443 A | 8/1999 | Parce et al. |
| 5,958,203 A | 9/1999 | Parce et al. |
| 5,972,187 A | 10/1999 | Parce et al. |
| 5,980,936 A | 11/1999 | Krafft et al. |
| 5,989,815 A | 11/1999 | Skolnick et al. |
| 5,989,892 A | 11/1999 | Nishimaki et al. |
| 5,995,341 A | 11/1999 | Tanaka et al. |
| 5,997,636 A | 12/1999 | Gamarnik et al. |
| 6,008,003 A | 12/1999 | Haak-Frendscho et al. |
| 6,023,540 A | 2/2000 | Walt et al. |
| 6,028,066 A | 2/2000 | Unger |
| 6,042,709 A | 3/2000 | Parce et al. |
| 6,045,755 A | 4/2000 | Lebl et al. |
| 6,046,056 A | 4/2000 | Parce et al. |
| 6,048,551 A | 4/2000 | Hilfinger et al. |
| 6,048,690 A | 4/2000 | Heller et al. |
| 6,068,199 A | 5/2000 | Coffee |
| 6,074,879 A | 6/2000 | Zelmanovic et al. |
| 6,080,295 A | 6/2000 | Parce et al. |
| 6,081,612 A | 6/2000 | Gutkowicz-Krusin et al. |
| 6,086,740 A | 7/2000 | Kennedy |
| 6,096,495 A | 8/2000 | Kasai et al. |
| 6,103,537 A | 8/2000 | Ullman et al. |
| 6,105,571 A | 8/2000 | Coffee |
| 6,105,877 A | 8/2000 | Coffee |
| 6,107,059 A | 8/2000 | Hart |
| 6,116,516 A | 9/2000 | Ganan-Calvo |
| 6,118,849 A | 9/2000 | Tanimori et al. |
| 6,119,953 A | 9/2000 | Ganan-Calvo et al. |
| 6,120,666 A | 9/2000 | Jacobson et al. |
| 6,124,388 A | 9/2000 | Takai et al. |
| 6,124,439 A | 9/2000 | Friedman et al. |
| 6,130,052 A | 10/2000 | Van Baren et al. |
| 6,130,098 A | 10/2000 | Handique et al. |
| 6,137,214 A | 10/2000 | Raina |
| 6,138,077 A | 10/2000 | Brenner |
| 6,139,303 A | 10/2000 | Reed et al. |
| 6,140,053 A | 10/2000 | Koster |
| 6,143,496 A | 11/2000 | Brown et al. |
| 6,146,828 A | 11/2000 | Lapidus et al. |
| 6,149,789 A | 11/2000 | Benecke et al. |
| 6,150,180 A | 11/2000 | Parce et al. |
| 6,150,516 A | 11/2000 | Brenner et al. |
| 6,155,710 A | 12/2000 | Nakajima et al. |
| 6,162,421 A | 12/2000 | Ordino et al. |
| 6,165,778 A | 12/2000 | Kedar |
| 6,171,796 B1 | 1/2001 | An et al. |
| 6,171,850 B1 | 1/2001 | Nagle et al. |
| 6,172,214 B1 | 1/2001 | Brenner |
| 6,172,218 B1 | 1/2001 | Brenner |
| 6,174,160 B1 | 1/2001 | Lee et al. |
| 6,174,469 B1 | 1/2001 | Gañan-Calvo |
| 6,177,479 B1 | 1/2001 | Nakajima |
| 6,180,372 B1 | 1/2001 | Franzen |
| 6,184,012 B1 | 2/2001 | Neri et al. |
| 6,187,214 B1 | 2/2001 | Ganan-Calvo |
| 6,189,803 B1 | 2/2001 | Ganan-Calvo |
| 6,196,525 B1 | 3/2001 | Ganan-Calvo |
| 6,197,335 B1 | 3/2001 | Sherman |
| 6,197,835 B1 | 3/2001 | Ganan-Calvo |
| 6,203,993 B1 | 3/2001 | Shuber et al. |
| 6,207,372 B1 | 3/2001 | Shuber |
| 6,207,397 B1 | 3/2001 | Lynch et al. |
| 6,208,749 B1 | 3/2001 | Gutkowicz-Krusin et al. |
| 6,210,396 B1 | 4/2001 | MacDonald et al. |
| 6,210,891 B1 | 4/2001 | Nyren et al. |
| 6,210,896 B1 | 4/2001 | Chan |
| 6,214,558 B1 | 4/2001 | Shuber et al. |
| 6,221,654 B1 | 4/2001 | Quake et al. |
| 6,227,466 B1 | 5/2001 | Hartman et al. |
| 6,234,402 B1 | 5/2001 | Ganan-Calvo |
| 6,235,383 B1 | 5/2001 | Hong et al. |
| 6,235,475 B1 | 5/2001 | Brenner et al. |
| 6,241,159 B1 | 6/2001 | Ganan-Calvo et al. |
| 6,243,373 B1 | 6/2001 | Turock |
| 6,248,378 B1 | 6/2001 | Ganan-Calvo |
| 6,251,661 B1 | 6/2001 | Urabe et al. |
| 6,252,129 B1 | 6/2001 | Coffee |
| 6,258,568 B1 | 7/2001 | Nyren |
| 6,258,858 B1 | 7/2001 | Nakajima et al. |
| 6,261,661 B1 | 7/2001 | Ohno et al. |
| 6,261,797 B1 | 7/2001 | Sorge et al. |
| 6,263,222 B1 | 7/2001 | Diab et al. |
| 6,266,459 B1 | 7/2001 | Walt et al. |
| 6,267,353 B1 | 7/2001 | Friedline et al. |
| 6,267,858 B1 | 7/2001 | Parce et al. |
| 6,268,152 B1 | 7/2001 | Fodor et al. |
| 6,268,165 B1 | 7/2001 | O'Brien |
| 6,268,222 B1 | 7/2001 | Chandler et al. |
| 6,274,320 B1 | 8/2001 | Rothberg et al. |
| 6,274,337 B1 | 8/2001 | Parce et al. |
| 6,280,948 B1 | 8/2001 | Guilfoyle et al. |
| 6,292,756 B1 | 9/2001 | Lievois et al. |
| 6,294,344 B1 | 9/2001 | O'Brien |
| 6,296,020 B1 | 10/2001 | McNeely et al. |
| 6,296,673 B1 | 10/2001 | Santarsiero et al. |
| 6,299,145 B1 | 10/2001 | Ganan-Calvo |
| 6,301,055 B1 | 10/2001 | Legrand et al. |
| 6,306,659 B1 | 10/2001 | Parce et al. |
| 6,307,957 B1 | 10/2001 | Gutkowicz-Krusin et al. |
| 6,309,842 B1 | 10/2001 | Dower et al. |
| 6,310,354 B1 | 10/2001 | Hanninen et al. |
| 6,310,653 B1 | 10/2001 | Malcolm, Jr. et al. |
| 6,316,208 B1 | 11/2001 | Roberts et al. |
| 6,316,213 B1 | 11/2001 | O'Brien |
| 6,318,640 B1 | 11/2001 | Coffee |
| 6,324,417 B1 | 11/2001 | Cotton |
| 6,326,145 B1 | 12/2001 | Whitcombe et al. |
| 6,336,463 B1 | 1/2002 | Ohta |
| 6,344,325 B1 | 2/2002 | Quake et al. |
| 6,352,828 B1 | 3/2002 | Brenner |
| 6,355,193 B1 | 3/2002 | Stott |
| 6,355,198 B1 | 3/2002 | Kim et al. |
| 6,357,670 B2 | 3/2002 | Ganan-Calvo |
| 6,386,463 B1 | 5/2002 | Ganan-Calvo |
| 6,391,559 B1 | 5/2002 | Brown et al. |
| 6,394,429 B2 | 5/2002 | Ganan-Calvo |
| 6,399,339 B1 | 6/2002 | Wolberg et al. |
| 6,399,389 B1 | 6/2002 | Parce et al. |
| 6,403,373 B1 | 6/2002 | Scanlan et al. |
| 6,405,936 B1 | 6/2002 | Ganan-Calvo |
| 6,408,878 B2 | 6/2002 | Unger et al. |
| 6,409,832 B2 | 6/2002 | Weigl et al. |
| 6,429,025 B1 | 8/2002 | Parce et al. |
| 6,429,148 B1 | 8/2002 | Chu et al. |
| 6,432,143 B2 | 8/2002 | Kubiak et al. |
| 6,432,148 B1 | 8/2002 | Ganan-Calvo |
| 6,432,630 B1 | 8/2002 | Blankenstein |
| 6,439,103 B1 | 8/2002 | Miller |
| 6,440,706 B1 | 8/2002 | Vogelstein et al. |
| 6,440,760 B1 | 8/2002 | Cho et al. |
| 6,450,139 B1 | 9/2002 | Watanabe |
| 6,450,189 B1 | 9/2002 | Ganan-Calvo |
| 6,454,193 B1 | 9/2002 | Busick et al. |
| 6,464,336 B1 | 10/2002 | Sharma |
| 6,464,886 B2 | 10/2002 | Ganan-Calvo |
| 6,475,441 B1 | 11/2002 | Parce et al. |
| 6,481,648 B1 | 11/2002 | Zimmermann |
| 6,489,103 B1 | 12/2002 | Griffiths et al. |
| 6,503,933 B1 | 1/2003 | Moloney et al. |
| 6,506,609 B1 | 1/2003 | Wada et al. |
| 6,508,988 B1 | 1/2003 | Van Dam et al. |
| 6,511,803 B1 | 1/2003 | Church et al. |
| 6,520,425 B1 | 2/2003 | Reneker |
| 6,524,456 B1 | 2/2003 | Ramsey et al. |

(56) References Cited

U.S. PATENT DOCUMENTS

| | | |
|---|---|---|
| 6,540,395 B2 | 4/2003 | Muhlbauer et al. |
| 6,540,895 B1 | 4/2003 | Spence et al. |
| 6,551,836 B1 | 4/2003 | Chow et al. |
| 6,553,944 B1 | 4/2003 | Allen et al. |
| 6,553,960 B1 | 4/2003 | Yoshikawa et al. |
| 6,554,202 B2 | 4/2003 | Ganan-Calvo |
| 6,557,334 B2 | 5/2003 | Jager |
| 6,557,834 B2 | 5/2003 | Ganan-Calvo |
| 6,558,944 B1 | 5/2003 | Parce et al. |
| 6,558,960 B1 | 5/2003 | Parce et al. |
| 6,560,030 B2 | 5/2003 | Egrand et al. |
| 6,565,010 B2 | 5/2003 | Anderson et al. |
| 6,569,631 B1 | 5/2003 | Pantoliano et al. |
| 6,576,420 B1 | 6/2003 | Carson et al. |
| 6,591,852 B1 | 7/2003 | McNeely et al. |
| 6,592,321 B2 | 7/2003 | Bonker et al. |
| 6,592,821 B1 | 7/2003 | Wada et al. |
| 6,601,613 B2 | 8/2003 | McNeely et al. |
| 6,608,726 B2 | 8/2003 | Legrand et al. |
| 6,610,499 B1 | 8/2003 | Fulwyler et al. |
| 6,614,598 B1 | 9/2003 | Quake et al. |
| 6,627,603 B1 | 9/2003 | Bibette et al. |
| 6,630,006 B2 | 10/2003 | Santarsiero et al. |
| 6,630,353 B1 | 10/2003 | Parce et al. |
| 6,632,619 B1 | 10/2003 | Harrison et al. |
| 6,637,463 B1 | 10/2003 | Lei et al. |
| 6,638,749 B1 | 10/2003 | Beckman et al. |
| 6,645,432 B1 | 11/2003 | Anderson et al. |
| 6,646,253 B1 | 11/2003 | Rohwer et al. |
| 6,653,626 B2 | 11/2003 | Fischer et al. |
| 6,656,267 B2 | 12/2003 | Newman |
| 6,659,370 B1 | 12/2003 | Inoue |
| 6,660,252 B2 | 12/2003 | Matathia et al. |
| 6,670,142 B2 | 12/2003 | Lau et al. |
| 6,679,441 B1 | 1/2004 | Borra et al. |
| 6,680,178 B2 | 1/2004 | Harris et al. |
| 6,682,890 B2 | 1/2004 | Mack et al. |
| 6,717,136 B2 | 4/2004 | Andersson et al. |
| 6,729,561 B2 | 5/2004 | Hirae et al. |
| 6,738,502 B1 | 5/2004 | Coleman et al. |
| 6,739,036 B2 | 5/2004 | Koike et al. |
| 6,744,046 B2 | 6/2004 | Valaskovic et al. |
| 6,752,922 B2 | 6/2004 | Huang et al. |
| 6,753,147 B2 | 6/2004 | Vogelstein et al. |
| 6,766,817 B2 | 7/2004 | da Silva |
| 6,767,194 B2 | 7/2004 | Jeon et al. |
| 6,767,704 B2 | 7/2004 | Waldman et al. |
| 6,790,328 B2 | 9/2004 | Jacobson et al. |
| 6,793,753 B2 | 9/2004 | Unger et al. |
| 6,797,056 B2 | 9/2004 | David |
| 6,800,849 B2 | 10/2004 | Staats |
| 6,806,058 B2 | 10/2004 | Jesperson et al. |
| 6,808,382 B2 | 10/2004 | Lanfranchi |
| 6,808,882 B2 | 10/2004 | Griffiths et al. |
| 6,814,980 B2 | 11/2004 | Levy et al. |
| 6,818,395 B1 | 11/2004 | Quake et al. |
| 6,832,787 B1 | 12/2004 | Renzi |
| 6,833,242 B2 | 12/2004 | Quake et al. |
| 6,841,350 B2 | 1/2005 | Ogden et al. |
| 6,872,250 B2 | 3/2005 | David et al. |
| 6,890,487 B1 | 5/2005 | Sklar et al. |
| 6,897,018 B1 | 5/2005 | Yuan et al. |
| 6,905,844 B2 | 6/2005 | Kim |
| 6,918,404 B2 | 7/2005 | Dias da Silva |
| 6,926,313 B1 | 8/2005 | Renzi |
| 6,935,768 B2 | 8/2005 | Lowe et al. |
| 6,936,417 B2 | 8/2005 | Orntoft |
| 6,942,978 B1 | 9/2005 | O'Brien |
| 6,949,342 B2 | 9/2005 | Golub et al. |
| 6,960,437 B2 | 11/2005 | Enzelberger et al. |
| 6,964,847 B1 | 11/2005 | Englert |
| 6,974,667 B2 | 12/2005 | Horne et al. |
| 6,998,232 B1 | 2/2006 | Feinstein et al. |
| 7,022,472 B2 | 4/2006 | Robbins et al. |
| 7,041,481 B2 | 5/2006 | Anderson et al. |
| 7,049,072 B2 | 5/2006 | Seshi |
| 7,056,674 B2 | 6/2006 | Baker et al. |
| 7,057,026 B2 | 6/2006 | Barnes et al. |
| 7,066,586 B2 | 6/2006 | da Silva |
| 7,068,874 B2 | 6/2006 | Wang et al. |
| 7,078,180 B2 | 7/2006 | Genetta |
| 7,081,192 B1 | 7/2006 | Wang et al. |
| 7,081,340 B2 | 7/2006 | Baker et al. |
| 7,090,983 B1 | 8/2006 | Muramatsu et al. |
| 7,115,230 B2 | 10/2006 | Sundararajan |
| 7,118,910 B2 | 10/2006 | Unger et al. |
| 7,129,091 B2 | 10/2006 | Ismagilov et al. |
| 7,138,233 B2 | 11/2006 | Griffiths et al. |
| 7,153,700 B1 | 12/2006 | Pardee et al. |
| 7,156,917 B2 | 1/2007 | Moriyama et al. |
| 7,163,801 B2 | 1/2007 | Reed |
| 7,169,560 B2 | 1/2007 | Lapidus et al. |
| 7,171,311 B2 | 1/2007 | Dai et al. |
| 7,198,899 B2 | 4/2007 | Schleyer et al. |
| 7,204,431 B2 | 4/2007 | Li et al. |
| 7,229,770 B1 | 6/2007 | Price et al. |
| 7,252,943 B2 | 8/2007 | Griffiths et al. |
| 7,267,938 B2 | 9/2007 | Anderson et al. |
| 7,268,167 B2 | 9/2007 | Higuchi et al. |
| 7,282,337 B1 | 10/2007 | Harris |
| 7,291,462 B2 | 11/2007 | O'Brien et al. |
| 7,294,503 B2 | 11/2007 | Quake et al. |
| 7,300,765 B2 | 11/2007 | Patel |
| 7,308,364 B2 | 12/2007 | Shaughnessy et al. |
| 7,314,721 B2 | 1/2008 | Gure et al. |
| 7,316,906 B2 | 1/2008 | Chiorazzi et al. |
| 7,323,305 B2 | 1/2008 | Leamon et al. |
| 7,323,309 B2 | 1/2008 | Mirkin et al. |
| 7,326,529 B2 | 2/2008 | Ali et al. |
| 7,332,280 B2 | 2/2008 | Levy et al. |
| 7,332,590 B2 | 2/2008 | Nacht et al. |
| 7,341,211 B2 | 3/2008 | Ganan Calvo et al. |
| 7,348,142 B2 | 3/2008 | Wang |
| 7,358,231 B1 | 4/2008 | McCaffey et al. |
| 7,361,474 B2 | 4/2008 | Siegler |
| 7,364,862 B2 | 4/2008 | Ali et al. |
| 7,368,255 B2 | 5/2008 | Bae et al. |
| 7,378,233 B2 | 5/2008 | Sidransky et al. |
| 7,378,280 B2 | 5/2008 | Quake et al. |
| 7,390,463 B2 | 6/2008 | He et al. |
| 7,393,634 B1 | 7/2008 | Ahuja et al. |
| 7,393,665 B2 | 7/2008 | Brenner |
| 7,416,851 B2 | 8/2008 | Davi et al. |
| 7,429,467 B2 | 9/2008 | Holliger et al. |
| 7,432,064 B2 | 10/2008 | Salceda et al. |
| 7,442,507 B2 | 10/2008 | Polsky et al. |
| 7,449,303 B2 | 11/2008 | Coignet |
| 7,468,271 B2 | 12/2008 | Golovchenko et al. |
| 7,473,530 B2 | 1/2009 | Huttemann |
| 7,473,531 B1 | 1/2009 | Domon et al. |
| 7,476,506 B2 | 1/2009 | Schleyer et al. |
| 7,479,370 B2 | 1/2009 | Coignet |
| 7,479,371 B2 | 1/2009 | Ando et al. |
| 7,479,376 B2 | 1/2009 | Waldman et al. |
| 7,482,129 B2 | 1/2009 | Soyupak et al. |
| 7,501,244 B2 | 3/2009 | Reinhard et al. |
| 7,504,214 B2 | 3/2009 | Erlander et al. |
| 7,507,532 B2 | 3/2009 | Chang et al. |
| 7,507,541 B2 | 3/2009 | Raitano et al. |
| 7,510,707 B2 | 3/2009 | Platica et al. |
| 7,510,842 B2 | 3/2009 | Podust et al. |
| 7,514,209 B2 | 4/2009 | Dai et al. |
| 7,514,210 B2 | 4/2009 | Holliger et al. |
| 7,524,633 B2 | 4/2009 | Sidransky |
| 7,527,933 B2 | 5/2009 | Sahin et al. |
| 7,537,897 B2 | 5/2009 | Brenner et al. |
| 7,541,383 B2 | 6/2009 | Fu et al. |
| 7,544,473 B2 | 6/2009 | Brenner |
| 7,556,776 B2 | 7/2009 | Fraden et al. |
| 7,582,446 B2 | 9/2009 | Griffiths et al. |
| 7,595,195 B2 | 9/2009 | Lee et al. |
| 7,604,938 B2 | 10/2009 | Takahashi et al. |
| 7,622,081 B2 | 11/2009 | Chou et al. |
| 7,632,562 B2 | 12/2009 | Nair et al. |

(56) References Cited

U.S. PATENT DOCUMENTS

| | | |
|---|---|---|
| 7,635,562 B2 | 12/2009 | Harris et al. |
| 7,638,276 B2 | 12/2009 | Griffiths et al. |
| 7,655,435 B2 | 2/2010 | Holliger et al. |
| 7,655,470 B2 | 2/2010 | Ismagilov et al. |
| 7,666,593 B2 | 2/2010 | Lapidus |
| 7,691,576 B2 | 4/2010 | Holliger et al. |
| 7,698,287 B2 | 4/2010 | Becker et al. |
| 7,708,949 B2 | 5/2010 | Stone et al. |
| 7,718,578 B2 | 5/2010 | Griffiths et al. |
| 7,736,890 B2 | 6/2010 | Sia et al. |
| 7,741,130 B2 | 6/2010 | Lee, Jr. et al. |
| 7,754,428 B2 | 7/2010 | Lo et al. |
| RE41,780 E | 9/2010 | Anderson et al. |
| 7,814,175 B1 | 10/2010 | Chang et al. |
| 7,824,889 B2 | 11/2010 | Vogelstein et al. |
| 7,888,017 B2 | 2/2011 | Quake et al. |
| 7,897,044 B2 | 3/2011 | Hoyos et al. |
| 7,897,341 B2 | 3/2011 | Griffiths et al. |
| 7,901,939 B2 | 3/2011 | Ismagliov et al. |
| 7,915,015 B2 | 3/2011 | Vogelstein et al. |
| 7,968,287 B2 | 6/2011 | Griffiths et al. |
| 7,990,525 B2 | 8/2011 | Kanda |
| 8,012,382 B2 | 9/2011 | Kim et al. |
| 8,067,159 B2 | 11/2011 | Brown et al. |
| 8,153,402 B2 | 4/2012 | Holliger et al. |
| 8,252,539 B2 | 8/2012 | Quake et al. |
| 8,257,925 B2 | 9/2012 | Brown et al. |
| 8,278,071 B2 | 10/2012 | Brown et al. |
| 8,278,711 B2 | 10/2012 | Rao et al. |
| 8,288,100 B2 | 10/2012 | Lo et al. |
| 8,318,434 B2 | 11/2012 | Cuppens |
| 8,337,778 B2 | 12/2012 | Stone et al. |
| 8,436,993 B2 | 5/2013 | Kaduchak et al. |
| 8,462,269 B2 | 6/2013 | Cheng et al. |
| 8,528,589 B2 | 9/2013 | Miller et al. |
| 8,535,889 B2 | 9/2013 | Larson et al. |
| 8,592,221 B2 | 11/2013 | Fraden et al. |
| 8,673,595 B2 | 3/2014 | Nakamura et al. |
| 8,715,934 B2 | 5/2014 | Diehl et al. |
| 8,722,334 B2 | 5/2014 | Lo et al. |
| 8,765,485 B2 | 7/2014 | Link et al. |
| 8,772,046 B2 | 7/2014 | Fraden et al. |
| 8,841,071 B2 | 9/2014 | Link |
| 8,857,462 B2 | 10/2014 | Miller et al. |
| 8,871,444 B2 | 10/2014 | Griffiths et al. |
| 9,029,083 B2 | 5/2015 | Griffiths et al. |
| 9,029,085 B2 | 5/2015 | Agresti et al. |
| 9,176,031 B2 | 11/2015 | Watson |
| 9,186,643 B2 | 11/2015 | Griffiths et al. |
| 9,273,308 B2 | 3/2016 | Link et al. |
| 9,273,349 B2 | 3/2016 | Nguyen et al. |
| 9,328,344 B2 | 5/2016 | Link et al. |
| 9,364,803 B2 | 6/2016 | Yurkovetsky et al. |
| 9,399,797 B2 | 7/2016 | Hutchison et al. |
| 9,410,151 B2 | 8/2016 | Link et al. |
| 9,448,172 B2 | 9/2016 | Griffiths et al. |
| 9,816,121 B2 | 11/2017 | Agresti et al. |
| 9,839,890 B2 | 12/2017 | Griffiths et al. |
| 9,857,202 B2 | 1/2018 | Seki |
| 9,919,277 B2 | 3/2018 | Griffiths et al. |
| 9,925,501 B2 | 3/2018 | Griffiths et al. |
| 9,944,977 B2 | 4/2018 | Link et al. |
| 10,144,950 B2 | 12/2018 | Nolan |
| 10,151,698 B2 | 12/2018 | Griffiths et al. |
| 10,357,772 B2 | 7/2019 | Fraden et al. |
| 10,526,605 B2 | 1/2020 | Liu et al. |
| 10,584,332 B2 | 3/2020 | Samuels et al. |
| 10,596,541 B2 | 3/2020 | Weitz et al. |
| 10,612,081 B2 | 4/2020 | Hutchison et al. |
| 10,633,652 B2 | 4/2020 | Link et al. |
| 10,639,597 B2 | 5/2020 | Link et al. |
| 10,639,598 B2 | 5/2020 | Griffiths et al. |
| 10,675,626 B2 | 6/2020 | Fraden et al. |
| 2001/0010338 A1 | 8/2001 | Ganan-Calvo |
| 2001/0020011 A1 | 9/2001 | Mathiowitz et al. |
| 2001/0023078 A1 | 9/2001 | Bawendi et al. |
| 2001/0029983 A1 | 10/2001 | Unger et al. |
| 2001/0032053 A1 | 10/2001 | Hielscher et al. |
| 2001/0034025 A1 | 10/2001 | Modlin et al. |
| 2001/0034031 A1 | 10/2001 | Short et al. |
| 2001/0041343 A1 | 11/2001 | Pankowsky |
| 2001/0041344 A1 | 11/2001 | Sepetov et al. |
| 2001/0041357 A1 | 11/2001 | Fouillet et al. |
| 2001/0042793 A1 | 11/2001 | Ganan-Calvo |
| 2001/0048900 A1 | 12/2001 | Bardell et al. |
| 2001/0050881 A1 | 12/2001 | Depaoli et al. |
| 2002/0004532 A1 | 1/2002 | Matathia et al. |
| 2002/0005354 A1 | 1/2002 | Spence et al. |
| 2002/0008028 A1 | 1/2002 | Jacobson et al. |
| 2002/0012971 A1 | 1/2002 | Mehta |
| 2002/0015997 A1 | 2/2002 | Lafferty |
| 2002/0022038 A1 | 2/2002 | Biatry et al. |
| 2002/0022261 A1 | 2/2002 | Anderson et al. |
| 2002/0033422 A1 | 3/2002 | Ganan-Calvo |
| 2002/0034737 A1 | 3/2002 | Drmanac |
| 2002/0036018 A1 | 3/2002 | McNeely et al. |
| 2002/0036139 A1 | 3/2002 | Becker et al. |
| 2002/0041378 A1 | 4/2002 | Peltie et al. |
| 2002/0058332 A1 | 5/2002 | Quake et al. |
| 2002/0065609 A1 | 5/2002 | Ashby |
| 2002/0067800 A1 | 6/2002 | Newman et al. |
| 2002/0084417 A1 | 7/2002 | Khalil et al. |
| 2002/0085961 A1 | 7/2002 | Morin et al. |
| 2002/0090720 A1 | 7/2002 | Mutz et al. |
| 2002/0106667 A1 | 8/2002 | Yamamoto et al. |
| 2002/0119455 A1 | 8/2002 | Chan |
| 2002/0119459 A1 | 8/2002 | Griffiths |
| 2002/0127591 A1 | 9/2002 | Wada et al. |
| 2002/0142344 A1 | 10/2002 | Akeson et al. |
| 2002/0143437 A1 | 10/2002 | Handique et al. |
| 2002/0155080 A1 | 10/2002 | Glenn et al. |
| 2002/0158027 A1 | 10/2002 | Moon et al. |
| 2002/0164271 A1 | 11/2002 | Ho |
| 2002/0164629 A1 | 11/2002 | Quake et al. |
| 2002/0166582 A1 | 11/2002 | O'Connor et al. |
| 2002/0179849 A1 | 12/2002 | Maher et al. |
| 2003/0008308 A1 | 1/2003 | Enzelberger et al. |
| 2003/0012586 A1 | 1/2003 | Iwata et al. |
| 2003/0015425 A1 | 1/2003 | Bohm et al. |
| 2003/0017305 A1 | 1/2003 | Roitman et al. |
| 2003/0017579 A1 | 1/2003 | Corn et al. |
| 2003/0039169 A1 | 2/2003 | Ehrfeld et al. |
| 2003/0040620 A1 | 2/2003 | Langmore et al. |
| 2003/0059764 A1 | 3/2003 | Ravkin et al. |
| 2003/0061687 A1 | 4/2003 | Hansen et al. |
| 2003/0064414 A1 | 4/2003 | Benecky et al. |
| 2003/0082795 A1 | 5/2003 | Shuler et al. |
| 2003/0083276 A1 | 5/2003 | Li et al. |
| 2003/0104372 A1 | 6/2003 | Ahmadian et al. |
| 2003/0108900 A1 | 6/2003 | Oliphant et al. |
| 2003/0124586 A1 | 7/2003 | Griffiths et al. |
| 2003/0143599 A1 | 7/2003 | Makarov et al. |
| 2003/0144260 A1 | 7/2003 | Gilon |
| 2003/0148273 A1 | 8/2003 | Dong et al. |
| 2003/0148544 A1 | 8/2003 | Nie et al. |
| 2003/0181574 A1 | 9/2003 | Adam et al. |
| 2003/0183525 A1 | 10/2003 | Elrod et al. |
| 2003/0207295 A1 | 11/2003 | Gunderson et al. |
| 2003/0219754 A1 | 11/2003 | Oleksy et al. |
| 2003/0224509 A1 | 12/2003 | Moon et al. |
| 2003/0229376 A1 | 12/2003 | Sandhu |
| 2003/0230486 A1 | 12/2003 | Chien et al. |
| 2003/0232356 A1 | 12/2003 | Dooley et al. |
| 2004/0005582 A1 | 1/2004 | Shipwash |
| 2004/0005594 A1 | 1/2004 | Holliger et al. |
| 2004/0018525 A1 | 1/2004 | Wirtz et al. |
| 2004/0027915 A1 | 2/2004 | Lowe et al. |
| 2004/0030255 A1 | 2/2004 | Alfano et al. |
| 2004/0031688 A1 | 2/2004 | Shenderov |
| 2004/0037739 A1 | 2/2004 | McNeely et al. |
| 2004/0037813 A1 | 2/2004 | Simpson et al. |
| 2004/0041093 A1 | 3/2004 | Schultz et al. |
| 2004/0050946 A1 | 3/2004 | Wang et al. |
| 2004/0053247 A1 | 3/2004 | Cordon-Cardo et al. |

(56) References Cited

U.S. PATENT DOCUMENTS

| | | |
|---|---|---|
| 2004/0057906 A1 | 3/2004 | Hsu et al. |
| 2004/0058450 A1 | 3/2004 | Pamula et al. |
| 2004/0068019 A1 | 4/2004 | Higuchi et al. |
| 2004/0071781 A1 | 4/2004 | Chattopadhyay et al. |
| 2004/0079881 A1 | 4/2004 | Fischer et al. |
| 2004/0086892 A1 | 5/2004 | Crothers et al. |
| 2004/0091923 A1 | 5/2004 | Reyes et al. |
| 2004/0092824 A1 | 5/2004 | Stamnes et al. |
| 2004/0096515 A1 | 5/2004 | Bausch et al. |
| 2004/0134854 A1 | 7/2004 | Higuchi et al. |
| 2004/0136497 A1 | 7/2004 | Meldrum et al. |
| 2004/0142329 A1 | 7/2004 | Erikson et al. |
| 2004/0146866 A1 | 7/2004 | Fu |
| 2004/0146921 A1 | 7/2004 | Veleigh et al. |
| 2004/0159633 A1 | 8/2004 | Whitesides et al. |
| 2004/0180346 A1 | 9/2004 | Anderson et al. |
| 2004/0181131 A1 | 9/2004 | Maynard et al. |
| 2004/0181343 A1 | 9/2004 | Wigstrom et al. |
| 2004/0182712 A1 | 9/2004 | Basol |
| 2004/0185484 A1 | 9/2004 | Costa et al. |
| 2004/0188254 A1 | 9/2004 | Spaid |
| 2004/0209299 A1 | 10/2004 | Pinter et al. |
| 2004/0224325 A1 | 11/2004 | Knapp et al. |
| 2004/0224419 A1 | 11/2004 | Zheng et al. |
| 2004/0229349 A1 | 11/2004 | Daridon |
| 2004/0241693 A1 | 12/2004 | Ricoul et al. |
| 2004/0253731 A1 | 12/2004 | Holliger et al. |
| 2004/0258203 A1 | 12/2004 | Yamano et al. |
| 2004/0259083 A1 | 12/2004 | Oshima |
| 2005/0000970 A1 | 1/2005 | Kimbara et al. |
| 2005/0003380 A1 | 1/2005 | Cohen et al. |
| 2005/0008592 A1 | 1/2005 | Gardel et al. |
| 2005/0019776 A1 | 1/2005 | Callow et al. |
| 2005/0032238 A1 | 2/2005 | Karp et al. |
| 2005/0032240 A1 | 2/2005 | Lee et al. |
| 2005/0037392 A1 | 2/2005 | Griffiths et al. |
| 2005/0037397 A1 | 2/2005 | Mirkin et al. |
| 2005/0042639 A1 | 2/2005 | Knapp et al. |
| 2005/0042648 A1 | 2/2005 | Griffiths et al. |
| 2005/0048467 A1 | 3/2005 | Sastry et al. |
| 2005/0064460 A1 | 3/2005 | Holliger et al. |
| 2005/0069920 A1 | 3/2005 | Griffiths et al. |
| 2005/0079501 A1 | 4/2005 | Koike et al. |
| 2005/0079510 A1 | 4/2005 | Berka et al. |
| 2005/0084923 A1 | 4/2005 | Mueller et al. |
| 2005/0087122 A1 | 4/2005 | Ismagliov et al. |
| 2005/0095611 A1 | 5/2005 | Chan et al. |
| 2005/0100895 A1 | 5/2005 | Waldman et al. |
| 2005/0103690 A1 | 5/2005 | Kawano et al. |
| 2005/0123937 A1 | 6/2005 | Thorp et al. |
| 2005/0129582 A1 | 6/2005 | Breidford et al. |
| 2005/0130173 A1 | 6/2005 | Leamon et al. |
| 2005/0152908 A1 | 7/2005 | Liew et al. |
| 2005/0161669 A1 | 7/2005 | Jovanovich et al. |
| 2005/0164239 A1 | 7/2005 | Griffiths et al. |
| 2005/0169797 A1 | 8/2005 | Oshima |
| 2005/0170373 A1 | 8/2005 | Monforte |
| 2005/0170431 A1 | 8/2005 | Ibrahim et al. |
| 2005/0172476 A1 | 8/2005 | Stone et al. |
| 2005/0183995 A1 | 8/2005 | Deshpande et al. |
| 2005/0202429 A1 | 9/2005 | Trau et al. |
| 2005/0202489 A1 | 9/2005 | Cho et al. |
| 2005/0207940 A1 | 9/2005 | Butler et al. |
| 2005/0208495 A1 | 9/2005 | Joseph et al. |
| 2005/0214173 A1 | 9/2005 | Facer et al. |
| 2005/0221339 A1 | 10/2005 | Griffiths et al. |
| 2005/0221341 A1 | 10/2005 | Shimkets et al. |
| 2005/0226742 A1 | 10/2005 | Unger et al. |
| 2005/0227264 A1 | 10/2005 | Nobile et al. |
| 2005/0248066 A1 | 11/2005 | Esteban |
| 2005/0251049 A1 | 11/2005 | Cane et al. |
| 2005/0260566 A1 | 11/2005 | Fischer et al. |
| 2005/0272159 A1 | 12/2005 | Ismagilov et al. |
| 2005/0287572 A1 | 12/2005 | Mathies et al. |
| 2006/0003347 A1 | 1/2006 | Griffiths et al. |
| 2006/0003429 A1 | 1/2006 | Frost et al. |
| 2006/0003439 A1 | 1/2006 | Ismagilov et al. |
| 2006/0008824 A1 | 1/2006 | Ronaghi et al. |
| 2006/0035386 A1 | 2/2006 | Hattori et al. |
| 2006/0036348 A1 | 2/2006 | Handique et al. |
| 2006/0040197 A1 | 2/2006 | Kabai |
| 2006/0040297 A1 | 2/2006 | Leamon et al. |
| 2006/0046257 A1 | 3/2006 | Pollock et al. |
| 2006/0051329 A1 | 3/2006 | Lee et al. |
| 2006/0068398 A1 | 3/2006 | McMillan |
| 2006/0078475 A1 | 4/2006 | Tai et al. |
| 2006/0078888 A1 | 4/2006 | Griffiths et al. |
| 2006/0078893 A1 | 4/2006 | Griffiths et al. |
| 2006/0094119 A1 | 5/2006 | Ismagilov et al. |
| 2006/0100788 A1 | 5/2006 | Carrino et al. |
| 2006/0108012 A1 | 5/2006 | Barrow et al. |
| 2006/0110759 A1 | 5/2006 | Paris et al. |
| 2006/0115821 A1 | 6/2006 | Einstein et al. |
| 2006/0147909 A1 | 7/2006 | Rarbach et al. |
| 2006/0153924 A1 | 7/2006 | Griffiths et al. |
| 2006/0154298 A1 | 7/2006 | Griffiths et al. |
| 2006/0160762 A1 | 7/2006 | Zetter et al. |
| 2006/0163385 A1 | 7/2006 | Link et al. |
| 2006/0169800 A1 | 8/2006 | Rosell et al. |
| 2006/0177832 A1 | 8/2006 | Brenner |
| 2006/0195269 A1 | 8/2006 | Yeatman et al. |
| 2006/0223127 A1 | 10/2006 | Yip et al. |
| 2006/0234254 A1 | 10/2006 | An et al. |
| 2006/0234259 A1 | 10/2006 | Rubin et al. |
| 2006/0234264 A1 | 10/2006 | Hardenbol |
| 2006/0246431 A1 | 11/2006 | Balachandran |
| 2006/0247532 A1 | 11/2006 | Ramanujam et al. |
| 2006/0252057 A1 | 11/2006 | Raponi et al. |
| 2006/0257893 A1 | 11/2006 | Takahashi et al. |
| 2006/0258841 A1 | 11/2006 | Michl et al. |
| 2006/0263888 A1 | 11/2006 | Fritz et al. |
| 2006/0269558 A1 | 11/2006 | Murphy et al. |
| 2006/0269934 A1 | 11/2006 | Woudenberg et al. |
| 2006/0269971 A1 | 11/2006 | Diamandis |
| 2006/0281089 A1 | 12/2006 | Gibson et al. |
| 2006/0281098 A1 | 12/2006 | Miao et al. |
| 2006/0286570 A1 | 12/2006 | Rowlen et al. |
| 2007/0003442 A1 | 1/2007 | Link et al. |
| 2007/0009914 A1 | 1/2007 | Wallace et al. |
| 2007/0009954 A1 | 1/2007 | Wang et al. |
| 2007/0016078 A1 | 1/2007 | Hoyt et al. |
| 2007/0020617 A1 | 1/2007 | Trnovsky et al. |
| 2007/0026439 A1 | 2/2007 | Faulstich et al. |
| 2007/0031829 A1 | 2/2007 | Yasuno et al. |
| 2007/0042400 A1 | 2/2007 | Choi et al. |
| 2007/0042419 A1 | 2/2007 | Barany et al. |
| 2007/0045117 A1 | 3/2007 | Pamula et al. |
| 2007/0048744 A1 | 3/2007 | Lapidus |
| 2007/0053896 A1 | 3/2007 | Ahmed et al. |
| 2007/0054119 A1 | 3/2007 | Garstecki et al. |
| 2007/0056853 A1 | 3/2007 | Aizenberg et al. |
| 2007/0065823 A1 | 3/2007 | Dressman et al. |
| 2007/0077572 A1 | 4/2007 | Tawfik et al. |
| 2007/0077579 A1 | 4/2007 | Griffiths et al. |
| 2007/0092914 A1 | 4/2007 | Griffiths et al. |
| 2007/0111303 A1 | 5/2007 | Inoue et al. |
| 2007/0120899 A1 | 5/2007 | Ohnishi et al. |
| 2007/0123430 A1 | 5/2007 | Pasquier et al. |
| 2007/0141593 A1 | 6/2007 | Lee et al. |
| 2007/0142720 A1 | 6/2007 | Ridder et al. |
| 2007/0154889 A1 | 7/2007 | Wang |
| 2007/0156037 A1 | 7/2007 | Pilon et al. |
| 2007/0166705 A1 | 7/2007 | Milton et al. |
| 2007/0172873 A1 | 7/2007 | Brenner et al. |
| 2007/0184439 A1 | 8/2007 | Guilford et al. |
| 2007/0184489 A1 | 8/2007 | Griffiths et al. |
| 2007/0195127 A1 | 8/2007 | Ahn et al. |
| 2007/0202525 A1 | 8/2007 | Quake et al. |
| 2007/0213410 A1 | 9/2007 | Hastwell et al. |
| 2007/0241068 A1 | 10/2007 | Pamula et al. |
| 2007/0242105 A1 | 10/2007 | Srinivasan et al. |
| 2007/0243634 A1 | 10/2007 | Pamula et al. |
| 2007/0259351 A1 | 11/2007 | Chinitz et al. |
| 2007/0259368 A1 | 11/2007 | An et al. |

(56) References Cited

U.S. PATENT DOCUMENTS

| | | |
|---|---|---|
| 2007/0259374 A1 | 11/2007 | Griffiths et al. |
| 2007/0269804 A1 | 11/2007 | Liew et al. |
| 2007/0275415 A1 | 11/2007 | Srinivasan et al. |
| 2007/0292869 A1 | 12/2007 | Becker et al. |
| 2008/0003142 A1 | 1/2008 | Link et al. |
| 2008/0003571 A1 | 1/2008 | McKeman et al. |
| 2008/0004436 A1 | 1/2008 | Tawfik et al. |
| 2008/0009005 A1 | 1/2008 | Kruk |
| 2008/0014589 A1 | 1/2008 | Link et al. |
| 2008/0014590 A1 | 1/2008 | Dahary et al. |
| 2008/0020940 A1 | 1/2008 | Stedronsky et al. |
| 2008/0021330 A1 | 1/2008 | Hwang et al. |
| 2008/0023330 A1 | 1/2008 | Viovy et al. |
| 2008/0032413 A1 | 2/2008 | Kim et al. |
| 2008/0038754 A1 | 2/2008 | Farias-Eisner et al. |
| 2008/0044828 A1 | 2/2008 | Kwok |
| 2008/0050378 A1 | 2/2008 | Nakamura et al. |
| 2008/0050723 A1 | 2/2008 | Belacel et al. |
| 2008/0053205 A1 | 3/2008 | Pollack et al. |
| 2008/0057514 A1 | 3/2008 | Goldenring |
| 2008/0058432 A1 | 3/2008 | Wang et al. |
| 2008/0063227 A1 | 3/2008 | Rohrseitz |
| 2008/0064047 A1 | 3/2008 | Zetter et al. |
| 2008/0081330 A1 | 4/2008 | Kahvejian |
| 2008/0081333 A1 | 4/2008 | Mori et al. |
| 2008/0092973 A1 | 4/2008 | Lai |
| 2008/0113340 A1 | 5/2008 | Schlegel |
| 2008/0118462 A1 | 5/2008 | Alani et al. |
| 2008/0124726 A1 | 5/2008 | Monforte |
| 2008/0138806 A1 | 6/2008 | Chow et al. |
| 2008/0166772 A1 | 7/2008 | Hollinger et al. |
| 2008/0166793 A1 | 7/2008 | Beer et al. |
| 2008/0171078 A1 | 7/2008 | Gray |
| 2008/0176211 A1 | 7/2008 | Spence et al. |
| 2008/0176236 A1 | 7/2008 | Tsao et al. |
| 2008/0181850 A1 | 7/2008 | Thaxton et al. |
| 2008/0206756 A1 | 8/2008 | Lee et al. |
| 2008/0216563 A1 | 9/2008 | Reed et al. |
| 2008/0220986 A1 | 9/2008 | Gormley et al. |
| 2008/0222741 A1 | 9/2008 | Chinnaiyan |
| 2008/0234138 A1 | 9/2008 | Shaughnessy et al. |
| 2008/0234139 A1 | 9/2008 | Shaughnessy et al. |
| 2008/0241830 A1 | 10/2008 | Vogelstein et al. |
| 2008/0261295 A1 | 10/2008 | Butler et al. |
| 2008/0268473 A1 | 10/2008 | Moses et al. |
| 2008/0269157 A1 | 10/2008 | Srivastava et al. |
| 2008/0274513 A1 | 11/2008 | Shenderov et al. |
| 2008/0274908 A1 | 11/2008 | Chang |
| 2008/0280285 A1 | 11/2008 | Chen et al. |
| 2008/0280302 A1 | 11/2008 | Kebebew |
| 2008/0286199 A1 | 11/2008 | Livingston et al. |
| 2008/0286801 A1 | 11/2008 | Arjol et al. |
| 2008/0286811 A1 | 11/2008 | Moses et al. |
| 2008/0293578 A1 | 11/2008 | Shaugnessy et al. |
| 2008/0299565 A1 | 12/2008 | Schneider et al. |
| 2008/0305482 A1 | 12/2008 | Brentano et al. |
| 2008/0311570 A1 | 12/2008 | Lai |
| 2008/0311604 A1 | 12/2008 | Elting et al. |
| 2009/0004687 A1 | 1/2009 | Mansfield et al. |
| 2009/0005254 A1 | 1/2009 | Griffiths et al. |
| 2009/0009855 A1 | 1/2009 | Nakatsuka et al. |
| 2009/0012187 A1 | 1/2009 | Chu et al. |
| 2009/0017463 A1 | 1/2009 | Bhowmick |
| 2009/0021728 A1 | 1/2009 | Heinz et al. |
| 2009/0023137 A1 | 1/2009 | Van Der Zee et al. |
| 2009/0026082 A1 | 1/2009 | Rothberg et al. |
| 2009/0029372 A1 | 1/2009 | Wewer |
| 2009/0042737 A1 | 2/2009 | Katz et al. |
| 2009/0053700 A1 | 2/2009 | Griffiths et al. |
| 2009/0053732 A1 | 2/2009 | Vermesh et al. |
| 2009/0060797 A1 | 3/2009 | Mathies et al. |
| 2009/0062144 A1 | 3/2009 | Guo |
| 2009/0068170 A1 | 3/2009 | Weitz et al. |
| 2009/0069194 A1 | 3/2009 | Ramakrishnan |
| 2009/0075265 A1 | 3/2009 | Budiman et al. |
| 2009/0075307 A1 | 3/2009 | Fischer et al. |
| 2009/0075311 A1 | 3/2009 | Karl |
| 2009/0081237 A1 | 3/2009 | D'Andrea et al. |
| 2009/0081685 A1 | 3/2009 | Beyer et al. |
| 2009/0087849 A1 | 4/2009 | Malinowski et al. |
| 2009/0092973 A1 | 4/2009 | Erlander et al. |
| 2009/0098542 A1 | 4/2009 | Budiman et al. |
| 2009/0098543 A1 | 4/2009 | Budiman et al. |
| 2009/0098555 A1 | 4/2009 | Roth et al. |
| 2009/0105959 A1 | 4/2009 | Braverman et al. |
| 2009/0118128 A1 | 5/2009 | Liu et al. |
| 2009/0124569 A1 | 5/2009 | Bergan et al. |
| 2009/0127454 A1 | 5/2009 | Ritchie et al. |
| 2009/0127589 A1 | 5/2009 | Rothberg et al. |
| 2009/0131353 A1 | 5/2009 | Insel et al. |
| 2009/0131543 A1 | 5/2009 | Weitz et al. |
| 2009/0134027 A1 | 5/2009 | Jary |
| 2009/0134331 A1 | 5/2009 | Miyamae et al. |
| 2009/0191565 A1 | 7/2009 | Lapidus et al. |
| 2009/0197248 A1 | 8/2009 | Griffiths et al. |
| 2009/0197772 A1 | 8/2009 | Griffiths et al. |
| 2009/0215633 A1 | 8/2009 | Van Eijk et al. |
| 2009/0226971 A1 | 9/2009 | Beer et al. |
| 2009/0226972 A1 | 9/2009 | Beer et al. |
| 2009/0233802 A1 | 9/2009 | Bignell et al. |
| 2009/0246788 A1 | 10/2009 | Albert et al. |
| 2009/0317798 A1 | 12/2009 | Heid et al. |
| 2009/0325217 A1 | 12/2009 | Luscher |
| 2009/0325236 A1 | 12/2009 | Griffiths et al. |
| 2010/0003687 A1 | 1/2010 | Simen et al. |
| 2010/0009353 A1 | 1/2010 | Barnes et al. |
| 2010/0015617 A1 | 1/2010 | Toyama |
| 2010/0021984 A1 | 1/2010 | Edd et al. |
| 2010/0022414 A1 | 1/2010 | Link et al. |
| 2010/0035252 A1 | 2/2010 | Rothberg et al. |
| 2010/0055677 A1 | 3/2010 | Colston, Jr. et al. |
| 2010/0075436 A1 | 3/2010 | Urdea et al. |
| 2010/0105112 A1 | 4/2010 | Holtze et al. |
| 2010/0111768 A1 | 5/2010 | Banerjee et al. |
| 2010/0124759 A1 | 5/2010 | Wang et al. |
| 2010/0130369 A1 | 5/2010 | Shenderov et al. |
| 2010/0136544 A1 | 6/2010 | Agresti et al. |
| 2010/0137143 A1 | 6/2010 | Rothberg et al. |
| 2010/0137163 A1 | 6/2010 | Link et al. |
| 2010/0159592 A1 | 6/2010 | Holliger et al. |
| 2010/0172803 A1 | 7/2010 | Stone et al. |
| 2010/0173293 A1 | 7/2010 | Woudenberg et al. |
| 2010/0173394 A1 | 7/2010 | Colston, Jr. et al. |
| 2010/0188073 A1 | 7/2010 | Rothberg et al. |
| 2010/0197507 A1 | 8/2010 | Rothberg et al. |
| 2010/0210479 A1 | 8/2010 | Griffiths et al. |
| 2010/0213628 A1 | 8/2010 | Bausch et al. |
| 2010/0233026 A1 | 9/2010 | Ismagliov et al. |
| 2010/0240101 A1 | 9/2010 | Lieberman et al. |
| 2010/0273173 A1 | 10/2010 | Hirai et al. |
| 2010/0282617 A1 | 11/2010 | Rothberg et al. |
| 2010/0285975 A1 | 11/2010 | Mathies et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2011/0000560 A1 | 1/2011 | Miller et al. |
| 2011/0024455 A1 | 2/2011 | Bethuy et al. |
| 2011/0033854 A1 | 2/2011 | Drmanac et al. |
| 2011/0045462 A1 | 2/2011 | Fu et al. |
| 2011/0053151 A1 | 3/2011 | Hansen et al. |
| 2011/0053798 A1 | 3/2011 | Hindson et al. |
| 2011/0059435 A1 | 3/2011 | Vogelstein et al. |
| 2011/0059556 A1 | 3/2011 | Strey et al. |
| 2011/0104725 A1 | 5/2011 | Pamula et al. |
| 2011/0104816 A1 | 5/2011 | Pollack et al. |
| 2011/0111981 A1 | 5/2011 | Love et al. |
| 2011/0142734 A1 | 6/2011 | Ismagliov et al. |
| 2011/0151444 A1 | 6/2011 | Albers et al. |
| 2011/0159499 A1 | 6/2011 | Hindson et al. |
| 2011/0174622 A1 | 7/2011 | Ismagliov et al. |
| 2011/0176966 A1 | 7/2011 | Ismagliov et al. |
| 2011/0177494 A1 | 7/2011 | Ismagliov et al. |
| 2011/0177586 A1 | 7/2011 | Ismagliov et al. |

(56) References Cited

U.S. PATENT DOCUMENTS

| | | |
|---|---|---|
| 2011/0177609 A1 | 7/2011 | Ismagilov et al. |
| 2011/0188717 A1 | 8/2011 | Baudry et al. |
| 2011/0190146 A1 | 8/2011 | Boehm et al. |
| 2011/0218123 A1 | 9/2011 | Weitz et al. |
| 2011/0223314 A1 | 9/2011 | Zhang et al. |
| 2011/0244455 A1 | 10/2011 | Larson et al. |
| 2011/0250597 A1 | 10/2011 | Larson et al. |
| 2011/0257031 A1 | 10/2011 | Bodeau et al. |
| 2011/0267457 A1 | 11/2011 | Weitz et al. |
| 2011/0275063 A1 | 11/2011 | Weitz et al. |
| 2011/0311978 A1 | 12/2011 | Makarewicz, Jr. et al. |
| 2012/0010098 A1 | 1/2012 | Griffiths et al. |
| 2012/0010107 A1 | 1/2012 | Griffiths et al. |
| 2012/0014977 A1 | 1/2012 | Furihata et al. |
| 2012/0015382 A1 | 1/2012 | Weitz et al. |
| 2012/0015822 A1 | 1/2012 | Weitz et al. |
| 2012/0021919 A1 | 1/2012 | Scholl et al. |
| 2012/0021930 A1 | 1/2012 | Schoen et al. |
| 2012/0088691 A1 | 4/2012 | Chen et al. |
| 2012/0122714 A1 | 5/2012 | Samuels et al. |
| 2012/0164652 A1 | 6/2012 | Clemens et al. |
| 2012/0165219 A1 | 6/2012 | Van Der Zaag et al. |
| 2012/0167142 A1 | 6/2012 | Hey |
| 2012/0171667 A1 | 7/2012 | Shoemaker et al. |
| 2012/0190032 A1 | 7/2012 | Ness et al. |
| 2012/0220494 A1 | 8/2012 | Samuels et al. |
| 2012/0231972 A1 | 9/2012 | Golyshin et al. |
| 2012/0244043 A1 | 9/2012 | Leblanc et al. |
| 2012/0252012 A1 | 10/2012 | Armougom et al. |
| 2012/0253689 A1 | 10/2012 | Rogan |
| 2012/0258516 A1 | 10/2012 | Schultz et al. |
| 2012/0288857 A1 | 11/2012 | Livak |
| 2012/0302448 A1 | 11/2012 | Hutchison et al. |
| 2012/0322058 A1 | 12/2012 | Regan et al. |
| 2013/0099018 A1 | 4/2013 | Miller et al. |
| 2013/0109577 A1 | 5/2013 | Korlach et al. |
| 2013/0143745 A1 | 6/2013 | Christen et al. |
| 2013/0157870 A1 | 6/2013 | Pushkarev et al. |
| 2013/0157872 A1 | 6/2013 | Griffiths et al. |
| 2013/0178368 A1 | 7/2013 | Griffiths et al. |
| 2013/0178378 A1 | 7/2013 | Hatch et al. |
| 2013/0203606 A1 | 8/2013 | Pollack et al. |
| 2013/0217071 A1 | 8/2013 | Montesclaros et al. |
| 2013/0217601 A1 | 8/2013 | Griffiths et al. |
| 2013/0224751 A1 | 8/2013 | Olson et al. |
| 2013/0225418 A1 | 8/2013 | Watson |
| 2013/0225623 A1 | 8/2013 | Buxbaum et al. |
| 2013/0244906 A1 | 9/2013 | Collins |
| 2013/0274117 A1 | 10/2013 | Church et al. |
| 2013/0288254 A1 | 10/2013 | Pollack et al. |
| 2013/0295567 A1 | 11/2013 | Link et al. |
| 2013/0295568 A1 | 11/2013 | Link |
| 2013/0296535 A1 | 11/2013 | Church et al. |
| 2014/0065631 A1 | 3/2014 | Froehlich et al. |
| 2014/0256568 A1 | 9/2014 | Link |
| 2014/0256585 A1 | 9/2014 | McCoy |
| 2014/0274786 A1 | 9/2014 | McCoy et al. |
| 2014/0323317 A1 | 10/2014 | Link et al. |
| 2014/0329239 A1 | 11/2014 | Larson et al. |
| 2015/0018236 A1 | 1/2015 | Green et al. |
| 2015/0038356 A1 | 2/2015 | Karlin-Neumann et al. |
| 2015/0126400 A1 | 5/2015 | Watson et al. |
| 2015/0184256 A1 | 7/2015 | Samuels et al. |
| 2015/0197790 A1 | 7/2015 | Tzonev |
| 2015/0247191 A1 | 9/2015 | Zhang et al. |
| 2015/0336072 A1 | 11/2015 | Weitz et al. |
| 2016/0289670 A1 | 10/2016 | Samuels et al. |
| 2016/0304954 A1 | 10/2016 | Lin et al. |
| 2017/0304785 A1 | 10/2017 | Link et al. |
| 2018/0057863 A1 | 3/2018 | Larson et al. |
| 2018/0057868 A1 | 3/2018 | Walder et al. |
| 2018/0223348 A1 | 8/2018 | Link et al. |
| 2018/0272294 A1 | 9/2018 | Griffiths et al. |
| 2018/0272296 A1 | 9/2018 | Link et al. |
| 2018/0272299 A1 | 9/2018 | Griffiths et al. |
| 2018/0353913 A1 | 12/2018 | Link et al. |
| 2018/0355350 A1 | 12/2018 | Link et al. |
| 2018/0361346 A1 | 12/2018 | Griffiths et al. |
| 2018/0363050 A1 | 12/2018 | Hutchison et al. |
| 2019/0024261 A1 | 1/2019 | Griffiths et al. |
| 2019/0107489 A1 | 4/2019 | Griffiths et al. |
| 2019/0134581 A1 | 5/2019 | Yurkovetsky et al. |
| 2019/0316119 A1 | 10/2019 | Samuels et al. |

FOREIGN PATENT DOCUMENTS

| | | |
|---|---|---|
| AT | 155711 T | 8/1997 |
| AT | 167816 T | 7/1998 |
| AU | 4032078 A | 4/1980 |
| AU | 6415380 A | 5/1981 |
| AU | 1045983 A | 6/1984 |
| AU | 2177292 A | 1/1993 |
| AU | 4222393 A | 11/1993 |
| AU | 4222593 A | 11/1993 |
| AU | 4222693 A | 11/1993 |
| AU | 4222793 A | 11/1993 |
| AU | 4223593 A | 11/1993 |
| AU | 677197 B2 | 4/1997 |
| AU | 677781 B2 | 5/1997 |
| AU | 680195 B2 | 7/1997 |
| AU | 2935197 A | 1/1998 |
| AU | 3499097 A | 1/1998 |
| AU | 3501297 A | 1/1998 |
| AU | 1276099 A | 6/1999 |
| AU | 4955799 A | 12/1999 |
| AU | 3961100 A | 10/2000 |
| AU | 4910300 A | 11/2000 |
| AU | 747464 B2 | 5/2002 |
| AU | 768399 B2 | 12/2003 |
| AU | 2004225691 B2 | 6/2010 |
| AU | 2010224352 A1 | 10/2010 |
| BR | 8200642 A | 12/1982 |
| BR | 9710052 A | 1/2000 |
| CA | 1093344 A1 | 1/1981 |
| CA | 2258481 A1 | 1/1998 |
| CA | 2520548 A1 | 10/2004 |
| CH | 563 087 A5 | 6/1975 |
| CH | 563807 A5 | 7/1975 |
| DE | 2100685 A1 | 7/1972 |
| DE | 3042915 A1 | 9/1981 |
| DE | 43 08 839 C2 | 4/1997 |
| DE | 69126763 T2 | 2/1998 |
| DE | 199 61 257 A1 | 7/2001 |
| DE | 100 15 109 A1 | 10/2001 |
| DE | 100 41 823 A1 | 3/2002 |
| EP | 0047130 B1 | 2/1985 |
| EP | 0402995 A2 | 12/1990 |
| EP | 0249007 A3 | 3/1991 |
| EP | 0418635 A1 | 3/1991 |
| EP | 0476178 A1 | 3/1992 |
| EP | 0546174 A1 | 6/1993 |
| EP | 0618001 | 10/1994 |
| EP | 620432 A1 | 10/1994 |
| EP | 0637996 A1 | 2/1995 |
| EP | 0637997 A1 | 2/1995 |
| EP | 0718038 A2 | 6/1996 |
| EP | 0540281 B1 | 7/1996 |
| EP | 0528580 B1 | 12/1996 |
| EP | 0486351 B1 | 7/1997 |
| EP | 0895120 | 2/1999 |
| EP | 1362634 A1 | 11/2003 |
| EP | 1447127 A1 | 8/2004 |
| EP | 04782399.2 | 5/2006 |
| EP | 1741482 | 1/2007 |
| EP | 2017910 A1 | 1/2009 |
| EP | 2127736 | 12/2009 |
| EP | 2047910 B1 | 1/2012 |
| EP | 13165665.4 | 11/2013 |
| EP | 13165667.0 | 11/2013 |
| EP | 2363205 A3 | 6/2014 |
| EP | 2534267 B1 | 4/2018 |
| ES | 2 095 413 T3 | 2/1997 |
| FR | 2 404 834 A1 | 4/1979 |
| FR | 2 451 579 A1 | 10/1980 |

(56) References Cited

FOREIGN PATENT DOCUMENTS

| | | |
|---|---|---|
| FR | 2 469 714 A1 | 5/1981 |
| FR | 2 470 385 A1 | 5/1981 |
| FR | 2 650 657 A1 | 2/1991 |
| FR | 2 669 028 A1 | 5/1992 |
| FR | 2 703 263 A1 | 10/1994 |
| GB | 1148543 | 4/1969 |
| GB | 1 446 998 | 8/1976 |
| GB | 2 005 224 | 4/1979 |
| GB | 2 047 880 | 12/1980 |
| GB | 2 062 225 | 5/1981 |
| GB | 2 064 114 | 6/1981 |
| GB | 2097692 A | 11/1982 |
| GB | 2 210 532 | 6/1989 |
| IE | 922432 A1 | 2/1993 |
| JP | S5372016 A | 6/1978 |
| JP | S5455495 A | 5/1979 |
| JP | 55125472 | 9/1980 |
| JP | S5636053 A | 4/1981 |
| JP | 56-124052 | 9/1981 |
| JP | 59-49832 A | 3/1984 |
| JP | 59-102163 | 6/1984 |
| JP | H0665609 A | 3/1994 |
| JP | 6-265447 A | 9/1994 |
| JP | 7-489 A | 1/1995 |
| JP | 8-153669 | 6/1996 |
| JP | 10-217477 | 8/1998 |
| JP | 3-232525 | 10/1998 |
| JP | 2000-271475 | 10/2000 |
| JP | 2001-301154 A | 10/2001 |
| JP | 2001-517353 A | 10/2001 |
| JP | 2002-085961 A | 3/2002 |
| JP | 2003-501257 A | 1/2003 |
| JP | 2003-502656 A | 1/2003 |
| JP | 2003-149136 A | 5/2003 |
| JP | 2003-222633 A | 8/2003 |
| JP | 2005-037346 A | 2/2005 |
| JP | 2005-192944 A | 7/2005 |
| JP | 2007-190364 A | 8/2007 |
| JP | 2009-265751 A | 11/2009 |
| JP | 2010-198393 A | 9/2010 |
| JP | 2012-204765 A | 10/2012 |
| JP | 2013-143959 A | 7/2013 |
| JP | 2016063824 A | 4/2016 |
| NZ | 264353 A | 5/1996 |
| WO | 84/02000 | 5/1984 |
| WO | 90/15807 A1 | 12/1990 |
| WO | 91/05058 A1 | 4/1991 |
| WO | 91/07772 | 5/1991 |
| WO | 91/16966 A1 | 11/1991 |
| WO | 92/03734 | 3/1992 |
| WO | 92/21746 | 12/1992 |
| WO | 93/03151 | 2/1993 |
| WO | 93/08278 | 4/1993 |
| WO | 93/22053 | 11/1993 |
| WO | 93/22054 | 11/1993 |
| WO | 93/22055 | 11/1993 |
| WO | 93/22058 | 11/1993 |
| WO | 93/22421 | 11/1993 |
| WO | 94/16332 | 7/1994 |
| WO | 94/23738 | 10/1994 |
| WO | 94/24314 | 10/1994 |
| WO | 94/26766 | 11/1994 |
| WO | 98/00705 | 1/1995 |
| WO | 95/11922 | 5/1995 |
| WO | 95/19922 | 7/1995 |
| WO | 95/24929 | 9/1995 |
| WO | 95/33447 | 12/1995 |
| WO | 96/34112 | 10/1996 |
| WO | 96/38730 | 12/1996 |
| WO | 96/40057 A2 | 12/1996 |
| WO | 96/40062 | 12/1996 |
| WO | 96/40723 | 12/1996 |
| WO | 97/00125 | 1/1997 |
| WO | 97/00442 | 1/1997 |
| WO | 97/04297 | 2/1997 |
| WO | 97/04748 | 2/1997 |
| WO | 97/23140 | 7/1997 |
| WO | 97/28556 | 8/1997 |
| WO | 97/38318 A1 | 10/1997 |
| WO | 97/39814 | 10/1997 |
| WO | 97/40141 | 10/1997 |
| WO | 97/45644 | 12/1997 |
| WO | 97/47763 A1 | 12/1997 |
| WO | 98/00231 | 1/1998 |
| WO | 98/02237 | 1/1998 |
| WO | 98/10267 | 3/1998 |
| WO | 98/13502 | 4/1998 |
| WO | 98/22625 A1 | 5/1998 |
| WO | 98/23733 | 6/1998 |
| WO | 98/31700 | 7/1998 |
| WO | 98/33001 | 7/1998 |
| WO | 98/34120 | 8/1998 |
| WO | 98/37186 | 8/1998 |
| WO | 98/41869 | 9/1998 |
| WO | 98/52691 | 11/1998 |
| WO | 98/58085 | 12/1998 |
| WO | 99/02671 | 1/1999 |
| WO | 99/22858 | 5/1999 |
| WO | 99/28020 | 6/1999 |
| WO | 99/28507 A1 | 6/1999 |
| WO | 99/31019 | 6/1999 |
| WO | 99/42539 | 8/1999 |
| WO | 99/54730 | 10/1999 |
| WO | 99/61888 | 12/1999 |
| WO | 00/04139 A1 | 1/2000 |
| WO | 00/47322 | 2/2000 |
| WO | 00/52455 | 2/2000 |
| WO | 00/37924 A1 | 6/2000 |
| WO | 00/40712 | 6/2000 |
| WO | 00/54735 | 9/2000 |
| WO | 00/61275 | 10/2000 |
| WO | 00/70080 | 11/2000 |
| WO | 00/76673 | 12/2000 |
| WO | 00/078455 A1 | 12/2000 |
| WO | 01/12327 | 2/2001 |
| WO | 01/14589 | 3/2001 |
| WO | 01/18244 | 3/2001 |
| WO | 01/64332 | 9/2001 |
| WO | 01/68257 | 9/2001 |
| WO | 01/69289 | 9/2001 |
| WO | 01/72431 | 10/2001 |
| WO | 01/80283 | 10/2001 |
| WO | 01/089787 A2 | 11/2001 |
| WO | 01/89788 A2 | 11/2001 |
| WO | 01/94635 A2 | 12/2001 |
| WO | 02/16017 | 2/2002 |
| WO | 02/18949 | 3/2002 |
| WO | 02/22869 | 3/2002 |
| WO | 02/23163 | 3/2002 |
| WO | 02/27660 A2 | 4/2002 |
| WO | 02/31203 | 4/2002 |
| WO | 2002/036815 A2 | 5/2002 |
| WO | 02/47665 | 8/2002 |
| WO | 02/060275 | 8/2002 |
| WO | 02/060591 A1 | 8/2002 |
| WO | 02/066992 A1 | 8/2002 |
| WO | 02/068104 A1 | 9/2002 |
| WO | 02/078845 | 10/2002 |
| WO | 02/103011 | 12/2002 |
| WO | 02/103363 | 12/2002 |
| WO | 03/011443 | 2/2003 |
| WO | 03/026798 A1 | 4/2003 |
| WO | 03/037302 | 5/2003 |
| WO | 03/044187 | 5/2003 |
| WO | 03/078659 | 9/2003 |
| WO | 2003/003015 | 10/2003 |
| WO | 03/099843 | 12/2003 |
| WO | 2004/002627 | 1/2004 |
| WO | 2004/018497 A2 | 3/2004 |
| WO | 2004/024917 | 3/2004 |
| WO | 2004/026453 A2 | 4/2004 |
| WO | 2004/037374 A2 | 5/2004 |
| WO | 2004/038363 | 5/2004 |
| WO | 2004/069849 | 8/2004 |

(56) References Cited

FOREIGN PATENT DOCUMENTS

| | | |
|---|---|---|
| WO | 2004/071638 A2 | 8/2004 |
| WO | 2004/074504 | 9/2004 |
| WO | 2004/083443 | 9/2004 |
| WO | 2004/087308 | 10/2004 |
| WO | 2004/088314 | 10/2004 |
| WO | 2004/091763 | 10/2004 |
| WO | 2004/102204 | 11/2004 |
| WO | 2004/103565 | 12/2004 |
| WO | 2005/000970 | 1/2005 |
| WO | 2005/002730 | 1/2005 |
| WO | 2005/003375 A2 | 1/2005 |
| WO | 2005/11867 A2 | 2/2005 |
| WO | 2005/021151 | 3/2005 |
| WO | 2005/023427 A1 | 3/2005 |
| WO | 2005/041884 A2 | 5/2005 |
| WO | 2005/049787 A2 | 6/2005 |
| WO | 2005/103106 | 11/2005 |
| WO | 2005/118138 | 12/2005 |
| WO | 2005/118867 A2 | 12/2005 |
| WO | 2006/002641 | 1/2006 |
| WO | 2006/009657 | 1/2006 |
| WO | 2006/027757 | 3/2006 |
| WO | 2006/038035 | 4/2006 |
| WO | 2006/040551 | 4/2006 |
| WO | 2006/040554 | 4/2006 |
| WO | 2006/076810 A1 | 7/2006 |
| WO | 2006/078841 | 7/2006 |
| WO | 2006/096571 | 9/2006 |
| WO | 2006/101851 | 9/2006 |
| WO | 2007/012638 A1 | 2/2007 |
| WO | 2007/021343 | 2/2007 |
| WO | 2007/030501 | 3/2007 |
| WO | 2007026884 A1 | 3/2007 |
| WO | 2007/081385 | 7/2007 |
| WO | 2007/081387 | 7/2007 |
| WO | 2007/089541 | 8/2007 |
| WO | 2007/114794 A1 | 10/2007 |
| WO | 2007/123744 A2 | 11/2007 |
| WO | 2007/133710 | 11/2007 |
| WO | 2007/138178 | 12/2007 |
| WO | 2007/140015 A2 | 12/2007 |
| WO | 2008/021123 | 2/2008 |
| WO | 2008/063227 | 5/2008 |
| WO | 2008/097559 | 8/2008 |
| WO | 2008/115626 A2 | 9/2008 |
| WO | 2008/121342 | 10/2008 |
| WO | 2008/130623 | 10/2008 |
| WO | 2007/092473 | 11/2008 |
| WO | 2008/134153 A1 | 11/2008 |
| WO | 2009/015296 A1 | 1/2009 |
| WO | 2009/029229 | 3/2009 |
| WO | 2009/049889 A1 | 4/2009 |
| WO | 2009/059430 A1 | 5/2009 |
| WO | 2009/085929 A1 | 7/2009 |
| WO | 2009/094623 A2 | 7/2009 |
| WO | 2009/117485 A2 | 9/2009 |
| WO | 2009/137415 A2 | 11/2009 |
| WO | 2009/137606 A1 | 11/2009 |
| WO | 2010/009365 A1 | 1/2010 |
| WO | 2010/056728 A1 | 5/2010 |
| WO | 2010/040006 | 8/2010 |
| WO | 2010/115154 A1 | 10/2010 |
| WO | 2010/151776 | 12/2010 |
| WO | 2011/042564 | 4/2011 |
| WO | 2011/079176 | 6/2011 |
| WO | 2011/100604 A2 | 8/2011 |
| WO | 2012/022976 A1 | 2/2012 |
| WO | 2012/045012 A2 | 4/2012 |
| WO | 2012/047297 A2 | 4/2012 |
| WO | 2012/048341 A1 | 4/2012 |
| WO | 2012/083225 A2 | 6/2012 |
| WO | 2012/112970 A2 | 8/2012 |
| WO | 2012/142213 A2 | 10/2012 |
| WO | 2012/167142 A2 | 12/2012 |
| WO | 2013/14356 A2 | 1/2013 |
| WO | 2013/120089 A1 | 8/2013 |
| WO | 2013/165748 A1 | 11/2013 |
| WO | 2014/026031 A1 | 2/2014 |
| WO | 2014/065756 A1 | 5/2014 |
| WO | 2014/165559 A2 | 10/2014 |
| WO | 2014/204939 A2 | 12/2014 |
| WO | 2015/013681 A1 | 1/2015 |
| WO | 2015/200893 A2 | 12/2015 |
| WO | 2017/117358 A1 | 7/2017 |

OTHER PUBLICATIONS

"Digital polymerase chain reaction" from Wikipedia. Printed on Dec. 9, 2020.*
Poon et al., Differential DNA Methylation between Fetus and Mother as a Strategy for Detecting Fetal DNA in Maternal Plasma. Clinical Chemistry, 48, 35-41, 2002.*
Viswanathan et al., DNA Analysis by Restriction Enzyme (DARE) enables concurrent genomic and epigenomic characterization of single cells. Nucleic Acids Research, 47 (19), e122, 2019.*
Squires, 2005, Microfluidics: fluid physics at the nanoliter scale, Rev Mod Phys 77:977-1026.
Stauber, 1993, Rapid generation of monoclonal antibody-secreting hybridomas against African horse sickness virus by in vitro immunization and the fusion/cloning technique, J Immunol Meth 161(2):157-168.
Stemmer, 1994, DNA shuffling by random fragmentation and reassembly: in vitro recombination for molecular evolution. PNAS 91(22):10747-51.
Stemmer, 1994, Rapid evolution of a protein in vitro by DNA shuffling, Nature 370(6488):389-91.
Stober, 1998, Controlled growth of monodisperse silica spheres in the micron size range, J Colloid Interface Sci 26(1):62-69.
Stofko, 1992, A single step purification for recombinant proteins, Febs Lett 302:274-278.
Stone, 2004, Engineering flows in small devices: microfluidics toward a lab-on-a-chip, Ann Rev Fluid Mech 36:381-441.
Strizhkov, 2000, PCR amplification on a microarray of gel-immobilized oligonucleotides: Detection of bacterial toxin- and drug-resistant genes and their mutations, BioTechniques 29(4):844-857.
Strommenger, 2003, Multiplex PCR assay for simultaneous detection of nine clinicly relevant antibiotic resistance genes in S aureus, J Clin Microb 41(9):4089-4094.
Stroock, 2002, Chaotic mixer for microchannels, Science 295(5555):647-651.
Studer, 1997, Fluorous synthesis: a fluorous-phase strategy for improving separation efficiency in organic synthesis, Science 275:823-826.
Sugiura, 2001, Interfacial tension driven monodispersed droplet formation from mtcrofabricated channel array, Langmuir 17:5562-5566.
Sugiura, 2002, Effect of channel structure on microchannel emuisification, Langmuir 18:5708-5712.
Sundberg, 1995, Spatially-addressable immobilisation of macromolecules on solid supports, J Am Chem Soc 117:12050-12057.
Sung, 2005, Chip-based microfluidic devices coupled with electrospray ionization-mass spectrometry, Electrophoresis 26:1783-1791.
Sutcliffe, 1986, Dynamics of UV laser ablation of organic polymer surfaces, J Appl Phys 60(9):3315-3322.
Suzuki, 1996, Random mutagenesis of thermus aquaticus DNA polmerase I: concordance of immutable sites in vivo with the crystal structure, PNAS 93:96701-9675.
Suzuki, 2013, A novel guidewire approach for handling acute-angle bifurcations, J Inv Cardiol 25(1):48-54.
Syed, 2009, Next-generation sequencing library preparation: simultaneous fragmentation and tagging using in vitro transposition, Nat Meth 6:1-2.
Takayama, 1999, Patterning cells and their environmnets using multiple laminar fluid flows in cappillary networks, PNAS 96:5545-5548.
Takeuchi, 2005, An axisymmetric flow-focusing microfluidic device, Adv Mater 17(8):1067-1072.

(56) References Cited

OTHER PUBLICATIONS

Taly, 2007, Droplets as microreactors for high-throughput biology, Chembiochem 8(3):263-272.
Tan, 2003, Controlled fission of droplet emulsions in bifurcating microfluidic channels, 12th Int Conf SSAM 28-31.
Tan, 2003, Microfluidic liposome generation from monodisperse droplet emulsion, Summer Bioeng Conf, Florida, 2 pages.
Tan, 2003, Monodisperse droplet emulsions in co-flow microfluidic channels, Micro TAS, 2 pages.
Tan, 2004, Design of microluidic channel geometries for the control of droplet volume, chemical concentration, and sorting, Lab Chip 4(4):292-298.
Tang, 2009, A multi-color fast-switching microfluidic droplet dye laser, Lab Chip 9:2767-2771.
Taniguchi, 2002, Chemical reactions in microdroplets by electrostatic manipulation of droplets in liquid media, Lab Chip 2:19-23.
Tawfik, 1998, Man-made cell-like compartments for molecular evolution, Nat Biotech 7(16):652-56.
Taylor, 1934, The formation of emulsions in definable field of flow, Proc R Soc London A 146(858):501-523.
Taylor, 1991, Characterization of chemisorbed monolayers by surface potential measurments, J Phys D Appl Phys 24:1443.
Tencza, 2000, Development of a fluorescence polarization-based diagnostic assay for equine infectious anemia virus, J Clin Microbiol 38(5):1854-185.
Terray, 2002, Fabrication of linear colloidal structures for microfluidic applications, Applied Phys Lett 81(9):1555-1557.
Terray, 2002, Microfluidic control using colloidal devices, Science 296(5574):1841-1844.
Tewhey, 2009, Microdroplet based PCR environment for large scale targeted sequence, Nat Biotech 27(11):1025-1031.
Theberge, 2010, Microdroplets in microfluidics: an evolving platform for discoveries in chemistry and biology, Angew Chem Int Ed 49(34):5846-5868.
Thompson, 1983, Introduction to Lithography, ACS Symp Ser 219:1-13.
Thorsen, 2001, Dynamic pattern formation in a vesicle-generating microfluidic device, Phys Rev Lett 86(18):4163-4166.
Thorsen, 2002, Microfluidic large-scale integration, Science 298:580-584.
Thorsen, 2003, Microfluidic technologies for highthroughput screening applications, California Institute of Technology.
Tice, 2003, Formation of droplets and mixing in multiphase microfluidics at low values of the reynolds and the capillary numbers, Langmuir 19:9127-9133.
Tice, 2004, Effects of viscosity on droplet formation and mixing in microfluidic channels, Analytica Chimica Acta 507:73-77.
Titomanlio, 1990, Capillary experiments of flow induced crystallization of HDPE, AIChe J 36(1):13-18.
Tleugabulova, 2004, Evaluating formation and growth mechanisms of silica particles using fluorescence anisotropy decay analysis, Langmuir 20(14):5924-5932.
Tokatlidis, 1995, Nascent chains: folding and chaperone intraction during elongation on ribosomes, Philos Trans R Soc Lond B Biol Sci, 348:89-95.
Tokeshi, 2002, Continuous-flow chemical processing on a microchip by combining microunit operations and a multiphase flow network, Anal Chem 74(7):1565-1571.
Tokumitsu, 1999, Preparation of gadopentetic acid-loaded chitosan microparticles for gadolinium neutron-capture therapy of cancer by a novel emulsion-droplet coalescence technique, Chem Pharm Bull 47(6):838-842.
Tonelli et al., 2002, Perfluoropolyether functional oligomers: unusual reactivity in organic chemistry, Journal of fluorine Chemistry, 118; 107-121.
Trolier-McKinstry, 2004, Thin Film Piezoelectric for MEMS, Journal of Electroceramics 12:7-17.
Tsuchiya, 2007, On-chip polymerase chain reaction microdevice employing a magnetic droplet-manipulation system, Sens Actuators B 130:583-588.
Schatz, 1996, Screening of peptide libraries linked to lac repressor, Meth Enzymol 267:171-91.
Schneegass, 2001, Miniaturized flow-through PCR with different template types in a silicone chip thermocycler, Lab on a Chip 1:42-9.
Schopman, 2012, Selective packaging of cellular miRNAs in HIV-1 particles, Virus Res 169(2):438-47.
Schubert, 2002, Designer Capsules, Nat Med 8:1362.
Schweitzer, 2000, Immunoassays with rolling circle DNA amplification, PNAS 97(18):10113-10119.
Schweitzer, 2001, Combining nucleic acid amplification and detection. Curr Opin Biotechnol 12(1):21-7.
Scott, 1948, The solubility of fluorocarbons, J Am Chem Soc 70:4090-4093.
Sedlak, 2013, Viral diagnostics in the era of digital polymerase chain reaction, Diag Microb Inf Dis 75(1):1-4.
Seethala, 1997, Homogeneous fluorescence polarization assay for Src-Family tyrosine kinases, Anal Biochem 253(2):210-218.
Seiler, 1993, Planar glass chips for capillary electrophoresis: repetitive sample injection, quantitation, and separation efficiency, Anal Chem 65(10):1481-1488.
Selwyn, 1965, A simple test for inactivation of an enzyme during assay, Biochim Biophys Acta 105:193-195.
Sen, 2012, Development and validation of a new adenosine-independent index of stenosis severity from coronary wave-intensity analysis, Journal of the American College of Cardiology 59(15):1392-1402.
Seo, 2007, Microfluidic consecutive flow-focusing droplet generators, Soft Matter 3:986-992.
Seong, 2002, Efficient mixing and reactions within microfluidic channels using microbead-supported catalysts, J Am Chem Soc 124(45):13360-1.
Seong, 2002, Fabrication of microchambers defined by photopolymerized hydrogels and weirs within microfluidic systems, Anal Chem 74(14):3372-3377.
Sepp, 2002, Microbead display by in vitro compartmentalisation: selection for binding using flow cytometry, FEBS Letters 532:455-58.
Serpersu, 1985, Reversible and irreversible modification of erythrocyte membrane permeability by electric field, Biochim Biophys Acta 812(3):779-785.
Shapiro, 1983, Multistation multiparameter flow cytometry: a critical review and rationale, Cytometry 3: 227-243.
Shastry, 2006, Directing droplets using microstructured surfaces, Langmuir 22:6161-6167.
Shen, 2006, Eigengene-based linear discriminant model for tumor classification using gene expression microarray data, Bioinformatics 22(21):2635-2642.
Shestopalov, 2004, Multi-step synthesis of nanoparticles performed on millisecond time scale in a microfluidic droplet-based system, Royal Soc Chem 4:316-321.
Shim, 2007, Using microfluidics to decouple nucleation and growth of protein crystals, Cryst Growth Des 7(11):2192-2194.
Shimizu, 1995, Encapsulation of biologically active proteins in a multiple emulsion, Biosci Biotech Biochem 59(3):492-496.
Shtern, 1996, Hysteresis in swirling jets, J Fluid Mech 309:1-44.
Sia, 2003, Microfluidic devices fabricated in poly(dimethylsiloxane) for biological studies, Electrophoresis 24(21):3563-3576.
Siemering, 1996, Mutations that suppress the thermosensitivity of green fluorescent protein, Curr Biol 6:1653-1663.
Silva-Cunha, 1998, W/O/W multiple emulsions of insulin containing a protease inhibitor and an absorption enhancer: biological activity after oral administration to normal and diabetic rats, Int J Pharm 169:33-44.
Sims, 2000, Immunopolymerase chain reaction using real-time polymerase chain reaction for detection, Anal. Biochem. 281(2):230-2.
Sista, 2007, Development of a Digital Microfluidic Lab-on-a-Chip for Automated Immunoassay with Magnetically Responsive Beads, Doctoral Thesis, Florida State University, 128 pages.
Sista, 2008, Development of a digital microfluidic platform for point care testing, Lab on a Chip 8:2091-2104.

(56) References Cited

OTHER PUBLICATIONS

Siwy, 2003, Electro-responsive asymmetric nanopores in polyimide with stable ion-current signal, Appl Phys A: Mat Sci Proc 76:781-785.
Slappendel, 1994, Normal cations and abnormal membrane lipids in the red blood cells of dogs with familial stomatocytosis hypertrophic gastritis, Blood 84:904-909.
Slob, 1997, Structural identifiability of PBPK models: practical consequences for modeling strategies and study designs, Crit Rev Toxicol. 27(3):261-72.
Smith, 1985, The synthesis of oligonucleotides containing an aliphatic amino group at the 5' terminus: synthesis of fluorescent DNA primers for use in DNA sequence analysis, Nucl Acid Res 13:2399-2412.
Smith, 1986, Fluorescence detection in automated DNA sequence analysis, Nature 321:674-679.
Smith, 1989, Absolute displacement measurements using modulation of the spectrum of white light in a Michelson interferometer, Applied Optics, 28(16):3339-3342.
Smith, 1992, Direct mechanical measurements of the elasticity of single DNA molecules by using magnetic beads, Science 258(5085):1122-1126.
Smith, 2010, Highly-multiplexed barcode sequencing: an efficient method for parallel analysis of pooled samples, Nucleic Acids Res 38(13):e142.
Smyth, 2000, Markers of apoptosis: methods for elucidating the mechanism of apoptotic cell death from the nervous system, Biotechniques 32:648-665.
Sohn, 2000, Capacitance cytometry: Measuring biological cells one by one, PNAS 97(20):10687-10690.
Sola, 2014, Fabrication of a microfluidic cell made of thiolene for microarray applications, 18th Int Conf Miniaturized Systems for Chem and Life Sciences, MicroTAS, San Antonio, TX 1719-1721.
Somasundaram, 1999, Gain studies of Rhodamine 6G dye doped polymer laser, J Photochem Photobiol 125(1-3):93-98.
Song, 2002, Experimental test of scaling of mixing by chaotic advection in droplets moving through microfluidic channels, App Phy Lett 83(22):4664-4666.
Song, 2003, A microfluidic system for controlling reaction networks in time, Angew Chem Int Ed 42(7):768-772.
Song, 2003, Millisecond kinetics on a microluidic chip using nanoliters of reagents, J Am Chem Soc 125:14613-14619.
Song, 2006, Reactions in droplets in microfluidic channels, Angew chem Int ed 45(44):7336-7356.
Soni, 2007, Progress toward ultrafast DNA sequencing using solid-state nanopores, Clin Chem 53:1996-2001.
Soumillion, 2001, Novel concepts for the selection of catalytic activity. Curr Op Biotech 12:387-394.
Spiro, 2000, A bead-based method for multiplexed identification and quantitation of DNA sequences using flow cytometry, Appl Env Micro 66:4258-4265.
Sproat, 1987, The synthesis of protected 5'-mercapto-2',5'-dideoxyribonucleoside-3'-0-phosphorainidites, uses of 5'-mercapto-oligodeoxyribonucleotides, Nucleic Acids Res 15:4837-4848.
Adang, 2001, The contribution of combinatorial chemistry to lead generation: an interim analysis, Curr Med Chem 8:985-998.
Affholter 1999, Engineering a Revolution, Chemistry in Britain 48-51.
Agrawal, 1990, Site-specific functionalization of oligodeoxynucleotides for non-radioactive labelling, Tetrahedron Let 31:1543-1546.
Aharoni, 2005, High-Throughput screens and selections of enzyme-encoding genes, Curr Opin Chem Biol, 9(2):210-6.
Ahn, 2006, Dielectrophoretic manipulation of drops for high-speed microluidic sorting devices, Applied Phys Lett 88:024104.
Akasheh, 2004, Development of piezoelectric micromachined ultrasonic transducers, Sensors and Actuators A Physical, 111:275-287.
Allen, 2000, High throughput fluorescence polarization: a homogeneous alternative to radioligand binding for cell surface receptors J Biomol Screen. 5(2):63-69.

Ammar, 2003, UV/Vis absorption and fluorescence spectroscopic study of novel symmetrical biscoumarin dyes, Dyes and Pigments 57:259-265.
Amstutz, 2001, In vitro display technologies: novel developments and applications. Curr Opin Biotech 12:400-405.
Anarbaev, 1998, Klenow fragment and DNA polymerase alpha-primase fromserva calf thymus in water-in-oil microemulsions, Biochim Biophy Acta 1384:315-324.
Anderson, 1983, Preparation of a cell-free protein-synthesizing system from wheat germ, Methods Enz 101:635-644.
Anderson, 1993, Restriction endonucleases and modification methylases, Curr Op Struct Biol 3:24-30.
Ando, 1999, PLGA microspheres containing plasmid DNA: preservation of supercoiled DNA via cryopreparation and carbohydrate stabilization, J Pharm Sci 88(1):126-130.
Angell, 1983, Silicon micromechanical devices, Scientific Am 248:44-55.
Anhuf, 2003, Determination of SMN1 and SMN2 copy number using TaqMan technology, Hum Mutat 22(1):74-78.
Anna, 2003, Formation of dispersions using flow focusing in microchannels, Appl Phys Lett82(3):364-366.
Armstrong, 1996, Multiple-Component condensation strategies for combinatorial library synthesis, Acc Chem Res 29(3):123-131.
Ashkin, 1987, Optical trapping and manipulation of single cells using infrared laser beams, Nature 330:769-771.
Ashkin, 1987, Optical trapping and manipulation of viruses and bacteria, Science 235(4795):1517-20.
Auroux, 2002, Micro Total Analysis Systems 2: Analytical standard operations and applications, Anal Chem 74(12):2637-2652.
Baccarani, 1977, *Escherichia coli* dihydrofolate reductase: isolation and characterization of two isozymes, Biochemistry 16(16):3566-72.
Bagwe, 2001, Improved drug delivery using microemulsions: rationale, recent progress, and new horizons, Crit Rev Ther Drug Carr Sys 18(1):77-140.
Baker, 2010, Clever PCR: more genotyping, smaller volumes, Nat Meth 7:351-356.
Ballantyne, 1973, Selective area metallization by electron-beam controlled direct metallic deposition, J Vac Sci Tech 10:1094.
Barany, 1991, Genetic disease detection and DNA amplification using cloned thermostable ligase, PNAS 88(1):189-93.
Barany, 1991, The ligase chain reaction in a PCR World, PCR Meth App 1(1):5-16.
Baret, 2009, Fluorescence-activated droplet sorting (FADS): efficient microfluidic cell sorting based on enzymatic activity, Lab Chip 9:1850-1858.
Baret, 2009, Kinetic aspects of emulsion stabilization by surfactants: a microfluidic analysis, Langmuir 25:6088-6093.
Baroud, 2004, Multiphase flows in microfluidics, Physique 5:547-555.
Bauer, 1999, Advances in cell separation: recent developments in counterflow centrifugal elutriation and continuous flow cell separation, J Chromot 722:55-69.
Beebe, 2000, Functional hydrogel structures for autonomous flow control inside microfluidic channels, Nature 404:588-590.
Beer, 2007, On-chip, real-time, single-copy polymerase chain reaction in picoliter droplets, Anal Chem 79(22):8471-8475.
Beer, 2008, On-chip single-copy real-time reverse transcription PCR in isolated picoliter droplets, Anal Chem 80(6):1854-1858.
Bein, 1999, Efficient assays for combinatorial methods for the eiscovery of catalysts, Agnew Chem Int Ed 38:3:323-26.
Benichou, 2002, Double emulsions stabilized by new molecular recognition hybrids of natural polymers, Polym Adv Tech 13:1019-1031.
Benner, 1994, Expanding the genetic lexicon, Trends Biotech 12:158-63.
Benning, 2000, The binding of substrate analogs to phosphotriesterase. J Biol Chem 275:30556-30560.
Berman, 1987, An agarose gel electrophoresis assay for the detection of DNA-binding activities in yeast cell extracts, Meth Enz 155:528-37.
Bernath, 2004, In Vitro Compartmentalization by double emulsions: sorting and gene enrichment by FACS Anal Biochem 325:151-157.

(56) References Cited

OTHER PUBLICATIONS

Bernath, 2005, Directed evolution of protein inhibitors of DNA-nucleases by in vitro compartmentalization (IVC) and nano-droplet delivery, J Mol Biol 345(5):1015-26.
Betlach, 1976, A restriction endonuclease analysis of the bacterial plasmid controlling the EcoRI restriction and modification of DNA, Fed Proc 35:2037-2043.
Bibette, 1999, Emulsions: basic principles, Rep Prog Phys 62:969-1033.
Bico, 2002, Rise of liquids and bubbles in angular capillary tubes, J Colloid & Interface Sc 247:162-166.
Bico, 2002, Self-Propelling Slugs, J Fluid Mech 467:101-127.
Binder, 2009, Mismatch and G-stack modulated probe signals on SNP microarrays, PLoS One, 4(11):e7862.
Binladen, 2007, The use of coded PCR primers enables high-throughput sequencing of multiple homolog amplification products by 454 parallel sequencing, PLoSOne 2(2) e197.
Blanchet, 1993, Laser Ablation and the Production of Polymer Films, Science, 262(5134):719-721.
Boder, 1997, Yeast surface display for screening combinatorial polypeptide libraries, Nat Biotech 15(6):553-7.
Bosque, 2009, Induction of HIV-1 latency and reactivation in primary memory CD4+ T cells, Blood, 113(1):58-65.
Bougueleret, 1984, Characterization of the gene coding for the EcoRV restriction and modification system of E coli, Nucleic Acids Res 12(8):3659-76.
Deyries, 2011, Megapixel digital PCR, Nat. Methods 8, 649-651.
Hildebrand, 1949, Liquid-Liquid Solubility of Perfluoromethylcyclohexane with Benzene, Carbon Tetrachloride, Chlorobenzene, Chloroform and Toluene, J. Am. Chem. Soc, 71: 22-25.
Hindson, 2011, High-Throughput Droplet Digital PCR System for Absolute Quantitation of DNA Copy Number, Anal. Chem., 83, 8604-8610.
Hjelmfelt, 1993, Pattern-Recognition in Coupled Chemical Kinetic Systems, Science, 260(5106):335-337.
Ho, 1989, Site-directed mutageneiss by overlap extension using the polymerase chain reaction, Gene, 77(1):51-9.
Hochuli, 1987, New metal chelate adsorbent selective for proteins and peptides containing neighbouring histidine residues, J Chromatogr 411: 177-84.
Holmes, 1995, Reagents for Combinatorial Organic Synthesis: Development of a New O-Nitrobenzyl Photolabile inder for Solid Phase Synthesis, J. OrgChem., 60: 2318-2319.
Holtze, 2008, Biocompatible surfactants for water-in-fluorocarbon emulsions, Lab Chip, 8, 1632-1639.
Hong, 1999, Stereochemical constraints on the substrate specificity of phosphodiesterase, Biochemistry, 38: 1159-1165.
Hoogenboom, 1997, Designing and optimizing library selection strategies for generating high-affinity antibodies, Trends Biotechnol, 15:62-70.
Hopfinger, 1996, Explosive Breakup of a Liquid Jet by a Swirling Coaxial Jet, Physics of Fluids 8(7):1696-1700.
Hopman, 1998, Rapid synthesis of biotin-, digoxigenin-, trinitrophenyl-, and fluorochrome-labeled tyramides and their application for In situ hybridization using CARD amplification, J of Histochem and Cytochem, 46(6):771-77.
Horton, 1989, Engineering hybrid genes without the use of restriction enzymes: gene splicing by overlap extension, Gene 77(1):61-68.
Hosokawa, 1999, Handling of Picoliter Liquid Samples in a Poly(dimethylsiloxane)-Based Microfluidic Device, Analytical Chemistry, 71(20):4781-4785.
Hsieh, 2009, Rapid label-free DNA analysis in picoliter microfluidic droplets using FRET probes, Microfluidics and hanofluidics 6(3):391-401.
Hsu, 1999, et al., Comparison of process parameters for microencapsulation of plasmid DNA in poly(D, L-lactic-co-glycolic acid microspheres, J Drug Target, 7:313-23.
Hua, 2010, Multiplexed Real-Time Polymerase Chain Reaction on a Digital Microfluidic Platform, Analytical Chemistry 82(6):2310-2316.
Huang, 1991, Kinetic assay of fluorescein mono-beta-D-galactosidase hydrolysis by beta-galactosidase: a front-face measurement for strongly absorbing fluorogenic substrates, Biochemistry, 30:8530-4.
Huang, 1992, A sensitive competitive ELISA for 2,4-dinitrophenol using 3,6-fluorescein diphosphate as a fluorogenic substrate, J Immunol Meth, 149:261.
Huang, 2004, Continuous particle separation through deterministic lateral displacement, Science 304(5673):987-990.
Huang, 2007, Identification of 8 foodborne pathogens by multicolor combinational probe coding technology in a single real-time PCR, Clin Chem., 53(10):1741-8.
Hubert, 2003, Data Concordance from a Comparison between Filter Binding and Fluorescence Polarization Assay Formats for Identification of RUOCK-II Inhibitors, J biomol Screen 8(4):399-409.
Huebner, 2007, Quantitative detection of protein expression in single cells using droplet microfluidics, Chem Com 12:1218-1220.
Hug, 2003, Measurement of the number of molecules of a single mRNA species in a complex mRNA preparation. J Theor Biol.; 221(4):615-24.
Hung, 2004, Controlled Droplet Fusion in Microfluidic Devices, MicroTAS 2004, Sep. 26-30, Malmo, Sweden.
Hung, 2004, Optimization of Droplet Generation by controlling PDMS Surface Hydrophobicity, 2004 ASME International Mechanical Engineering Congress and RD&D Expo, Nov. 13-19, Anaheim, CA, 47-48.
Hutchison, 2005, Cell-free cloning using Phi29 polymerase, PNAS 102(48):17332-17336.
Ibrahim, 2003, High-speed cell sorting: fundamentals and recent advances, Curr Opin Biotchnol, 14(1):5-12.
Ikeda, 2000, Bioactivation of tegafur to 5-fluorouracil is catalyzed by cytochrome P-450 2A6 in human liver microsomes in vitro, Clin Cancer Res 6(11):4409-4415.
Illumina, 2010, Genomic Sequencing, data Sheet, 6 pages.
Inai, 1993, Immunohistochemical detection of an enamel protein-related epitope in rat bone at an early stage of osteogenesis, Histochemistry 99(5):335-362.
Invitrogen, 2008, Specification sheet for Dynabeads® Oligo (dT)25, http://ww.invitrogen.com, 2 pages.
Ismagilov, 2003, Integrated Microfluidic Systems, Angew. Chem. Int. Ed 42:4130-4132.
Jakobovits, 1993, Analysis of homozygous mutant chimeric mice deletion of the immunoglobulin heavy-chain joining region blocks B-cell development and antibody production, PNAS USA 90:2551-255.
Jakobovits, 1993, Germ-line transmission and expression of a human-derived yeast artificial chromosome, Nature 362:255-258.
Janda, 1997, Chemical selection for catalysis in combinatorial antibody libraries, Science, 275:945-948.
Jang, 2003, Controllable delivery of non-viral DNA from porous scaffold, J Controlled Release 86(1):157-168.
Jarvie, 2007, Amplicon Sequencing, Roche Dx Application Note No. 5 (16 pages).
Jermutus, 1998, et al., Recent advances in producing and selecting functional proteins by using cell-free translation, Curr Opin Biotechnol 9(5): 534-48.
Jo, 2003, Encapsulation of Bovine Serum Albumin in Temperature-Programmed Shell-in-Shell Structures, Macromol. Rapid Comm 24:957-962.
Joerger, 1995, Analyte detection with DNA-labeled antibodies and polymerase chain reaction, Clin. Chem. 41(9):1371-7.
Johannsson, 1988, Amplification by Second Enzymes, In ELISA and Other Solid Phase Immunoassays, Kemeny et al (ed.), Chapter 4, pp. 85-106 John Wiley.
Johannsson, 1991, Heterogeneous Enzyme Immunoassays, In Principles and Practice of Immunoassay, pp. 295-325 Stockton Press.
Johnson, 1993, Human antibody engineering: Current Opinion in Structural Biology, 3:564-571.
Johnson, 2002, Protein tyrosine phosphatase 1B inhibitors for diabetes, Nature Review Drug Discovery 1, 696-709.

(56) References Cited

OTHER PUBLICATIONS

Jones, 1986, Replacing the complementarity-determining regions in a human antibody with those from a mouse, Nature, 321:522-525.
Jones, 1997, Quenched BODIPY dye-labeled casein substrates for the assay of protease activity by direct fluorescence measurement, Anal Biochem, 251:144-152.
Jones, 1999, Glowing jellyfish, luminescence and a molecule called coelenterazine, Trends Biotechnol. 17(12):477-81.
Joo, 1999, Laboratory evolution of peroxide-mediated cytochrome P450 hydroxylaion, Nature 399:670.
Joos, 1997, Covalent attachment of hybridizable oligonucleotides to glass supports, Analytical Biochemistry 247:96-101.
Joyce, 1994, In vitro Evolution of Nucleic Acids, Curr. Opp. Structural Biol, 4: 331-336.
Kadir, 1990, Haem binding to horse spleen ferritin, Febs Lett, 276: 81-4.
Kallen, 1966, The mechanism of the condensation of formaldehyde with tetrahydrofolic acid, J. Biol. Chem., 241:5851-63.
Kambara, 1988, Optimization of Parameters in a DNA Sequenator Using Fluorescence Detection, Nature Biotechnology 6:816-821.
Kamensky, 1965, Spectrophotometer: new instrument for ultrarapid cell analysis, Science 150(3696):630-631.
Kanouni, 2002, Preparation of a stable double emulsion (W1/O/W2): role of the interfacial films on the stability of the system, Adv. Collid. Interf. Sci., 99(3): 229-254.
Karapatis, 1998, Direct rapid tooling a review of current research, Rapid Prototyping Journal, 4(2):77-89.
Katanaev, 1995, Viral Q beta RNA as a high expression vector for mRNA translation in a cell-free system, Febs Lett, 359:89-92.
Katsura, 2001, Indirect micromanipulation of single molecules in water-in-oil emulsion, Electrophoresis, 22:289-93.
Kawakatsu, 1997, Regular-sized cell creation in microchannel emulsification by visual microprocessing method, Journal of the American Oil ChemistS Society, 74:317-21.
Keana, 1990, New reagents for photoaffinity labeling: synthesis and photolysis of functionalized perfluorophenyl azides, J. Org. Chem. 55(11):3640-3647.
Keefe, 2001, Functional proteins from a random-sequence library, Nature, 410: 715-718.
Keij, 1994, High-speed photodamage cell sorting: An evaluation of the ZAPPER prototype, Methods in cell biology, 42:371-358.
Kelly, 2005, Detection of Vascular Adhesion Molecule-1 Expression Using a Novel Multimodal Nanoparticle, Circulation Research 96:327-336.
Kelly, 2007, Miniaturizing chemistry and biology in microdroplets, Chem Commun 18:1773-1788.
Kerker, 1983, Elastic and inelastic light scattering in flow cytometry, Cytometry, 4:1-10.
Khandjian, 1986, UV crosslinking of RNA to nylon membrane enhances hybridization signals, Mol. Bio. Rep. 11:107-115.
Kheir, 2012, Oxygen Gas-Filled Microparticles Provide Intravenous Oxygen Delivery, Science Translational Medicine 4(140):140ra88 (10 pages).
Kim, 2003, Type II quantum dots: CdTe/CdSe (core/shell) and CdSe/ZnTe (core/shell) heterostructures, J. Am Chem Soc. 125:11466-11467.
Kim, 2004, Comparative study on sustained release of human growth hormone from semi-crystalline poly(L-lactic acid) and amorphous poly(D,L-lactic-co-glycolic acid) microspheres: morphological effect on protein release, Journal of Controlled Release, 98(1):115-125.
Kircher, 2010, High-throughput DNA sequencing-concepts and limitations, Bioessays 32(6):524-536.
Kiss, 2008, High-throughput quantitative polymerase chain reaction in picoliter droplets, Anal. Chem 80:8975-8981.
Kitagawa, 1995, Manipulation of a single cell with microcapillary tubing based on its electrophoretic mobility, Electrophoresis 16:1364-1368.
Klug, 1994, All you wanted to know about selex, Molecular Biology Reports, 20:97-107.
Klug, 1995, Gene Regulatory Proteins and Their Interaction with DNA, Ann NY Acad Sci, 758: 143-60.
Klug, 1995, Protein motifs 5. Zinc fingers, FASEB J 9(8):597-604.
Knaak, 1995, Development of partition coefficients, Vmax and Km values, and allometric relationships, Toxicol Lett. 79(1-3):87-98.
Knight, 1998, Hydrodynamic Focusing on a Silicon Chip: Mixing Nanoliters in Microseconds, Physical Review Lett 80(17):3863-3866.
Koeller, 2001, Enzymes for chemical synthesis, Nature 409:232-240.
Kohler, 1975, Continuous cultures of fused cells secreting antibody of predefined specificity, Nature, 256:495-7.
Kojima, 2005, PCR amplification from single DNA molecules on magnetic beads in emulsion: application for high-throughput screening of transcription factor targets. Nucleic Acids Res. 33:e150, 9 pages.
Kolb, 1995, Cotranslational folding of proteins, Biochem Cell Biol, 73:1217-20.
Komatsu, 2001, Roles of cytochromes P450 1A2, 2A6, and 2C8 in 5-fluorouracil formation rom tegafur, an anticancer prodrug, in human liver microsomes. Drug Met. Disp., 28:1457-1463.
Kopp, 1998, Chemical amplification: continuous flow PCR on a chip, Science, 280:1046-48.
Koster, 2008, Drop-based microfluidic devices for encapsulation of single cells, Lab on a Chip 8:1110-1115.
Kowalczykowski, 1994, Biochemistry of homologous recombination in *Escherichia coli*, Microbiol Rev 58(3):401-65.
Kozbor, 1984, A human hybrid myeloma for production of human monoclonal antibodies, J. Immunol., 133:3001-3005.
Krafft, 1991, Synthesis and preliminary data on the biocompatibility and emulsifying properties of perfluoroalkylated phosphoramidates as injectable surfactants, Eur. J. Med. Chem., 26:545-550.
Krafft, 2001, Fluorocarbons and fluorinated amphiphiles in drug delivery and biomedical research, Adv Rev Drug Disc 47:209-228.
Krafft, 2003, Emulsions and microemulsions with a fluorocarbon phase, Colloid and Interface Science 8(3):251-258.
Kralj, 2005, Surfactant-enhanced liquid-liquid extraction in microfluidic channels with inline electric-field enhanced coalescence, Lab Chip 5:531-535.
Kricka, 1996, Micromachining: a new direction for clinical analyzers, Pure and Applied Chemistry 68(10):1831-1836.
Kricka, 2003, Microchip PCR, Anal Bioanal Chem 377(5):820-825.
Kritikou, 2005, "It's cheaper in the Picolab," Nature, September, vol. 6, 1 page.
Krumdiek, 1980, Solid-phase synthesis of pteroylpolyglutamates, Methods Enzymol, 524-29.
Kruth, 2003, Lasers and materials in selective laser sintering, Assembly Automation, 23(4):357-371.
Kumagai, 1994, Ablation of polymer films by a femtosecond high-peak-power Ti:sapphire laser at 798 nm, Applied Physics Letters, 65(14):1850-1852.
Kumar, 1989, Activity and kinetic characteristics of glutathione reductase in vitro in reverse micellar waterpool, Biochem Biophys Acta, 996(1-2):1-6.
Kumaresan, 2008, High-throughput single copy DNA amplification and cell analysis in engineered nanoliter droplets, Anal Chem, 80:3522-3529.
Lage, 2003, Whole genome analysis of genetic alterations in small DNA samples using hyperbranched strand displacement amplification and array-CGH, Genome Res 13:294-307.
Laird, 2013, Rapid Quantification of the Latent Reservoir for HIV-1 Using a Viral Outgrowth Assay, PLOS Pathogens 9(5):e1003398.
Lamprecht, 2004, pH-sensitive microsphere delivery increases oral bioavailability of calcitonin, J Control Rel 98(1):1-9.
Lancet, 1993, Probability model for molecular recognition in biological receptor repertoirs, PNAS 90(8):3715-9.
Landergren, 1988, A ligase mediated gene detection technique, Science 241(4869):1077-80.
Lasheras, 1998, Breakup and atomization of a round water jet by a high speed annular air jet, J Fluid Mech 357:351-379.
Laufer, 1996, Introduction to Optics and Lasers in Engineering, Cambridge University Press, Cambridge UK:156-162.

(56) References Cited

OTHER PUBLICATIONS

Leamon, 2003, A massively parallel pictoterplate based platform for discrete picoliter-scale PCR, Electrophoresis 24:3769-3777.
Leary, 2000, Application of advanced cytometric and molecular technologies to minimal residual disease monitoring, Proc SPIE 3913:36-44.
Lee, 2000, Circulating flows inside a drop under time-periodic non-uniform electric fields, Phys Fuilds 12(8):1899-1910.
Lee, 2001, Preparation of silica particles encapsulating retinol using O/W/O multiple emulsions, J Coll Interface Sci 240 (1):83-89.
Lee, 2002, Effective formation of silicone-in-fluorocarbon-in-water double emulsions, J Disp Sci Tech 23(4):491-497.
Lee, 2002, Investigating the target recognition of DNA cytosine-5 methyltransferase Hhal by library selection using in vitro compartmentalisation (IVC), Nucleic Acids Res 30:4937-4944.
Lee, 2004, Special issue on biomedical applications for MEMS and microfluidics, Proc IEEE 92(1):3-5.
Lemof, 2003, An AC magnetohydrodynamic microfluidic switch for Micro Total Analysis Systems, Biomed Microdev 5(I):55-60.
Leng 2009, Microfluidic crystalizaiton, Lab Chip 9:24-23.
Leng, 2010, Agarose droplet microfluidics for highly parallel and efficient single molecule emulsion PCR, Lab Chip 10:2841-2843.
Lesley, 1991, Use of in vitro protein synthesis from PCR-generated templates to study interaction of *E coli* transcription factors with core RNA polymerase, J Biol Chem 266(4):2632-8.
Lesley, 1995, Preparation and use of *E. coli* S-30 extracts, Methods Mol Biol 37:265-78.
Leung, 1989, A method for random mutagenesis of a defined DNA segment using a modified polymerase chain reaction, Technique 1:11-15.
Li, 1995, Single-step procedure for labeling DNA strand breaks with fllourescein- or BODIPY-conjugated deoxynucleotides, Cytometry 20:172-180.
Li, 1997, Transport, manipulation, and reaction of biological cells on-chip using electrokinetic effects, Anal Chem 69(8):1564-1568.
Li, 2005, Multiplexed detection of pathogen DNA with DNA-based fluorescence nanobarcodes, Nat Biotech 23(7):885-889.
Li, 2006, Nanoliter microfluidic hybrid method for simultaneous screening and optimization validated with crystallization of membrane proteins, PNAS 103:19243-19248.
Li, 2018, Microfluidic fabrication of microparticles for biomedical applications, Chem Soc Rev 47(15):5646-5683.
Liao, 1986, Isolation of a thermostable enzyme variant by cloning and selection in a thermophile, PNAS 83:576-80.
Lim, 1980, Microencapsulated islets as bioartificial endocrine pancreas, Science 210(4472):908-10.
Lin, 2007, Self-assembled combinatorial encoding nanoarrays for multiplexed biosensing, Nano Lett 7(2):507-512.
Link, 2004, Geometrically mediated breakup of drops in microfluidic devices, Phys Rev Lettv92(5):054503-1-4.
Link, 2006, Electric control droplets in microfluidic devices, Angew Chem Int Ed 45:2556-2560.
Lipinski, 2001, Experimental and computational approaches to estimate solubility and permeability in drug discovery, , Adv Drug Deliv Rev 46:3-26.
Lipkin, 1988, Biomarkers of increased susceptibility to gastreointestinal cancer: new application to studies of cancer prevention in human subjects, Cancer Res 48:235-245.
Liu, 2000, Passive mixing in a three-dimensional serpentine microchannel, J MEMS 9(2):190-197.
Liu, 2002, Fabrication and characterization of hydrogel-based microvalves, Mecoelectromech. Syst. 11:45-53.
Lizardi, 1998, Mutation detection and single-molecule counting using isothermal rolling-circle amplification. Nat Genet 19(3):225-32.
Lo, 2007, Digital PCR for the molecular detection of fetal chromosomal aneuploidy, PNAS 104(32):13116-13121.
Loakes, 1994, 5-Nitroindole as a universal base analogue, Nucleic Acids Res 22:4039-4043.
Loakes, 1997, Stability and structure of DNA oligonucleotides containing non-specific base analogues, J Mol Biol 270:426-435.
Lodish, 2000, Structure of Nucleic Acids, Section 4.1 , Molecular Cell Biology, 4th edition, New York, 1-3.
Loeker, 2003, FTIR analysis of water in supercritical carbon dioxide microemulsions using monofunctional perfluoropolyether surfanctants, Colloids and Surfaces A: Phys Eng Asp 214:143-150.
Loo, 2004, Nanoshell Enabled Photonics-Based Imaging and Therapy of Cancer, Technology in Cancer Research & Treatment 3(1):33-40.
Lopez-Herrera, 1995, The electrospraying of viscous and non-viscous semi-insulating liquids: scaling laws, Bull Am Phys Soc 40 (12):2041.
Lopez-Herrera, 1999, One-dimensional simulation of the breakup of capillary jets of conducting liquids application to EHD spraying, Aerosol Set 30(7):895-912.
Lopez-Herrera, 2003, Coaxial jets generated from electrified Taylor cones, Aerosol Sci 34:535-552.
Lorenceau, 2005, Generation of polymerosomes from double-emulsions, Langmuir 21(20):9183-9186.
Lorenz, 1991, Isolation and expression of a cDNA encoding Renilla reniformis luciferase, PNAS 88(10):4438-42.
Loscertales, 2002, Micro/nano encapsulation via electrified coaxial liquid jets, Science 295(5560):1695-1698.
Lowe, 2002, Perfluorochemical respiratory gas carriers: benefits to cell culture systems, J Fluorine Chem 118:19-26.
Lu, 2007, Robust fluorescein-doped silica nanoparticles via dense-liquid treatment, Colloids and Surfaces A Phys Eng Asp 303(3):207-210.
Luisi, 1987, Activity and conformation of enzymes in reverse micellar solutions, Meth Enzymol 136:188-216.
Lund, 1988, Assesment of methods for covalent binding of nucleic acids to magnetic beads, Dynabeads, and the characteristics of the bound nucleic acids in hybridization reactions, Nucleic Acids Res 16(22):10861-10880.
Ellman, 1991, Biosynthetic method for introducing unnatural amino acids site-specifically into proteins, Methods Enzymol, 202:301-36.
Endo, 1996, Autocatalytic decomposition of cobalt complexes as an indicator system for the determination of trace amounts of cobalt and effectors, Analyst 121:391-394.
Endo, 1998, Kinetic determination of trace cobalt by visual autocatalytic indication, Talanta 47:349-353.
Engl, 2005, Droplet Traffic at a Simple Junction at Low Capillary Numbers Physical Review Letters, vol. 95, 208304, 1 page.
Eow, 2002, Electrocoalesce-separators for the separation of aqueous drops from a flowing dielectric viscous liquid, Separation and Purification Tech 29:63-77.
Eow, 2002, Electrostatic and hydrodynamic separation of aqueous drops in a flowing viscous oil, Chemical Eng Proc 41:649-657.
Eow, 2002, Electrostatic enhancement of coalescence of water droplets in oil: a review of the technology, Chemical Engineeing Journal 85:357-368.
Eow, 2003, Motion, deformation and break-up of aqueous drops in oils under high electric field strengths, Chemical Eng Proc 42:259-272.
Eow, 2003, The behavior of a liquid-liquid interface and drop-interface coalescence under the influence of an electric field, Colloids and Surfaces A: Physiochern. Eng. Aspects 215:101-123.
Eriksson, 2013, Comparative analysis of measures of viral reservoirs in HIV-1 eradication studies, PLOS Pathogens 9(2):e1003174, 17 pages.
Faca, 2008, A mouse to human search for plasma proteome changes associated with pancreatic tumor development, PLoS Med 5(6):e123:0953-0967.
Fahy, 1991, Self-sustained sequence replication (3SR): an isothermal transcription-based amplification system alternative to PCR, PCR Methods Appl 1:25-33.
Fan, 1994, Micromachining of capillary electrophoresis injectors and separators on glass chips and evaluation of flow at capillary intersections, Anal Chem 66:177-184.
Fan, 2007, Detection of Aneuploidy with Digital PCR, available at https://arxiv.org/ftp/arxiv/papers /0705/0705.1 030.pdf, 16 pages.

(56) References Cited

OTHER PUBLICATIONS

Fastrez, 1997, In vivo versus in vitro screening or selection for catalytic activity in enzymes and abzymes, Mol Biotechnol 7(1):37-55.
Fettinger, 1993, Stacked modules for micro flow systems in chemical analysis: concept and studies using an enlarged model, Sens Actuat B. 17:19-25.
Fiedler, 1998, Dielectrophoretic sorting of particles and cells in a microsystem, Anal Chem 70(9):1909-1915.
Field, 1988, Purification of a RAS-responsive adenylyl cyclase complex from *Saccharomyces cervisiae* by use of an epitope addition method. Mol Cell Biol, 8: 2159-2165.
Fields, 1989, A novel genetic system to detect protein-protein interactions, Nature 340(6230):245-6.
Filella, 1994, TAG-72, CA 19.9 and CEA as tumor markers in gastric cancer, Acta Oncol. 33(7):747-751.
Finch, 1993, Encapsulation and controlled release, Spec Publ R Soc Chem, 138:35, 12 pages.
Fingas, 1997, Studies of Water-In-Oil Emulsions: Stability Studies, Environment Canada, Proceedings of the Twentieth Arctic Marine Oilspill Program Technical Seminer, 1-20.
Fire, 1995, Rolling replication of short DNA circles, PNAS 92(10):4641-5.
Firestine, 2000, Using an AraC-based three hybrid system to detect biocatalysts in vivo, Nat Biotechnol 18: 544-547.
Fisher, 2004, Cell Encapsulation on a Microfluidic Platform, The Eighth International Conference on Miniaturised Systems for Chemistry and Life Scieces, MicroTAS, Malmo, Sweden.
Fletcher, 2002, Micro reactors: principles and applications in organic synthesis, Tetrahedron 58:4735-4757.
Fluri, 1996, Integrated capillary electrophoresis devices with an efficient postcolumn reactor in planar quartz and glass chips, Anal Chem 68:4285-4290.
Fornusek, 1986, Polymeric microspheres as diagnostic tools for cell surface marker tracing, Crit Rev Ther Drug Carrier Syst, 2:137-74.
Fowler, 2002, Enhancement of Mixing by Droplet-Based Microfluidics, Int Conf MEMS 97-100.
Frenz, 2008, Reliable microfluidic on-chip incubation of droplets in delay-lines, Lab on a Chip 9:1344-1348.
Fu, 1999, A microfabricated fluorescence-activated cell sorter, Nature Biotechnology, 17(11):1109-1111.
Fu, 2002, An Integrated Microfabricated Cell Sorter, Anal. Chem., 74: 2451-2457.
Fulton, 1997, Advanced multiplexed analysis with the FlowMetrix system, Clin Chem 43:1749-1756.
Fulwyler, 1965, Electronic Separation of Biological Cells by Volume, Science 150(3698):910-911.
Galan, 2010, A 454 multiplex sequencing method for rapid and reliable genotyping of highly polymorphic genes in large-scale studies., BMC Genomics 11(296):1-15.
Gallarate, 1999, On the stability of ascorbic acid in emulsified systems for topical and cosmetic use, Int J Pharm 188(2):233-241.
Ganan-Calvo, 1998, Generation of Steady Liquid Microthreads and Micron-Sized Monodisperse Sprays and Gas Streams, Phys Rev Lett 80(2):285-288.
Ganan-Calvo, 2001, Perfectly Monodisperse Microbubbling by Capillary Flow Focusing, Phys Rev Lett 87(27):274501-1-4.
Garcia-Ruiz, 1994, Investigation on protein crystal growth by the gel acupuncture method, Acta, Cryst., D50, 99. pp. 484-490.
Garcia-Ruiz, 2001, A super-saturation wave of protein crystallization, J. Crystal Growth, 232:149-155.
Garstecki, 2004, Formation of monodisperse bubbles in a microfiuidic flow-focusing device, Appl Phys Lett 85(13):2649-2651.
Gasperlin, 1994, The structure elucidation of semisolid w/o emulsion systems containing silicone surfactant, Intl J Pharm, 107:51-6.
Gasperlin, 2000, Viscosity prediction of lipophillic semisolid emulsion systems by neural network modeling, Intl J Pharm, 196:37-50.
Gelderblom, 2008, Viral complemntation allows HIV-1 replication without integration, Retrovirology 5:60.

Georgiou, 1997, Display of heterologous proteins on the surface of microorganisms: from the screenign of combinatiorial libraires to live recombinant vaccines. Nat Biotechnol 15(1), 29-34.
Georgiou, 2000, Analysis of large libraries of protein mutants using flow cytometry, Adv Protein Chem, 55: 293-315.
Gerdts, 2004, A Synthetic Reaction NetWork: Chemical Amplification Using Nonequilibrium Autocatalytic Reactions Coupled in Time, J. Am. Chem. Soc 126:6327-6331.
Ghadessy, 2001, Directed Evolution of Polymerase Function by Compartmentalized Self-Replication, PNSAS 98(8):4552-4557.
Gibbs, 1989, Detection of single DNA base differences by competitive oligonucleotide priming, Nucleic Acids Res. 17(7): 2437-48.
Gilliland, 1990, Analysis of cytokine mRNA and DNA: Detection and quantitation by competitive polymerase chain reaction, PNAS, 87(7):2725-9.
Xing, 2011, Novel structurally related compounds reactivate latent HIV-1 in a bcl-2-transduced primary CD4+ T cell model without inducing global T cell activation, Journal of Antimicrobial Chemotherapy, 67(2):398-403.
Xu, 2005, Generation of monodisperse particles by using microfluidics: control over size, shape, and composition, Angew. Chem. Int. Ed. 44:724-728.
Xu, 2009, Design of 240, 000 orthogonal 25mer DNA barcode probes, PNAS, 106(7) p. 2289-2294.
Yamagishi, 1990, Mutational analysis of structure-activity relationships in human tumor necrosis factor-alpha, Protein Eng, 3:713-9.
Yamaguchi, 2002, Insulin-loaded biodegradable PLGA microcapsules: initial burst release controlled by hydrophilic additives, Journal of Controlled Release, 81(3): 235-249.
Yelamos, 1995, Targeting of non-Ig sequences in place of the V segment by somatic hypermutation. Nature 376(6537):225-9.
Yershov, 1996, DNA analysis and diagnostics on oligonucleotide microchips, PNAS 93(10):4913-4918.
Yonezawa, 2003, DNA display for in vitro selection of diverse peptide libraries, Nucleic Acids Research, 31(19): e118, 6 pages.
Yu, 1997, Specific inhibition of PCR by non-extendable oligonucleotides using a 5' to 3' exonuclease-deficient DNA polymerase, Biotechniques 23(4):714-6, 718-20.
Yu, 2001, Responsive biomimetic hydrogel valve for microfluidics. Appl. Phys. Lett 78:2589-2591.
Yu, 2002, Environmental Carcinogenic Polycyclic Aromatic Hydrocarbons: Photochemisrty and Phototoxicity, J Environ Scie Health C Environ Carcinog Exotoxicol Rev, 20(2), 1-43.
Yu, 2007, Quantum dot and silica nanoparticle doped polymer optical fibers, Optics Express 15(16):9989-9994.
Zaccolo, 1996, An approach to random mutagenesis of DNA using mixtures of triphosphate derivatives of nucleoside analogues. J Mol Biol 255(4):589-603.
Zakrzewski, 1980, Preparation of tritiated dihydrofolic acid of high specific activity, Methods Enzymol, 529-533.
Zaug, 1986, The intervening sequence RNA of Tetrahymena is an enzyme, Science 231(4737):470-5.
Zaug, 1986, The Tetrahymena intervening sequence ribonucleic acid enzyme is a phosphotransferase and an acid phosphatase, Biochemistry 25(16):4478-82.
Zaug, 1986, The Tetrahymena ribozyme acts like an RNA restriction endonuclease, Nature 324(6096):429-33.
Zhang, 1993, Substrate specificity of the protein tyrosine phosphatases, PNAS 90: 4446-4450.
Zhang, 1999, A Simple Statistical Parameter for Use in Evaluation and Validation of High Throughput Screening Assays, Journal of Biomolecular Screening, 4(2): 67-73.
Zhao, 1998, Molecular evolution by staggered extension process (StEP) in vitro recombination. Nat Biotechnol 16(3):258-61.
Zhao, 2002, Control and Applications of Immiscible Liquids in Microchannels, J. Am. Chem. Soc, vol. 124:5284-5285.
Zheng, 2003, Screening of Protein Crystallization Conditions on a Microfluidic Chip Using Nanoliter-Size Droplets, J Am Chem Soc 125(37):11170-11171.
Zheng, 2004, A Droplet-Based, Composite PDMS/Glass Capillary Microfluidic System for Evaluating Protein Crystallization Condi-

(56) References Cited

OTHER PUBLICATIONS tions by Microbatch and Vapor-Diffusion Methods with On-Chip X-Ray Diffraction, Angew. Chem., 116:1-4.
Zheng, 2004, Formation of Droplets of Alternating Composition in Microfluidic Channels and Applications to Indexing of Concentrations in Droplet-Based /Assays, Anal. Chem.,76: 4977-4982.
Zheng, 2005, A Microiuidic Approach for Screening Submicroliter Volumes against Multiple Reagents by Using Performed Arrays of Nanoliter Plugs in a Three-Phase Liquid/Liquid/Gas Flow, Angew. Chem. Int. Ed., 44(17):2520-2523.
Zhong, 2011, Multiplex digital PCR: breaking the one target per color barrier of quantitative PCR, Lab on a Chip 11(13):2167-2174.
Zimmermann, 1974, Dielectric Breakdown of Cell Membranes, Biophys J 14(11):881-889.
Zimmermann, 1992, Microscale Production of Hybridomas by Hypo-Osmolar Electrofusion, Hum. Antibod. Hybridomas, 3(1): 14-18.
Zimmermann, 2008, Digital PCR: a powerful new tool for noninvasive prenatal diagnosis?, Prenat Diagn 28, 1087-1093.
Zubay, 1973, In vitro synthesis of protein in microbial systems, Annu Rev Genet, 7: 267-87.
Zubay, 1980, The isolation and properties of CAP, the catabolite gene activator, Methods Enzymol, 65: 856-77.
Zuckermann, 1987, Efficient Methods for Attachment of Thiol-Specific Probes to the 3-end of Synthetic Oligodeoxyribonucleotides, Nucleic Acids Res. 15:5305-5321.
Moudrianakis, 1965, Base sequence determination in nucelic acids with the electron microscope 3. Chemistry and microscopy of guanine-labeled DNA, PNAS 53:564-71.
Mueth, 1996, Origin of stratification in creaming emulsions, Physical Review Letters 77(3):578-581.
Mulbry, 1989, Parathion hydrolase specified by the Flavobacterium opd gene: relationshio between the gene and protein. J Bacteriol, 171: 6740-6746.
Mulder, 1993, Characterization of two human monoclonal antibodies reactive with HLA-B12 and HLA-B60, respectively, raised by in vitro secondary immunization of peripheral blood lymphocytes, Hum. Immunol 36(3):186-192.
Munson, 1980, Ligand: a versatile computerized approach for characterization of ligand-binding systems, Analytical Biochemistry, 107:220-239.
Nakano, 1994, High speed polymerase chain reaction in constant flow, Biosci Biotech and Biochem, 58:349-52.
Nakano, 2003, Single-molecule PCR using water-in-oil emulsion, J Biotech, 102:117-124.
Nakano, 2005, Single-molecule reverse transcription polymerase chain reaction using water-in-oil emulsion, J Biosci Bioeng 99:293-295.
Nametkin, 1992, Cell-free translation in reversed micelles, FEB Letters, 309(3):330-32.
Narang, 1979, Improved phosphotriester method for the synthesis of gene fragments, Methods Enzymol, 68:90-98.
Neiman, 2011, Decoding a substantial set of samples in parallel by massive sequencing, PLoS ONE 6(3):1-7.
Nelson, 1989, Bifunctional oligonucleotide probes synthesized using a novel CPG support are able to detect single base pair mutations, Nucl Acids Res 17(18): 7187-7194.
Nemoto, 1997, In vitro virus: bonding of mRNA bearing puromycin at the 3 terminal end to the C-terminal end of its encoded protein on the ribosome in vitro, Federation of European Biochemical Societies, 414:405-8.
Ness, 2000, Molecular Breeding: the natural approach to protein design. Adv Protein Chem, 55: 261-292.
Ng, 2003, Protein crystallization by capillary counter-diffusion for applied crystallographic structure determination, J. Struct. Biol, 142:218-231.
Ng, 2006, Factors affecting flow karyotype resolution, Cytometry, Part A 69A: 1028-1036.

Nguyen, 2006, Optical detection for droplet size control in microfluidic droplet-based analysis systems, Sensors and Actuators B 117(2):431-436.
Nihant, 1994, Polylactide Microparticles Prepared by Double Emulsion/ Evaporation Technique. I. Effect of Primary Emulsion Stability, Pharmaceutical Research, 11(10):1479-1484.
Nisisako, 2002, Droplet formation in a microchannel network, Lab Chip 2:24-26.
Nisisako, 2002, Formation of droplets using branch channels in a microfluidic circuit, Proceedings of the SICE Annual Conference. International Session Papers 1262-1264.
Nisisako, 2005, Controlled formulation of monodisperse double emulsions in a multiple-phase microluidic system, Sot Matter, 1:23-27.
Nisisako, 2008, Microstructured Devices for Preparing Controlled Multiple Emulsions. Chem. Eng. Technol 31(8):1091-1098.
Nof, 2002, Drug-releasing scaffolds fabricated from drug-loaded microspheres, J. Biomed Mater Res 59:349-356.
Norman, 1980, Flow Cytometry, Med. Phys., 7(6):609-615.
Nygren, 1982, Conjugation of horseradish peroxidase to Fab fragments with different homobifunctional and heterobifunctional cross-linking reagents. A comparative study, J. Histochem. and Cytochem. 30:407-412.
Oberholzer, 1995, Enzymatic RNA replication in self-reproducing vesicles: an approach to a minimal cell, Biochem Biophys Res Commun 207(1):250-7.
Oberholzer, 1995, Polymerase chain reaction in liposomes, Chem. Biol. 2(10):677-82.
Obukowicz, 1988, Secretion and export of IGF-1 in *Escerichia coli* strain JM101, Mol Gen Genet, 215:19-25.
Ogura, 1955, Catalase activity at high concentrations of hydrogen peroxide, Archs Biochem Biophys, 57: 288-300.
Oh, 2002, Distribution of Macropores in Silica Particles Prepared by Using Multiple Emulsions, Journal of Colloid and Interface Science, 254(1): 79-86.
Oh, 2005, World-to-chip microfluidic interface with built-in valves for multichamber chip-based PCR assays, Lab Chip, 5, 845-850.
Okuno, 2003, Recent Advances in Optical Switches Using Silica-based PLC Technology, NTT Technical Review 1(7):20-30.
Okushima, 2004, Controlled production of monodisperse double emulsions by two-step droplet breakup in microfluidic devices, Langmuir 20(23): 9905-8.
Olsen, 2000, Function-based isolation of novel enzymes from a large library, Nat Bioteoltnol 13(10):1071-4.
Omburo, 1992, Characterization of the zinc binding site of bacterial phosphotriesterase, J of Biological Chem, 267:13278-83.
Proskar, 1996, Detection of immobilized amplicons by ELISA-like techniques, Clin. Chem. 42:1547-1555.
Ostermeier, 1999, A combinatorial approach to hybrid enzymes independent of DNA homology, Nat Biotechnol, 17(12):1205-9.
Ott, 1967, Biological and medical research annual report, Los Alamos Scientific Laboratory, 14 pages.
Ouelette, 2003, A new wave of microfluidic devices, Indust Physicist pp. 14-17.
Pabit, 2002, Laminar-Flow Fluid Mixer for Fast Fluorescence Kinetics Studies, Biophys J 83:2872-2878.
Paddison, 2002, Stable suppression of gene expression by RNAi in mammalian cells, PNAS 99(3):1443-1448.
Pain, 1981, Preparation of protein A-peroxidase mono conjugate using a heterobifunctional reagent, and its use in enzyme immunoassays, J Immunol Methods, 40:219-30.
Pannacci, 2008, Equilibrium and Nonequilibrium States in Microluidic Double Emulsions Physical Review Leters, 101(6):164502.
Park, 2001, Model of Formation of Monodispersed Colloids, J. Phys. Chem. B 105:11630-11635.
Park, 2003, Cylindrical compact thermal-cycling device for continuous-flow polymeras chain reaction, Anal Chem, ACS, 75:6029-33.
Parker, 2000, Development of high throughput screening assays using fluorescence polarization: nuclear receptor-ligand-binding and kinase/phosphatase assays, J Biomol Screen, 5(2): 77-88.
Pasternak, 2013, Cell-associated HIV RNA: a dynmic biomarker of viral persistence, Retrovirology 10:41.

(56) References Cited

OTHER PUBLICATIONS

Patel, 2003, Formation of Fluorinated Nonionic Surfactant Microemulsions in Hydrfuorocarbon 134a, Journal of Colloid and Interface Science, 258, 345-353.
Pedersen, 1998, A method for directed evolution and functional cloning of enzymes, PNAS 95(18):10523-8.
Pekin, 2011, Quantitative and sensitive detection of rare mutations using droplet-based microfluidics, Lab on a Chip 11(13):2156-2166.
Tuzel, 2006, Region Covariance: A Fast Descriptor for Detection and Classification, European Conference on Computer Vision (ECCV), 14 pages.
Umbanhowar, 2000, Monodisperse Emulsion Generation via Drop Break Off in a Coflowing Stream, Langmuir 16(2):347-351.
Unger, 2000, Monolithic microfabricated valves and pumps by multylayer soft lithography, Science 288(5463):113-116.
Utada, 2005, Monodisperse double emulsions generated from a microcapillary device, Science, 308:537-541.
Vainshtein, 1996, Peptide rescue of an N-terminal truncation of the stoffel fragment of Taq DNA polymerase, Protein Science, 5:1785-92.
Van der Sluis, 2013, Dendritic Cell-induced Activation of Latent HIV-1 Provirus in Actively Proliferating Primary T Lymphocytes, PLOS Pathog. 9(3): 16 pages.
Van Dilla, 1968, The fluorescent cell photometer: a new method for the rapid measurement of biological cells stained with fluorescent dyes, Annual Report of the Los Alamos Scientific Laboratory of the University of California (Los Alamos, NM), Biological and Medical Research Groupp (H-4) of the Health Division, Compiled by D. G. Ott, pp. 100-105.
Van Dilla, 1969, Cell Microfluorometry: A Method for Rapid Fluorescence Measurement, Science 163(3872):1213-1214.
Vanhooke, 1996, Three-dimensional structure of the zinc-containing phosphotrieesterase with the bound substrate analog diethy 4-methylbenzylphosphonate, Biochemistry 35:6020-6025.
Varga, 1991, Mechanism of allergic cross-reactions—I. Multispecific binding of ligands to a mouse monoclonal anti-DNP IgE antibody. Mol Immunol 28(6), 641-54.
Vary, 1987, A homogeneous nucleic acid hybridization assay based on strand displacement, Nucl Acids Res 15(17):6883-6897.
Venkateswaran, 1992, Production of Anti-Fibroblast Growth Factor Receptor Monoclonal Antibodies by In Vitro Immunization, Hybirdoma, 11(6):729-739.
Verhoeyen, 1988, Reshaping human antibodies: grafting an antilysozyme activity, Science, 239:1534-1536.
Vogelstein, 1999, Digital PCR, PNAS 96(16):9236-9241.
Voss, 1993, Kinetic measurements of molecular interactions by spectrofluorometry, J Mol Recognit, 6:51-58.
Wahler, 2001, Novel methods for biocatalyst screening. Curr Opin Chem Biol, 5: 152-158.
Walde, 1988, Structure and activity of trypsin in reverse micelles, Eur J Biochem, 173(2):401-9.
Walde, 1993, Spectroscopic and kinetic studies of lipases solubilized in reverse micelles, Biochemistry, 32(15):4029-34.
Walde, 1994, Oparin's reactions revisited: enzymatic synthesis of poly(adenylic acid) in micelles and self-reproducing vesicles. J Am Chem Soc, 116: 7541-7547.
Walker, 1992, Isothermal in vitro amplification of DNA by a restriction enzyme/DNA polymerase system, PNAS 89(1):392-6.
Walker, 1992, Strand displacement amplification—an isothermal, in vitro DNA amplification technique, Nucleic Acid Res, 20(7):1691-6.
Wang, 1989, Quantitation of mRNA by the polymerase chain reaction. Proc natl Acad Sci USA 86(24), 9717-21.
Wang, 1990, Design and synthesis of new fluorogenic HIV protease substrates based on resonance energy transfer, Tetrahedron Lett., 31:6493.
Wang, 2002, Preparation of Titania Particles Utilizing the Insoluble Phase Interface in a MicroChannel Reactor, Chemical Communications 14:1462-1463.
Wang, 2008, DEP actuated nanoliter droplet dispensing using feedback control, Lab on a Chip 9:901-909.
Wang, 2010, Quantifying EGFR Alterations in the Lung Cancer Genome with Nanofluidic Digital PCR Arrays, Clinical Chemistry 56:4.
Warburton, 1993, Microcapsules for Multiple Emulsions, Encapsulation and Controlled Release, Spec Publ R Soc Chem, 35-51.
Wasserman, 1989, Structure and reactivity of allyl-siloxane monolayers formed by reaction of allcyltrichlorosilanes on silicon substrates, Langmuir 5:1074-1087.
Weaver, 2010, Taking qPCR to a higher level: Analysis of CNV reveals the power of high throughput qPCR to enhance quantitative resolution, Methods 50, 271-276.
Weil, 1979, Selective and accurate initiation of transcription at the Ad2 major late promotor in a soluble system dependent on purified RNA polymerase II and DNA, Cell, 18(2):469-84.
Werle, 1994, Convenient single-step, one tube purification of PCR products for direct sequencing, Nucl Acids Res 22(20):4354-4355.
Wetmur, 2005, Molecular haplotyping by linking emulsion PCR: analysis of paraoxonase 1 haplotypes and phenotypes, Nucleic Acids Res 33(8):2615-2619.
White, 2009, Digital PCR provides sensitive and absolute calibration for high throughput sequencing, BMC Genomics 10:116.
Wick, 1996, Enzyme-containing liposomes can endogenously produce membrane-constituting lipids, Chem Biol 3(4):277-85.
Wiggins, 2004, Foundations of chaotic mixing, Philos Transact A Math Phys Eng Sci 362(1818):937-70.
Williams, 1979, Methotrexate, a high-affinity pseudosubstrate of dihydrofolate reductase, Biochemistry, 18(12):2567-73.
Williams, 2006, Amplification of complex gene libraries by emulsion PCR, Nature Methods 3(7):545-550.
Wilson, 1999, In vitro selection of functional nucleic acids, Ann. Rev. Biochem. 68: 611-647.
Wittrup, 2001, Protein engineering by cell-surface display. Curr Opin Biotechnology, 12: 395-399.
Wittwer, 1989, Automated polymerase chain reaction in capillary tubes with hot air, Nucleic Acids Res., 17(11) 4353-4357.
Wittwer, 1990, Minimizing the Time Required for DNA Amplification by Efficient Heat Transfer to Small Samples, Anal. Biochem., 186, 328-331.
Wolff, 2003, Integrating advanced functionality in a microfabricated high-throughput fluorescent-activated cell sorter, Lab Chip, 3(1): 22-27.
Woolley, 1994, Ultra-high-speed DNA fragment separations using microfabricated capillary array electrophoresis chips, Proc. Natl. Acad. Sci. USA, 91, 11348-11352.
Woolley, 1996, Functional Integration of PCR Amplification and Capillary Electrophoresis in a Microfabricated DNA Analysis Device, Anal. Chem. 68, 4081-4086.
Wronski, 2002, Two-color, fluorescence-based microplate assay for apoptosis detection. Biotechniques, 32:666-668.
Wu, 1989, The ligation amplification reaction (LAR)-amplification of specific DNA sequences using sequential rounds of template dependent ligation, Genomics 4(4):560-9.
Wyatt, 1991, Synthesis and purification of large amounts of RNA oligonucleotides, Biotechniques 11(6):764-9.
Xia, 1998, Soft Lithography, Angew. Chem. Int. Ed. 37:550-575.
Xia, 1998, Soft Lithography, Ann. Rev. Mat. Sci. 28:153-184.
Xiao, 2007, Rapid DNA mapping by fluorescent single molecule detection, Nucleic Acids Research 35:1-12.
Lunderberg, 1995, Solid-phase technology: magnetic beads to improve nucleic acid detection and analysis, Biotech Ann Rev 1:373-401.
Lundstrom, 2002, Breakthrough in cancer therapy: Encapsulation of drugs and viruses, Curr Drug Disc 19-23.
Lyne, 2002, Structure-based virtual screening: an overview, Drug Disc Tod 7(20):1047-1055.
Ma, 1993, In vitro protein engineering using synthetic tRNA(Ala) with different anticodons, Biochemistry 32(31):7939-45.
Mackenzie, 1985, IABS Symposium on Reduction of Animal Usage in the Development and Control of Biological Products, London, UK, 16 pages.

(56) References Cited

OTHER PUBLICATIONS

Mackenzie, 1986, The application of flow microfluorimetry to biomedical research and diagnosis: a review, Dev Biol Stand 64:181-193.
Maclean, 1999, Glossary of terms used in combinatorial chemistry, Pure Appl. Chem. 71(12):2349-2365.
Magdassi, 1984, Multiple Emulsions: HLB Shift Caused by Emulsifier Migration to External Interface, J. Colloid Interface Sci 97:374-379.
Mahajan, 1998, Bcl-2 and Bax Interactions in Mitochondria Probed with Green Florescent Protein and Fluorescence Resonance Energy Transfer, Nat. Biotechnol. 16(6): 547-552.
Mahjoob, 2008, Rapid microfluidic thermal cycler for polymerase chain reaction nucleic acid amplification. Int J HeatMass Transfer;51:2109-22.
Manafi, 2000, New developments in chromogenic and fluorogenic culture media, 2000, International Journal of Food Microbiology, 60, 205-218.
Manley, 1983, In vitro transcription: whole cell extract, Methods Enzymol, 101:568-82.
Manz, 1991, Micromachining of monocrystalline silicon and glass for chemical analysis systems A look into next century's technology or just a fashionable craze, Trends in Analytical Chemistry 10(5):144-149.
Mao, 1991, Substrate effects on the enzymatic activity of alphachymotrypsin in reverse micelles, Biochem Biophys Res Commun, 178(3):1105-12.
Mao, 1992, Kinetic behaviour of alpha-chymotrypsin in reverse micelles: a stopped-flow study, Eur J Biochem 208(1):165-70.
Mardis, 2008, The impact of next-generation sequencing technology on genetics, Trends Genet 24:133-141.
Margulies, 2005, Genome sequencing in microfabricated high-density picolitre reactors, Nature 437(7057):376-380.
Marks, 1992, Bypassing immunization: building high affinity human antibodies by chain shuffling, BioTechnol 10:779-783.
Marques, 1996, Porous Flow within Concentric Cylinders, Bull Am Phys Soc Div Fluid Dyn 41:1768, 1 page.
Maruno, 1991, Fluorine containing optical adhesives for optical communications systems, J. Appl. Polymer. Sci. 42:2141-2148.
Mason, 1997, Shear Rupturing of Droplets in Complex Fluids, Langmuir, 13(17):4600-4613.
Mastrobattista, 2005, High-throughput screening of enzyme libraries: in vitro evolution of a beta-galactosidase by fluorescence-activated sorting of double emulsions, Chem. Biol. 12(12): 1291-1300.
Masui, 1998, Probing of DNA-Binding Sites of *Escherichia coli* RecA Protein Utilizing 1-anilinonaphthalene-8-Sulfonic Acid, Biochem 37(35):12133-12143.
Matayoshi, 1990, Novel fluorogenic substrates for assaying retroviral proteases by resonance energy transfer, Science 247:954.
Matsubara, 2003, Detection of Single Nucleotide Substitution by Competitive Allele-Specific Short Oligonucleotide Hybridization (CASSOH) With Ummunochromatographic Strip, Human Mutation 22:166-172.
Mattheakis, 1994, An in vitro polysome display system for identifying ligands from very large peptide libraries, PNAS 91:9022-6.
Mayr, 2008, The Future of High-Throughput Screening, JBiomol Screen 13:443-448.
Mazutis, 2009, Droplet-Based Microfluidic Systems for High-Throughput Single DNA Molecule Isothermal Amplification and Analysis, Anal Chem 81(12):4813-4821.
Mazutis, 2009, Multi-step microfluidic droplet processing: kinetic analysis of an in vitro translated enzyme, Lab Chip 9:2902-2908.
McDonald, 2000, Fabrication of microfluidic systems in poly(dimethylsiloxane), Electrophoresis 21(1):27-40.
McDonald, 2002, Poly(dimethylsiloxane) as a material for fabricating microfluidic devices, Account Chem. Res. 35:491-499.
Melton, 1984, Efficient in vitro synthesis of biologically active RNA and RNA hybridization probes from plasmids containing a bacteriophage SP6 promoter, Nucl. Acids Res. 12(18):7035-7056.
Mendel, 1995, Site-Directed Mutagenesis with an Expanded Genetic Code, Annu Rev Biophys Biomol Struct, 24:435-62.
Mendieta, 1996, Complementary sequence correlations with applications to reflectometry studies, Instrumentation and Development 3(6):37-46.
Metzker, 2010, Sequencing Technologies—the next generation, Nature Reviews, vol. 11, pp. 31-46.
Meylan, 1995, Atom/fragment contribution method for estimating octanol-water partition coefficients, J Pharm Sci. 84(1):83-92.
Michalatos-Beloin, 1996, Molecular haplotyping of genetic markers 10 kb apart by allele-specific long-range PCR, Nucleic Acids Research, 24:4841-4843.
Miele, 1983, Autocatalytic replication of a recombinant RNA, J Mol Biol, 171:281-95.
Milstein, 1983, Hybrid hybridomas and their use in immunohistochemistry, Nature 305:537-540.
Mindlin, 1936, A force at a point of a semi-infinite solid, Physics, 7:195-202.
Minshuil, 1999, Protein evolution by molecular breeding, Curr Opin Chem Biol 3(3): 284-90.
Miroux, 1996, Over-production of proteins in *Escherichia coli*: mutant hosts that allow synthesis of some membrane proteins and globular proteins at high levels, J of Mol Biol 260(3):289-98.
Miyawaki, 1997, Fluorescent Indicators for Ca2+ Based on Green Fluorescent Proteins and Calmodulin, Nature, 388:882-887.
Mize, 1989, Dual-enzyme cascade—an amplified method for the detection of alkaline phosphatase, Anal Biochem 179(2): 229-35.
Mock, 1985, A fluorometric assay for the biotin-avidin interaction based on displacement of the fluorescent probe 2-anilinonaphthalene-6-sulfonic acid, Anal Biochem, 151:178-81.
Moldavan, 1934, Photo-electric technique for the counting of microscopical cells, Science 80:188-189.
Monie, 2005, A Novel Assay Allows Genotyping of the Latent Reservoir for Human Imnunodeficiency Virus Type 1 in the Resting CD4+ T Cells of Viremic Patients, Journal of Virology, 79(8):5185-5202.
Montigiani, 1996, Alanine substitutions in calmodulin-binding peptides result in unexpected affinity enhancement, J Mol Biol, 258:6-13.
Moore, 1995, Exploration by lamp light, Nature, 374:766-7.
Morrison, 1984, Chimeric human antibody molecules: mouse antigen-binding domains with human constant region domains, PNAS 81:6851-6855.
Giusti, 1993, Synthesis and characterization of 5' fluorescent dye labeled oligonucleotides, Genome Res 2:223-227.
Glass, 1995, Development of primer sets designed for use with the PCR to amlify conserved genes from filamentous ascomycetes, Applied and Environmental Microbiology, vol. 6, pp. 1323-1330.
Gold, 1995, Diversity of Oligonucleotide Functions Annu Rev Biochem, 64: 763-97.
Gong, 2015, Simple method to prepare oligonucleotide conjugated antibodies and its applicaiotn in multiplex protein detection in single cells, Bioconjugate Chm 27(1):271-225.
Goodall, 1998, Operation of Mixed-Culture Immobilized Cell Reactors for the Metabolism of Meta- and Para-Nitrobenzoate by *Comamonas* Sp. JS46 and *Comamonas* Sp. JS47, Biotechnology and Bioengineering, 59 (1): 21-27.
Gordon, 1999, Solid phase synthesis—designer linkers for combinatorial chemistry: a review, J. Chem. Technol. Biotechnol., 74(9):835-851.
Grasland-Mongrain, 2003, Droplet coalescence in microfluidic devices, 30 pages, From internet: http://w.eleves.ens.fr/home/grasland/rapports/stage4.pdf.
Gray, 1987, High speed crhomosome sorting, Science 238(4825):323-329.
Green, 1992, Selection of a Ribozyme That Functions as a Superior Template in a Self Copying Reaction, Science, 258: 1910-5.
Gregoriadis, 1976, Enzyme entrapment in liposomes, Methods Enzymol 44:218-227.
Griffiths, 2000, Man-made enzymes-from design to in vitro compartmentalisation, Curr Opin Biotechnol 11:338-353.
Griffiths, 2003, Directed evolution of an extremely fast phosphotriesterase by in vitro compartmentalization, EMBO J, 22:24-25.

(56) References Cited

OTHER PUBLICATIONS

Griffiths, 2006, Miniaturising the laboratory in emulsion droplets, Trend Biotech 24(9):395-402.
Grinwood, 2004, The DNA sequence and biology of human chromosome 19, Nature 428:529-535.
Grothues, 1993, PCR amplification of megabase DNA with tagged random primers (T-PCR), Nucl. Acids Res vol. 21(5):1321-1322.
Grund, 2010, Analysis of biomarker data logs, odds, ratios and ROC curves, Curr Opin HIV AIDS 5(6):473-479.
Guatelli, 1990, Isothermal, in vitro amplification of nucleic acids by a multienzyme reaction modeled after retroviral replication, PNAS, 87(5):1874-8.
Guixe, 1998, Ligand-Induced Conformational Transitions in *Escherichia coli* Phosphofructokinase 2: Evidence for an Allosteric Site for MgATP2n, Biochem., 37: 13269-12375.
Gupta, 1991, A general method for the synthesis of 3'-sulfhydryl and phosphate group containing oligonucleotides, Nucl Acids Res 19 (11): 3019-3026.
Haber, 1993, Activity and spectroscopic properties of bovine liver catalase in sodium bis(2-ethylhexyl) sulfosuccinate/isooctane reverse micelles, Eur J Biochem 217(2): 567-73.
Habig, 1981, Assays for differentiation of glutathione S-transferases, Methods in Enzymology, 77: 398-405.
Hadd, 1997, Microchip Device for Performing Enzyme Assays, Anal. Chem 69(17): 3407-3412.
Haeberle, 2007, Microfluidic platforms for lab-on-a-chip applications, Lab on a Chip 7:1081-1220.
Hagar, 1992, The effect of endotoxemia on concanavalin A induced alterations in cytoplasmic free calcium in rat spleen cells as determined with Fluo-3, Cell Calcium 13:123-130.
Hai, 2004, Investigation on the release of fluorescent markers from the w/o/w emulsions by fluorescence-activated cell sorter, J Control Release, 96(3): 393-402.
Haies, 1981, Morphometric study of rat lung cells. I. Numerical and dimensional characteristics of parenchymal cell population, Am. Rev. Respir. Dis. 123:533-54.
Hall, 2003, The EBG system of *E. coli*: origin and evolution of a novel beta-galactosidase for the metabolism of lactose, Genetica 118(2-3):143-56.
Hamady, 2008, Error-correcting barcoded primers for pyrosequencing hundreds of samples in multiplex. Nature Nethods vol. 5, No. 3, p. 235-237.
Han, 2001, Quantum-dot-tagged Microbeads for Multiplexed Optical Coding of Biomolecules, Nat Biotech 19(7):631-635.
Handen, 2002, High-throughput screening- challenges for the future, Drug Discov World, 47-50.
Handique, 2001, On-Chip Thermopneumatic Pressure for Discrete Drop Pumping, Analytical Chemistry, 73:1831-1838.
Hanes, 1997, In vitro selection and evolution of functional proteins by using ribosome display, PNAS 94:4937-42.
Hanes, 1998, Degradation of porous poly(anhydide-co-imide) microspheres and implication for controlled macromolecule delivery, Biomaterials, 19(1-3): 163-172.
Hansen, 2002, A robust and scalable microfluidic metering method that allows protein crystal growth by free interface diffusion, PNAS 99(26):16531-16536.
Harada, 1993, Monoclonal antibody G6K12 specific for membrane-associated differentiation marker of human stratified squamous epithelia and squamous cell carcinoma, J. Oral Pathol. Med 22(4):145-152.
Harder, 1994, Characterization and kinetic analysis of the intracellular domain of human protein tyrosine phosphatase beta (HPTP beta) using synthetic phosphopeptides, Biochem J 298 (Pt 2): 395-401.
Harries, 2006, A Numerical Model for Segmented Flow in a Microreactor, Int J of Heat and Mass Transfer, 46:3313-3322.
Harris, 2008, Single-molecule DNA sequencing of a viral genome, Science 320(5872):106-109.
Harrison, 1993, Micromachining a miniaturized capillary electrophoresis-based chemical analysis system on a chip, Science 261(5123):895-897.
Hasina, 2003, Plasminogen activator inhibitor-2: a molecular biomarker for head and neck cancer progression, Cancer Research 63:555-559.
Haynes, 2012, Digital PCR: A Technology Primer, Principles of Digital PCR and Measurement Issues: The certification of Cytomegalovirus Standard Reference Material (SRM 2366) as a model for future SRMs, National Institute of Standards and Tecnology, San Diego, CA, 4 pages.
Hayward, 2006, Dewetting Instability during the Formation of Polymersomes from BloceCopolymer-Stabilized Double Emulsions, Langmuir, 22(10): 4457-4461.
He, 2005, Selective encapsulation of single cells and subcellular organelles into picoliter- and femtoliter-volume droplets, Anal Chem 77(6):1539-1544.
Head, 2014, Library construction for next generation sequencing, Biotech Rap Disp 56(2):61.
Heim, 1996, Engineering Green Fluorescent Protein for Improved Brightness, Longer Wavelengths and Fluorescence Response Energy Transfer, Carr. Biol, 6(2): 178-182.
Hellman, 2009, Differential tissue-specific protein markers of vaginal carcinoma, Br J Cancer, 100(8): 1303-131.
Henrich, 2012, Low-level detection and quantitation of cellular HIV-1 DNA and 2-ILTR circles using droplet dPCR, J Virol Meth 186(1-2):68-72.
Hergenrother, 2000, Small-Molecule Microarrays: Covalent Attachment and Screening of Alcohol-Containing Small Molecules on Glass Slides, J. Am. Chem. Soc, 122: 7849-7850.
Hermankova, 2003, Analysis of human immunodeficiency virus type 1 gene expression in lately infected reseting CD4 T lymphocytes in vivo, J Virology 77(13) 7383-7392.
Herzer, 2001, DNA Purification, in Molecular Biology Problem Solver: A Laboratory Guide, Edited by Alan S. Gerstein, Ch. 1.
Branebjerg, 1996, Fast mixing by lamination, MEMS Proc 9th Ann 9:441-446.
Braslavsky, 2003, Sequence information can be obtained from single DNA molecules, PNAS 100(7):3960-3964.
Breslauer, 2006, Microfluidics based systems biology, Mol Bio Syst 2:97-112.
Bringer, 2004, Microfluidic systems for chemical kinetics that rely on chaotic mixing in droplets, Phil Trans A Math Phys Eng Sci 362:1-18.
Brown, 1979, Chemical synthesis and cloning of a tyrosine tRNA gene, Methods Enzymol 68:109-151.
Bru, 1991, Product inhibition of alpha-chymotrypsin in reverse micelles. Eur J Biochem 199(1):95-103.
Bru, 1993, Catalytic activity of elastase in reverse micelles, Biochem Mol Bio Int, 31(4):685-92.
Brummelkamp, 2002, A system for stable expression of short interfering RNAs in mammalian cells, Science 296(5567):550-3.
Buican, 1987, Automated single-cell manipulation and sorting by light trapping, Appl Optics 26(24):5311-5316.
Burbaum, 1998, Miniaturization technologies in HTS, Drug Disc Today 3:313-322.
Burns, 1996, Microfabricated structures for integrated DNA analysis, PNAS 93:5556-5561.
Burns, 1998, An integrated nanoliter DNA analysis device, Science 282:484-487.
Burns, 2002, The intensification of rapid reactions in multiphase systems using slug flow in capillaries, Lab on a Chip 1:10-15.
Byrnes, 1982, Sensitive fluorogenic substrates for the detection of trypsin-like proteases and pancreatic elastase, Anal Biochem 126:447.
Cahill, 1991, Polymerase chain reaction and Q beta replicase amplification, Clin Chem 37(9):1482-5.
Caldwell, 1991, Limits of diffusion in the hydrolysis of substrates by the phosphodiesterase from Pseudomonas diminuta, Biochem 30:7438-7444.
Calvert, 2001, Inkjet printing for materials and devices, Chem Mater 13:3299-3305.
Caruccio, 2009, Nextura technology for NGS DNA library preparation: simulaneous fragmentation and tagging by in vitro transposition, Epibio Newsletter.

(56) References Cited

OTHER PUBLICATIONS

Caruthers, 1985, Gene synthesis machines: DNA chemistry and its uses, Science 230:281-285.
Cavalli, 2010, Nanosponge formulations as oxygen delivery systems, Int J Pharmaceutics 402:254-257.
Chakrabarti, 1994, Production of RNA by a polymerase protein encapsulated within phospholipid vesicles, J Mol Evol 39(6):555-9.
Chamberlain, 1973, Characterization of T7-specific ribonucleic acid polymerase. 1. General properties of the enzymatic reaction and the template specificity of the enzyme, J Biol Chem 248:2235-44.
Chan, 2003, Size-Controlled Growth of CdSe Nanocrystals in Microfluidic Reactors, Nano Lett 3(2):199-201.
Chan, 2008, New trends in immunoassays, Adv Biochem Engin/Biotech 109:123-154.
Chang, 1987, Recycling of NAD(P) by multienzyme systems immobilized by microencapsulation in artifical cells, Methods Enzymol, 136(67):67-82.
Chang, 2008, Controlled double emulsification utilizing 3D PDMS microchannels, Journal of Micromechanics and Microengineering 18:1-8.
Chao, 2004, Control of Concentration and Volume Gradients in Microfluidic Droplet Arrays for Protein Crystallization Screening, 26th Annual International Conference of the IEEE Engineering in Medicine and Biology Society, San Francisco, California Sep. 1-5.
Chao, 2004, Droplet Arrays in Microfluidic Channels for Combinatorial Screening Assays, Hilton Head: A Solid State Sensor, Actuator and Microsystems Workshop, Hilton Head Island, South Carolina, Jun. 6-10.
Chapman, 1994, In vitro selection of catalytic RNAs, Curr. op. Struct. Biol., 4:618-22.
Chayen, 1999, Crystallization with oils: a new dimension in macromolecular crystal growth Journal of Crystal Growth, 196:434-441.
Chen, 2001, Capturing a Photoexcited Molecular Structure Through Time-Domain X-ray Absorption Fine Structure, Science 292(5515):262-264.
Chen, 2003, Microfluidic Switch for Embryo and Cell Sorting The 12th International Conference on Solid State Sensors, Actuators, and Microsystems, Boston, MA, Transducers, 1: 659-662.
Chen-Goodspeed, 2001, Enhancement, relaxation, and reversal of the stereoselectivity for phosphotriesterase by rational evolution of active site residues, Biochemistry, 40: 1332-1339.
Chen-Goodspeed, 2001, Structural Determinants of the substrate and stereochemical specificity of phosphotriesterase, Biochemistry, 40(5):1325-31.
Cheng, 2003, Electro flow focusing inmicrofluidic devices, Microfluidics Poster, presented at DBAS, Frontiers in Nanoscience, 1 page.
Cheng, 2006, Nanotechnologies for biomolecular detection and medical diagnostics, Current Opinion in Chemical Biology, 10:11-19.
Chetverin, 1995, Replicable RNA vectors: prospects for cell-free gene amplification, expression, and cloning, Prog Nucleic Acid Res Mol Biol, 51:225-70.
Chiang, 1993, Expression and purification of general transcription factors by FLAG epitope-tagging and peptide elution, Pept Res, 6:62-64.
Chiba, 1997, Controlled protein delivery from biodegradable tyrosino-containing poly(anhydride-co-imide) microspheres, Biomaterials, 18(13):893-901.
Chiou, 2001, A closed-cycle capillary polymerase chain reaction machine, Analytical Chemistry, American Chamical Society, 73:2018-21.
Chiu, 1999, Chemical transformations in individual ultrasmall biomimetic containers, Science, 283:1892-1895.
Chou, 1998, A microfabricated device for sizing and sorting DNA molecules 96:11-13.
Clackson, 1994, In vitro selection from protein and peptide libraries, Trends Biotechnol, 12:173-84.

Clausell-Tormos, 2008, Droplet-based microfluidic platforms for the encapsulation and screening of Mammalian cells and multicellular organisms, Chem Biol 15(5):427-437.
Cohen, 1991, Controlled delivery systems for proteins based on poly(lactic/glycolic acid) microspheres, Pharm Res, 8(6):713-720.
Collins, 2003, Optimization of Shear Driven Droplet Generation in a Microluidic Device, ASME International Mechanical Engineering Congress and R&D Expo, Washington, 4 pages.
Collins, 2004, Microfluidic flow transducer based on the measurements of electrical admittance, Lab on a Chip, 4:7-10.
Compton, 1991, Nucleic acid sequence-based amplification, Nature, 350(6313):91-2.
Cook, 2007, Use and misuse of receiver operating characteristic curve in risk prediction, Circulation 115(7):928-35.
Cooper, 2000, The Central Role of Enzymes as Biological Catalysts, The Cell: A Molecular Approach, 2nd Edition, pp. 1-6.
Cormack, 1996, FACS-optimized mutants of the green fluorescent protein (GFP), Gene 173(1):33-38.
Cortesi, 2002, Production of lipospheres as carriers for bioactive compounds, Biomateials, 23(11): 2283-2294.
Courrier, 2004, Reverse water-in-fluorocarbon emulsions and microemulsions obtained with a fluorinated surfactant, Colloids and Surfaces A: Physicochem. Eng. Aspects 244:141-148.
Craig, 1995, Fluorescence-based enzymatic assay by capillary electrophoresis laser-induced fluoresence detection for the determinination of a few alpha-galactosidase molecules, Anal. Biochem. 226:147.
Creagh, 1993, Structural and catalytic properties of enzymes in reverse micelles, Enzyme Microb Technol 15(5):383-92.
Crosland-Taylor, 1953, A Device for Counting Small Particles suspended in a Fluid through a Tube, Nature 171:37-38.
Crowley, 1973, Electrical breakdown of bimolecular lipid membranes as an electromechanical instability, Biophys J. 13(7):711-724.
Cull, 1992, Screening for receptor ligands using large libraries of peptides linked to the C terminus of the lac repressor, PNAS 89:1865-9.
Curran, 1998, Strategy-level separations in organic synthesis: from planning to practice. Angew Chem Int Ed, 37:1174-11-96.
Czarnik, 1997, Encoding methods for combinatorial chemistry, Curr Opin Chem Biol 1:60-66.
Dankwardt, 1995, Combinatorial synthesis of small-molecule libraries using 3-amino-5-hydroxybenzoic acid, 1:113-120.
David, 1974, Protein iodination with solid-state lactoperoxidase, Biochemistry 13:1014-1021.
Davis, 1987, Multiple emulsions as targetable delivery systems, Meth Enzymol 149:51-64.
Davis, 2006, Deterministic hydrodynamics: Taking blood apart, PNAS 103:14779-14784.
De Gans, 2004, Inkjet printing of polymers: state of the art and future developments, Advanced materials, 16: 203-213.
De Wildt, 2002, Isolation of receptor-ligand pairs by capture of long-lived multivalent interaction complexes, Proceedings of the National Academy of Sciences of the United States, 99, 8530-8535.
DelRaso, 1993, In vitro methodologies for enhanced toxicity testing, Toxicol. Lett. 68:91-99.
Deng, 2008, Design and analysis of mismatch probes for long oligonucleotide microarrays, BMC Genomics; 9:491, 13 pages.
Dickinson, 1994, Emulsions and droplet size control, Wedlock, D.J., Ed., in Controlled Particle Droplet and Bubble Formulation, ButterWorth-Heine-mann, 191-257.
DiMatteo, 2008, Genetic conversion of an SMN2 gene to SMN1: A novel approach to the treatment of spinal muscular atrophy, Exp Cell Res. 314(4):878-886.
Ding, 2001, Scheduling of microfluidic operations for reconfigurable two-dimensional electrowetting arrays, IEEE Trans CADICS 20(12):1463-1468.
Ding, 2003, Direct molecular haplotyping of long-range genomic DNA with M1-PCR, Proc. Natl. Acad. Sci. USA, 100(33):7449-7453.
Dinsmore, 2002, Colioidosomes: Selectively Permeable Capsules Composed of Colloidal Particles, Science 298(5595):1006-1009.

(56) References Cited

OTHER PUBLICATIONS

Dittrich, 2005, A new embedded process for compartmentalized cell-free protein expression and on-line detection in microfluidic devices, Chembiochem 6(5):811-814.
Doi, 1999, STABLE: protein-DNA fusion system for screening of combinatorial protein libraries in vitro, FEBS Lett., 457: 227-230.
Doi, 2004, In vitro selection of restriction endonucleases by in vitro compartmentilization, Nucleic Acids Res, 32(12):e95.
Doman, 2002, Molecular docking and high-throughput screening for novel inhibitors of protein tyrosine phosphatase-1B, J Med Chem, 45: 2213-2221.
Domling, 2000, Multicomponent Reactions with Isocyanides, Angew Chem Int Ed 39(18):3168-3210.
Domling, 2002, Recent advances in isocyanide-based multicomponent chemistry, Curr Opin Chem Biol, 6(3):306-13.
Dorfman, 2005, Contamination-free continuous flow microfluidic polymerase chain reaction for quantitative and clinical applications, Anal Chem 77:3700-3704.
Dove, 2002, Research News Briefs, Nature Biotechnology 20:1213, 1 page.
Dower, 1988, High efficiency transformation of *E. coli* by high voltage electroporation, Nucleic Acids Res 16:6127-6145.
Dressman, 2003, Transforming single DNA molecules into fluorescent magnetic particles for detection and enumeration of genetic variations, PNAS 100:8817-22.
Dreyfus, 2003, Ordered and disordered patterns in two phase flows in microchannels, Phys Rev Lett 90(14):144505-1-144505-4.
Drmanac, 1992, Sequencing by hybridization: towards an automated sequencing of one million M13 clones arrayed on membranes, Elctrophoresis 13:566-573.
Du, 2009, SlipChip, Lab Chip, 9, 2286-2292.
Dubertret, 2002, In vivo imaging of quantum dots encapsulated in phospholipid micelles, Science, 298: 1759-1762.
Duffy, 1998, Rapid Protyping of Microfluidic Systems and Polydimethylsiloxane, Anal Chem 70:474-480.
Duggleby, 1995, Analysis of Enzyme Progress Curves by Nonlinear Regression, Pt D. Academic Press 249:61-90.
Dumas, 1989, Purification and properties of the phosphotriesterase from Psuedomonas diminuta, J Biol Chem 264:19659-19665.
Eckert, 1991, DNA polymerase fidelity and the polymerase chain reaction, Genome Res 1:17-24.
Ecole Polytech Federale de Lausanne, 2014, Tracing water channels in cell surface receptors, PhysOrg News (2 pages).
Edel, 2002, Microfluidic Routes to the Controlled Production of Nanopaticles, Chemical Communications, 1136-1137.
Edris, 2001, Encapsulation of orange oil in a spray dried double emulsion, Nahrung/Food, 45(2):133-137.
Effenhauser, 1993, Glass chips for high-speed capillary electrophoresis separations with submicrometer plate heights, Anal Chem 65:2637-2642.
Eggers, 1999, Coalescence of Liquid Drops, J Fluid Mech 401:293-310.
Ehrig, 1995, Green-fluorescent protein mutants with altered fluorescence excitation spectra, Febs Lett, 367(2):163-66.
Eigen, 1980, Hypercycles and compartments: compartments assists—but does not replace—hypercyclic organization of early genetic information, J Theor Biol, 85:407-11.
Elghanian, 1997, Selective colorimetric detection of polynucleotides based on the distance-dependent optical properties of gold nanoparticles, Science, 277(5329):1078-1080.
Ellington, 1990, In vitro selection of RNA molecules that bind specific ligands, Nature, 346:818-822.
Pelham, 1976, An efficient mRNA-dependent translation system from reticulocyte lysates, Eur J Biochem 67:247-56.
Pelletier, 1999, An in vivo library-versus-library selection of optimized protein-protein interactions, Nature Biotechnology, 17:683-90.
Peng, 1998, Controlled Production of Emulsions Using a Crossflow Membrane, Particle & Particle Systems Characterization 15:21-25.

Pepe, 2004, Limitations of the odds ratio in gauging the performance of a diagnostic, prognostic, or screening marker, American Journal of Epidemiology 159(9):882-890.
Perelson, 1979, Theorectical studies of clonal selection: minimal antibody repertoire size and relaibility of self-non-self discrimination. J Theor Biol 81(4):645-70.
Perez-Gilabert, 1992, Application of active-phase plot to the kinetic analysis of lipoxygenase in reverse micelles, Biochemistry J. 288:1011-1015.
Petrounia, 2000, Designed evolution of enzymatic properties, Curr Opin Biotechnol, 11:325-330.
Pirrung, 1996, A General Method for the Spatially Defined Immobilization of Biomolecules on Glass Surfaces Using 'Caged' Biotin, Bioconjug Chem 7: 317-321.
Ploem, 1993, in Fluorescent and Luminescent Probes for Biological Activity Mason, T. G. Ed., Academic Press, Landon, pp. 1-11.
Pluckthun, 2000, In vitro selection and evolution of proteins, Adv Protein Chem, 55: 367-403.
Pollack, 1986, Selective chemical catalysis by an antibody, Science 234(4783):1570-3.
Pollack, 2002, Electrowetting-based actuation of droplets for integrated microfluidics, Lab Chip 2:96-101.
Pons, 2009, Synthesis of Near-Infrared-Emitting, Water-Soluble CdTeSe/CdZnS Core/Shell Quantum Dots, Chemistry of Materials 21(8):1418-1424.
Posner, 1996, Engineering specificity for folate into dihydrofolate reductase from *Escherichia coli*, Biochemistry, 35:1653-63.
Priest, 2006, Generation of Monodisperse Gel Emulsions in a Microfluidic Device, Applied Physics Letters, 88:024106, 3 pages.
Qi, 1998, Acid Beta-Glucosidase: Intrinsic Fluorescence and Conformational Changes Induced by Phospholipids and Saposin C, Biochem., 37(33): 11544-11554.
Raghuraman, 1994, Emulston Liquid Membranes for Wastewater Treatment: Equillibrium Models for Some Typical Metal-Extractant Systems,Environ. Sci. Technol 28:1090-1098.
Ralhan, 2008, Discovery and Verification of Head-and-neck Cancer Biomarkers by Differential Protein Expression Analysis Using iTRAQ Labeling, Multidimensional Liquid Chromatography, and Tandem Mass Spectrometry, Mol Cell Proteomics 7(6):1162-1173.
Ramanan, 2016, Algae-bacteria interactions, Biotech ADv 34:14-29.
Ramsey, 1999, The burgeoning power of the shrinking laboratory, Nat Biotechnol 17(11):1061-2.
Ramstrom, 2002, Drug discovery by dynamic combinatorial libraries, Nat Rev Drug Discov 1:26-36.
Rasmussen, 2013, Comparison of HDAC inhibitors in clinical development, Human Vacc Immunother 9(5):993-1001.
Raushel, 2000, Phosphotriesterase: an enzyme in search of its natural substrate, Adv Enzymol Relat Areas Mol Biol, 74:51-93.
Rech, 1990, Introduction of a yeast artificial chromosome vector into *Sarrachomyeces cervesia* by electroporation, Nucleic Acids Res 18:1313.
Reyes, 2002, Micro Total Analysis Systems. 1. Introduction, Theory and Technology, Anal Chem 74(12):2623-2636.
Riechmann, 1988, Reshaping human antibodies for therapy, Nature, 332:323-327.
Riess, 2002, Fluorous micro- and nanophases with a biomedical perspective, Tetrahedron 58(20):4113-4131.
Roach, 2005, Controlling nonspecific protein adsorption in a plug-based microfluidic system by controlling inteifacial chemistry using fluorous-phase surfactants, Anal. Chem. 77:785-796.
Roberts, 1969, Termination factor for RNA synthesis, Nature, 224: 1168-74.
Roberts, 1975, Simian virus 40 DNA directs synthesis of authentic viral polypeptides in a linked transcription-translation cell-free system 72(5):1922-1926.
Roberts, 1997, RNA-peptide fusion for the in vitro selection of peptides and proteins, PNAS 94:12297-302.
Roberts, 1999, In vitro selection of nucleic acids and proteins: What are we learning, Curr Opin Struct Biol 9(4): 521-9.
Roberts, 1999, Totally in vitro protein selection using mRNA-protein fusions and ribosome display. Curr Opin Chem Biol 3(3), 268-73.

(56) References Cited

OTHER PUBLICATIONS

Roche, 2011, 454 Sequencing System Guidelines for Amplicon Experimental Design, 50 pages.
Rodriguez-Antona, 2000, Quantitative RT-PCR measurement of human cytochrome P-450s: application to drug induction studies. Arch. Biochem. Biophys., 376:109-116.
Rolland, 1985, Fluorescence Polarization Assay by Flow Cytometry, J. Immunol. Meth., 76(1): 1-10.
Rosenberg, 1975, Inhibition of Human Factor IX by Human Antithrombin, J Biol Chem, 250: 4755-64.
Rosenberry, 1975, Acetylcholinesterase, Adv Enzymol Relat Areas Mol Biol, 43: 103-218.
Rotman, 1961, Measurement of activities of single molecules of beta-galactosidase, PNAS, 47:1981-91.
Rouzioux, 2013, How to best measure HIV reservoirs, Curr Op HIV AIDS 8(3):170-175.
Russon et al., Single-nucleotide polymorphism analysis by allele-specific extension of fluorescently labeled nucleotides in a microfluidic flow-through device, Electrophoresis, 24:158-61 (2003).
Saarela, 2006, Re-usable multi-inlet PDMS fluidic connector, Sensors Actuators B 114(1):552-57.
Sadtler, 1996, Achieving stable, reverse water-in-fluorocarbon emulsions, Angew Chem Int Ed 35(17):1976-1978.
Sadtler, 1999, Reverse water-In-fluorocarbon emulsions as a drug delivery system: an in vitro study, Colloids & Surfaces A: Phys Eng Asp 147:309-315.
Saiki, 1988, Primer directed enzymatic amplification of DNA with a thermostable DNA polymerase, Science 239(4839):487-91.
Sakamoto, 2005, Rapid and simple quantification of bacterial cells by using a microfluidic device, Appl Env Microb 71:2.
Sano, 1992, Immuno-PCR: very sensitive antigen-detection by means of sepcific Ab-DNA conjugates, Science 258(5079):120-122.
SantaLucia, 1998, A unified view of polymer, dumbbell, and oligonucleotide DNA nearest-neighbor thermodynamics, PNAS 95(4):1460-5.
Santra, 2006, Fluorescence lifetime measurements to determine the core-shell nanostructure of FITC-doped silica nanoparticles, J Luminescence 117(1):75-82.
Sawada, 1996, Synthesis and surfactant properties of novel fluoroalkylated amphiphilic oligomers, Chem Commun 2:179-190.
Abate, 2011, Synthesis of monidisperse microparticles from non-Newtonian polymer solutions with microfluidic devices, Adv Mat 23(15):1757-1760.
Chiu, 2008, Noninvasive prenatal diagnosis of chromosomal aneuploidy by massively paralel genomic seuqencing of DNA in maternal plasma, PNAS 105(51):20458-20463.
Dickinson, 1992, Interfacial interactions and the stability of oil-in-water emulsions, Pure Appl Chem 64(11):1721-1724.
Eijk-Van Os, 2011, Multiplex ligation-dependent probe amplification (MLPA(R)) for the detection of copy number variation in genomic sequences, Meth Mol Biol 688:97-126.
Gruner, 2015, Stabilisers for water-in-fluorinated-oil dispersions, Curr Op Coll Int Sci 20:183-191.
Guo, 2010, Simultaneous detection of trisomies 13, 18, and 21 with multiplex ligation dependent probe amplification-based real-time PCR, Clin Chem 56(9):1451-1459.
Luft, 20001, Detection of integrated papillomavirus sequences by ligation-mediaated PCR (DIPS-PCR) and molecular characterization in cervical cancer cells, In J Cancer 92:9-17.
Rogers, 2005, Closing bacterial genoimc sequence gaps with adaptor-PCR, BioTechniques 39(1):1-3.
Shendure, 2008, Next-generation DNA sequencing, Nature Biotechnology, 26(10):1135-1145.

\* cited by examiner

FIG. 6: 3-Plex Assay
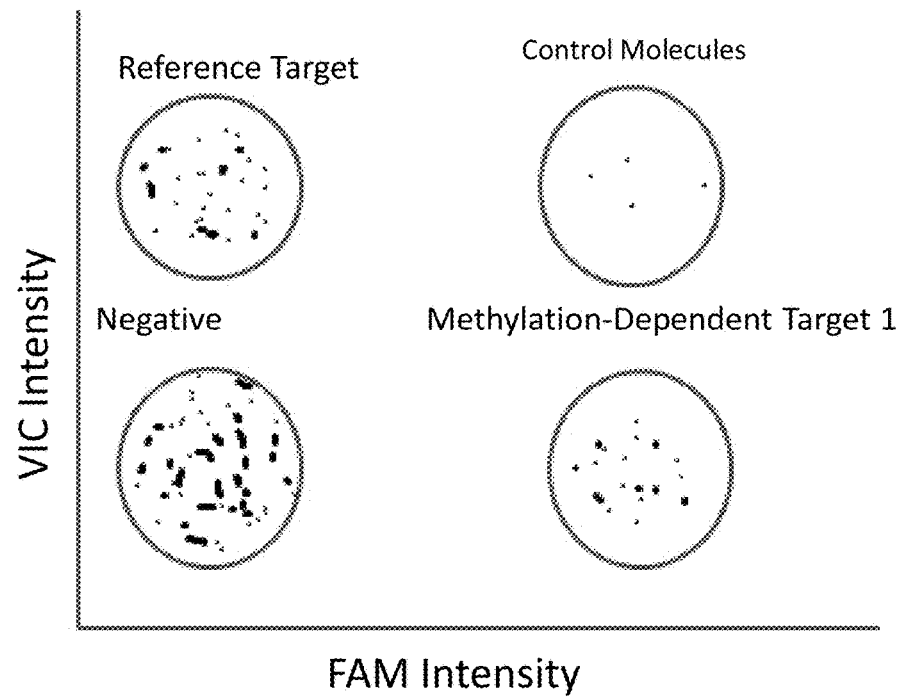
FIG. 7: 4-Plex Assay
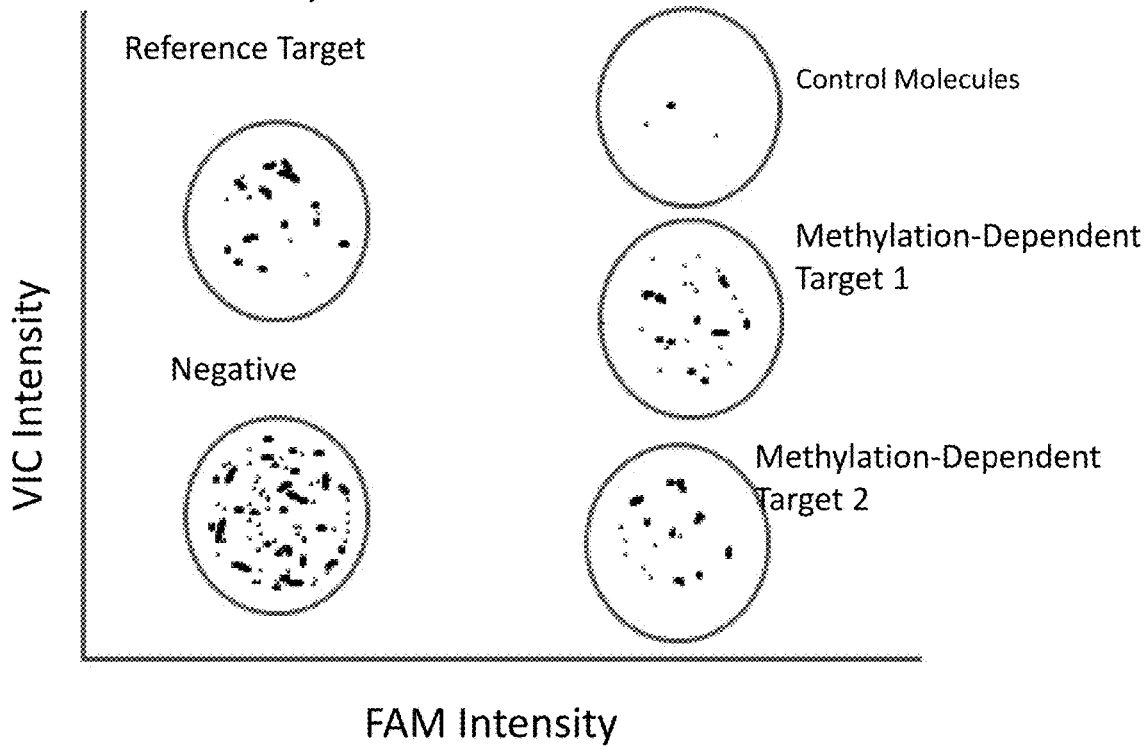

DIGITAL ANALYSIS OF NUCLEIC ACID MODIFICATION

RELATED APPLICATION

The invention claims the benefit of and priority to U.S. Provisional Application No. 61/887,103, filed Oct. 4, 2013, which is incorporated by reference in its entirety.

TECHNICAL FIELD

This invention generally relates to quantification of nucleic acid molecules present in a modification state using target/substrate state-dependent enzymes. For example, in one embodiment the invention comprises quantification of nucleic acid comprising a particular methylation state using methylation-specific restriction enzymes.

BACKGROUND

It is generally understood that in biological systems nucleic acid molecules may be selectively modified in various state or condition specific ways and are thus useful as biomarkers for the various states or conditions. One well known example of nucleic acid modification includes DNA methylation which is generally appreciated as an important regulator of gene expression. DNA methylation may play a role in embryogenesis and epigenetic regulation that has been implicated in the development and progression of a number of diseases, such as cancer and osteoarthritis. For example, nucleic acid methylation in eukaryotic organisms can occur with cytosine species located 5' to a guanine species (i.e., CpG sequences), however other forms of methylation are also known. Research suggests that genes with high levels of methylation in a promoter region are transcriptionally silent, which may allow unchecked cell proliferation. When a promoter region has significant methylation of nucleic acid bases in certain regions, the methylation is typically most prevalent in sequences having CpG repeats, so called "CpG islands." Methylated states have also been implicated in the development and progression of cancer through different mechanisms. Continuing with the present example, other types of methylation mechanisms have also been identified and may occur in heterogeneous/mixed samples such as CpA methylation profiles associated with stem cells or hydroxymethylation.

Species of target/substrate state-dependent enzymes can be useful tools to selectively enrich for a population of nucleic acid in a certain modification state. Continuing with the example of methylation, species of methylation-specific restriction enzymes (also referred to as MSRE) provide a mechanism for enrichment of a population of nucleic acid molecules by utilizing the characteristics of one or more MSRE species that includes an inability to cleave nucleic acid molecules at the enzyme recognition site when in a particular methylation state. For example, in some embodiments when a recognition site for a certain species of restriction enzyme is methylated, the MSRE cleaves the nucleic acid, and consequently the nucleic acid molecule is enzymatically reacted. Alternatively, when the recognition site is in an un-methylated state, the species of MSRE cannot enzymatically react with the nucleic acid molecule, and the integrity of the nucleic acid molecule is preserved.

There are a number of applications where accurate quantification of differences between nucleic acid modification states is desirable in order to accurately identify a disease state or condition. That identification can be particularly challenging in cases where there are only small quantities of starting nucleic acid molecule in a sample available. An example of such a field of application includes a non-invasive test for fetal genomic abnormalities. It is highly desirable that such a test accurately quantifies the amount fetal DNA in maternal blood in order to perform aneuploidy analysis (e.g. trisomy of chromosome 21, 18, or 13). It is therefore advantageous to utilize differences in a methylation state of one or more target regions that exist between a maternal nucleic acid population and a fetal nucleic acid population to quantify the amount of fetal DNA in maternal blood to identify whether a genomic abnormality is present in the fetus. In other words, accurate determination of the percentage of fetal DNA present in a sample drawn from the mother provides confidence in the counting and allocation of chromosome number contributed from the fetal and maternal sources. Another example of a field of application includes cancer analysis where it is generally appreciated that there are differences in methylation state of certain gene targets between cancer cells and normal cells in a tissue type.

SUMMARY

This invention generally relates to increasing the sensitivity of assays for quantification of modified nucleic acid populations using target/substrate state-dependent enzymes. In particular aspects, the invention relates to digital analysis for detection and quantification of differences between methylation-dependent targets (e.g. target regions on a nucleic acid that are in a certain methylation state). For example, methods of the invention utilize digital analysis to quantify a difference in methylation-state at a target region of nucleic acid molecules in a mixed sample by a) enzymatically reacting with molecules in the mixed sample having the target region in a methylation state recognized by the enzyme and in the presence of control nucleic acid comprising the target region in the methylation state recognized by the enzyme, b) amplifying the remaining nucleic acid molecules in the sample, and c) quantifying an amount of total amplifiable nucleic acid from the mixed sample, an amount of molecules comprising the target region, and an amount of the control nucleic acid, where the amount of control nucleic acid is used to determine efficiency of the enzymatic reaction and quantify what number of molecules in the amount of molecules comprising the target region are from molecules in a methylation-state that is not recognized by the enzyme.

Methods of the invention account for the fact that, when detecting differences in methylation-state targets using MSRE's, the difference between a failed assay (i.e. inaccurate quantification) and a positive assay (i.e. accurate quantification) is dependent on the degree of enzymatic reaction of target regions of the nucleic acid in a methylation state recognized by the MSRE (e.g. non-methylated recognition site). The present invention overcomes that dependency by normalizing the amount of measured molecules comprising the target region based on a value of the enzymatic reaction efficiency of the MSRE for the target regions in the recognized methylation-state using a multiplexed assay on the same sample.

In certain aspects, methods of the invention involve providing a mixed sample of nucleic acid molecules comprising target regions in different methylation-states, reference nucleic acid molecules that do not comprise the target region, and a first number of control nucleic acid molecules comprising the target region in the recognized methylation-state (e.g. added to the mixed sample in a known concentration), and conducting methylation-specific enzymatic reaction of nucleic acid in a sample. After enzymatic reaction, a number of the molecules comprising the target regions, a number of the reference nucleic acid molecules, and a number of the control nucleic acid molecules is determined. A value of the efficiency of the methylation-specific enzymatic reaction is then measured using the first number of control nucleic acid molecules and second number of unreacted control nucleic acid molecules. The efficiency value is then used to normalize the number of the molecules comprising the target regions to calculate a number of molecules comprising the target region that are derived from molecules in a methylation-state that is not recognized by the enzyme which can then be used with the number of reference nucleic acid molecules to calculate the difference or ratio of molecules comprising the target region in a recognized methylation state versus the number of molecules comprising the target region in an unrecognized state. The ratio can then be used to identify a disease or condition. In addition, the disease or condition may relate to a percent of the mixed sample deriving from a certain source (e.g. a sample taken from an individual that has multiple targets, some of which include state dependent targets). For example, the normalized ratio may be indicative of a percent of fetal DNA in a sample or indicative of the presence/absence of cancer cells from a tissue. In some cases the source of the mixed sample may include DNA obtained from blood that comprises circulating tumor cells (also referred to as CTC) or cell free DNA (also referred to as cfDNA). In some cases the source of the mixed sample may include DNA obtained from saliva, urine, tear, vaginal secretion, amniotic fluid, breast fluid, breast milk, sweat, or other heterogeneous tissue.

A number of examples are described herein that involve performing methylation-specific enzymatic reaction in order to allow for subsequent detection and quantification of differences in methylation state of molecules at one or more target regions in a mixed sample of nucleic acids. However it will be appreciated that other state specific enzymes exist and the same methods described herein may be employed using these enzymes, mixed samples of nucleic acid molecules having state dependent target regions, and control nucleic acid. Therefore the use of MSRE's should not be considered limiting.

It is generally appreciated that MSRE's include, inter alia, MspI and HpaII which cleave nucleic acid molecules at recognition sites based on methylation status (also sometimes referred to as cleavage sites). It will be appreciated that there are a number of different species of MSRE having different recognition sites and have different activity based on different methylation states. For example, some methylation specific enzymes recognize when a specified recognition site is not methylated resulting in cleavage of the nucleic acid where the same methylated recognition site is not recognized and left intact. In embodiments of the described invention it is important that the enzyme is specific for either the completely modified state or completely unmodified state and not a state where partial modification is recognized by the enzyme (e.g. completely methylated or completely un-methylated in the example of MSRE's). However, it is generally appreciated that the enzymatic activity can be inefficient for a variety of reasons resulting in an incomplete reaction of the recognized nucleic acid molecules in a sample and thus exact quantification of the methylation-state differences of targets can be inaccurate and unreliable without compensating for enzyme efficiency.

As described above, in order to provide accurate quantification of the methylation-state differences within a mixed sample, methods of the invention provide for assessing the efficiency of the methylation-specific enzymatic reaction. The efficiency of the methylation-specific enzymatic reaction in an assay, according to certain embodiments, can be measured by adding a known amount of control nucleic acid molecules to the sample prior to performing methylation specific enzymatic reaction. In the described embodiments, the control nucleic acid molecule includes at least one recognition site in a methylation state that is recognized by the MSRE employed in the assay. After enzymatic reaction the remaining molecules may be amplified (e.g. via digital PCR) and the efficiency of the enzymatic reaction by quantified by counting the number of control nucleic acid molecules present in the sample that should have been enzymatically reacted, and comparing that number to the known amount of control nucleic acid molecules introduced to prior to enzymatic reaction. For example, the MSRE cleavage site of the control nucleic acid is in a recognized methylation state, where an absence of control nucleic acid molecules after enzymatic reaction indicates that enzymatic reaction is complete, and a presence of control nucleic acid after enzymatic reaction indicates that enzymatic reaction is incomplete. For incomplete enzymatic reaction, a number of control nucleic acid remaining after enzymatic reaction relative to the known amount of control nucleic acid added to the assay is used to measure the efficiency of the enzymatic reaction (e.g. percent efficiency). The measured efficiency can then be used to normalize a value of methylation-dependent targets in the assay.

In certain embodiments, one or more MSRE's that recognize one or more regions that differ in methylation state by disease or condition of an individual (or individuals in the case of prenatal testing for aneuploidy) as well as recognizing one or more regions in control nucleic acid molecules comprising the methylation state recognized by the MSRE can be introduced into the mixed sample including the target nucleic acid from the individual(s) for detection of the disease or condition, a reference nucleic acid from the individual, and control nucleic acid not associated with the individual added to the mixed sample in a known quantity. The MSRE's are used to enzymatically react with one or more regions of the target nucleic acid molecules in the recognized methylation state, thereby leaving one or more regions of target nucleic acid molecules that are not in the recognized methylation state intact for subsequent amplification and/or detection. In the same sample, the MSRE's are used to enzymatically react with the regions of the control nucleic acid molecules in the recognized methylation state, as discussed above, in order to determine the efficiency of the enzymatic reaction. In embodiments of the invention described herein, the reference molecules are never a substrate for enzymatic reaction and the control nucleic acid molecules are always a substrate for enzymatic reaction. The number of intact target nucleic acid molecules are subsequently quantified using the number of intact control nucleic acid molecules to normalize for the enzymatic efficiency.

In certain aspects, methods of the invention rely on counting techniques to quantify a ratio or fraction of intact target nucleic acid molecules relative to the number reference nucleic acid molecules. The ratio is indicative of a disease or condition. According to some embodiments, the method provides for counting nucleic acids in partitioned compartments, such as droplets, as in digital PCR. This method involves partitioning the nucleic acid from a sample, after the enzymatic reaction step, into droplets such that a subset of droplets includes nucleic acid from the mixed sample, and amplifying nucleic acid within each droplet. In some embodiments the modification state specific enzymes are included in the mixed sample partitioned into the droplets so that enzymatic reaction step occurs in the droplets, along with any subsequent reactions for processing and detection. The amplified product in each droplet may be detected by, for example, a hydrolysis probe-based assay. In some embodiments, the droplets contain one or fewer target nucleic acid molecules per droplet. In the same or alternative embodiments the nucleic acid molecules partitioned into droplets may include one or more multiplexed target molecules comprising one or more regions recognized by one or more state specific enzymes that differs in state by disease or condition of an individual, one or more reference nucleic acid molecules, and one or more control nucleic acid molecules. In addition, components for an amplification reaction and detection (e.g. probes with detectable labels, primers, reagents) may be introduced into the droplets. The probes with detectable labels and primers introduced into each droplet may be specific for different targets.

An exemplary method for forming droplets involves flowing a stream of aqueous fluid including the mixed sample such that it intersects two opposing streams of flowing carrier fluid that is immiscible with the aqueous fluid. Intersection of the aqueous fluid with the two opposing streams of flowing carrier fluid results in partitioning of the aqueous fluid into individual aqueous droplets. The carrier fluid may be any fluid that is immiscible with the aqueous fluid. An exemplary carrier fluid is oil, particularly, a fluorinated oil. In certain embodiments, the carrier fluid includes a surfactant, such as a fluorosurfactant. The droplets may be flowed through channels.

Detection of the nucleic acid molecules that include molecules with target regions that differ in methylation state, reference molecules, and control nucleic acid molecules can be accomplished by introducing a plurality of probe species that identify the particular nucleic acid types to the mixed sample. Typically the probe species are added to the mixed sample after the enzymatic reaction steps are complete and subsequently included in the partitioned compartments, although as described above in some embodiments the probe species may be included in the mixed sample with the state specific enzyme when partitioned. Members of the plurality of probe species can each include the same detectable label, or a different detectable label. The detectable label is preferably a fluorescent label. The plurality of probe species can include one or more groups of probe species at varying concentrations. The one or more groups of probe species can include the same detectable label which varies in intensity upon detection, due to the varying probe concentrations. In some embodiments, detecting the label may be accomplished by an amplification based technique, such as PCR, digital PCR, or qPCR. In specific embodiments, digital PCR is used to detect the labels. Similarly for amplification, one or more sets of primer pairs may be introduced into the assay after enzymatic reaction. Each set of primer pairs capable of amplifying a specific region of interest from the nucleic acid molecules from an individual (e.g. region comprising the state specific targets and/or reference region) and control nucleic acid molecule.

In certain aspects, embodiments of the invention involve screening for a disease or condition. Screening for a disease or condition may involve counting a first number of compartmentalized portions including a first detectable label that identifies one or more state specific targets, counting a second number of compartmentalized portions comprising a second detectable label corresponding to reference targets, adjusting the first number corresponding to the state specific targets based on the efficiency of a enzyme activity; and determining whether a statistical difference exists between adjusted first number and the second number.

BRIEF DESCRIPTION OF THE DRAWINGS

FIG. 3A depicts the droplet generation chip;
FIG. 3B depicts the droplet spacing for readout;
and FIG. 3C depicts a cartoon of droplet readout by fluorescence.
FIG. 4A shows droplet fluorescence during readout for the most concentrated sample. Each discrete burst of fluorescence corresponded to an individual droplet. Two different groups of droplets were evident: PCR(+) droplets peaking at ~0.8 V and PCR(−) droplets at ~0.1 V;
FIG. 4B shows a histogram of the peak fluorescence intensities of droplets from the complete data trace in (a). PCR(+) and PCR(−) droplets appeared as two very distinct populations centered at 0.78 and 0.10 V, respectively;
FIG. 4C shows the serial dilution of template DNA. Open circles: measured occupancies; solid line: the best fit to Eqn 2 (A=0.15, f=4.8, $R^2$-0.9999).
FIG. 6 illustrates a digital PCR 3-plex assay according to certain embodiments.
FIG. 7 illustrates a digital PCR 4-plex assay according to certain embodiments.

DETAILED DESCRIPTION

Figure 1:
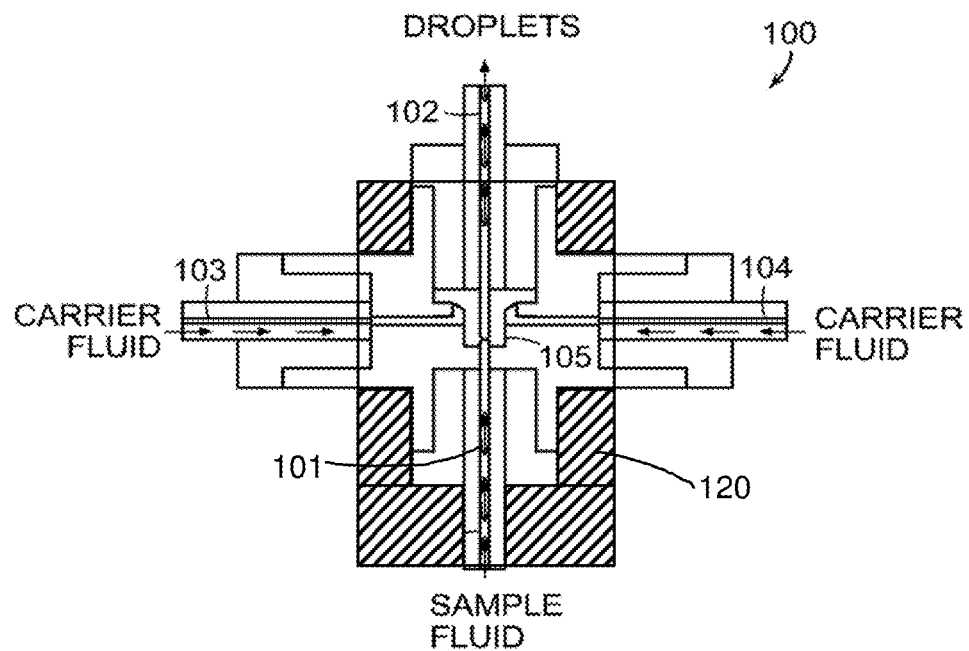
FIG. 1 depicts a droplet formation device.

The invention generally relates to methods for analyzing nucleic acid in a sample. In certain aspects, methods of the invention involve providing a mixed sample of nucleic acid comprising modification state specific targets, reference targets, and a first number of control nucleic acid molecules, and conducting modification state specific enzymatic reaction of nucleic acid in a sample using target/substrate state dependent enzymes. After enzymatic reaction, a number of the intact modification state specific targets, a number of the reference targets, and a second number of the control nucleic acid molecules is determined. A value of the completeness/efficiency of the modification state specific enzymatic reaction is then determined based on the first and second numbers of the control nucleic acid molecules. The efficiency value is then used to normalize the number of intact modification state specific targets counted and/or a ratio of the number of the modification state specific target molecules counted and the number of reference molecules counted. The ratio can then be used to identify a disease or condition. In some embodiments, the disease or condition may relate to embryogenesis, epigenetic regulation, or a disease. In the same or alternative embodiments, the disease or condition may relate to a percent of sample deriving from a certain source. For example, the normalized ratio may be indicative of a percent of fetal DNA in a sample relative to the maternal DNA, or percent of tumor DNA relative to normal DNA. Importantly, the normalized ratio may include a percentage of DNA in a first modification state relative to DNA in a second modification state that occurs in a heterogeneous sample.

The term "modification" of nucleic acid molecules, as used herein, includes any type of modification useable as a marker between a modified and unmodified state, for example, methylation and histone acetylation (e.g. chromatin). In the embodiments described herein, the nucleic acid modification is subject to enzymatic reaction by one or more target/substrate state specific enzymes and thus the modification state of the nucleic acid can be employed to selectively enrich for a population in one state versus a second population in another state. In some embodiments, some enzymes may add a modification a substrate in a state specific manner rather than remove the substrate from the sample, where the modification may be detectable or play a role in the process of detection. For example, embodiments of the invention include any target substrate that can be differentiated by an enzyme which can produce a product in a state specific manner. Other examples could include proteases, lipases, ligases, polymerases, restriction enzymes, 3-OH MSRE, and chromatin motif specific enzymes.

In the described embodiments, nucleic acid molecules in a sample may include one or more modification state specific target regions and one or more reference target regions where enzymatic treatment is employed to "enrich" for molecules comprising the state specific target region in a state not recognized and enzymatically reacted by the state specific enzyme that enables accurate quantification of differences of modification state or imbalances. An important element in the described embodiments includes a 'spike-in' exogenous control nucleic acid that is added in a specific quantity such that following enzymatic treatment of the sample the extent of enzymatic reaction is precisely quantified by counting the remaining number of spiked-in control molecules. It is again important to note that the control nucleic acid molecule is always a substrate for enzyme reaction in the described embodiments. For example, the control nucleic acid comprises one or more regions in the correct modification state that is recognized by the state specific enzyme and enzymatically reacted. A value for the extent of enzymatic reaction is used to determine a 'normalizing factor' for quantification of the number of molecules that should not be subject to enzymatic reaction.

For example, a methylation state specific target region comprises one or more substrate/recognition sites for at least one MSRE and resides, all or in part, within a target region or locus of a nucleic acid where the presence or absence of methylation at the locus is population dependent and where a difference between populations indicates the presence of a disease or condition. Further, the methylation state specific target region comprises one or more sets of sites that are recognized by primers and probes where the sets of sites may be the same as or different from the recognition site(s) for the MSRE. A methylation state independent reference molecule comprises one or more endogenous control regions that is independent of the enzymatic treatment for quantification of the amount of input molecules from an individual in the mixed sample (e.g. counting a target that is not a substrate/recognition site for the enzyme(s)). In the presently described example, if the target/assay is "methylation state independent", containing no potential MSRE cleavage sites, then counting the number of this target with a digital amplification technique (such as digital PCR) assay results in a methylation state independent cluster on a 2-D scatter plot that indicates the number of "genome equivalents" of DNA in the sample. The number of genome equivalents is useful in the calculation of the difference between the number of modified versus unmodified molecules in a sample comprising a mixture of both species (e.g. a mixed or heterogeneous sample). For instance, in the case where an MSRE recognizes the un-methylated state of a recognition site, the number of reference molecules representing the genome equivalents will be the denominator and the number of target molecules counted in the methylated state the numerator in the fraction for counting the number of methylated target loci molecules per genomic equivalent in the sample.

Embodiments of a reference molecule comprises a region of a nucleic acid molecule that do not have a recognition site for any the enzymes used to enzymatically react with the methylation dependent targets. It is again important to note that the reference molecule is never a substrate for enzyme reaction in the described embodiments. In addition, a reference molecule is selected due its lack of copy number variation so that the number of genome equivalents in the mixed sample can be easily and accurately assessed. In certain embodiments, multiple different methylation state dependent targets, reference molecules, and control nucleic acid molecules can be assessed in a single assay. The reference nucleic acid can be used to determine a total amount of amplifiable genome equivalents in a sample as compared to an amount of the methylation state specific targets.

Methods of the invention involve performing modification state specific enzymatic reaction in order to allow for subsequent detection of modification state specific targets in nucleic acid. One example includes methylation state specific enzymatic reaction that utilizes MSRE's that cleave recognition sites having specific sequence composition based on methylation status. For example, some species of MSRE recognize an un-methylated site and cleaves the nucleic acid resulting in enzymatic reaction with the un-methylated target nucleic acid and leave molecules comprising the methylated recognition sites of methylation state specific targets intact. The intact molecules can then be used in subsequent processing steps such as amplification and quantification. However in the present example, the MSRE enzymatic reaction may not be 100% efficient resulting in inefficient and incomplete enzymatic reaction of the un-methylated target regions, and thus the number of intact molecules counted from the methylation state specific target molecules includes the expected methylated population and some number of unexpected un-methylated molecules counted as false positives. Therefore, in order to accurately quantify the number of modification state specific targets in the particular state, embodiments of the invention provide for assessing the efficiency of the modification-specific enzymatic reaction.

The efficiency of the modification-specific enzymatic reaction in an assay, according to certain embodiments, can be measured by adding a known amount of control nucleic acid to the assay prior to performing modification-specific enzymatic reaction. In the described embodiments, the control nucleic includes a modification-specific restriction enzyme cleavage site and is in a modification state that is recognized by the enzyme for enzymatic reaction. In the described embodiments, the number of the control nucleic acid molecules remaining after the enzymatic reaction step are counted and compared to the known amount of control nucleic acid added prior to enzymatic reaction to determine a measure of the efficiency of enzymatic reaction. For example, in some embodiments the modification-specific restriction enzyme cleavage site of the control nucleic acid is non-modified and recognized for cleavage by the enzyme so that an absence of control nucleic acid after enzymatic reaction indicates that the enzymatic reaction is complete, whereas a presence of some amount of control nucleic acid after enzymatic reaction indicates that the enzymatic reaction is incomplete. For incomplete enzymatic reaction, a number of control nucleic acid remaining after the enzymatic reaction relative to the known amount of control nucleic acid added to the assay is used to measure the efficiency of the enzymatic reaction. The measured efficiency can then be used to normalize a value of modification state specific targets of unknown starting quantity within the assay. That is, the measured efficiency can be used to normalize an amount of methylation state specific targets in a sample. For instance, the number of modification state specific targets counted after enzymatic reaction may be adjusted based on the measured efficiency of the enzymatic reaction corresponding to the number of unreacted control nucleic acid molecules counted. A ratio of the adjusted number of modification-dependent targets to the number of reference targets is then determined. Alternatively, ratio of the number of modification-dependent targets to the number of reference targets is determined first, and then the ratio is adjusted based the measured efficiency of the enzymatic reaction corresponding to the amount of the control nucleic acid. The ratio may be indicative of a disease or condition.

The normalization process using the measure of enzymatic reaction efficiency is very important for the precision of the assay and confidence that the number of molecules counted as false positive or false negative are minimized. The precision of the assay is particularly important when the number of molecules in a certain modification state in the sample available for counting is very low. For example, a heterogeneous sample may comprise a fraction of target nucleic acid molecules in a certain modification state associated with a disease or condition, where the fraction is less than 5%, less than 2% or less than 1% of the heterogeneous sample. In the present example the heterogeneous sample may be employed in prenatal testing for genetic aneuploidy where the fetal fraction of DNA can range from about 2-10%, or less than 2% of the DNA in the heterogeneous sample. Typically, an expected ratio of maternal to fetal chromosomes would be expected to be 1:1 for a normal fetus. However, in the case where a fetal aneuploid condition exists, the statistics for accurately identifying the aneuploid condition depend heavily on the amount of the fetal fraction of DNA with the chromosomal abnormality (e.g. particularly if low, ~3% or less) and/or when the total number of countable molecules in the heterogeneous sample is low. In such cases precision of the assay is statistically important in order to accurately call the existence of the aneuploid condition. In other words, a low fetal fraction from a sample with a low number of countable molecules can result in a small difference in calculated ratio where the precision of detection provides measure of statistical confidence that the small difference in ratio can be accurately called as an aneuploid condition.

It will be appreciated that prenatal testing is provided in the example above, however the same applies to cancer analysis, or other assay of heterogeneous tissues using embodiments of the described invention. Therefore, the example of prenatal testing should not be considered as limiting.

Some embodiments of the invention involve determining a number of target nucleic acid molecules in the sample, such as by determining a number of modification state specific targets, determining a number of reference molecules, and determining a number of control nucleic acid molecules. For example, the numbers of molecules may be determined by detecting target-specific detectable labels that may be coupled to probes, such as hydrolysis probes.

In one aspect, the invention provides droplets containing a single nucleic acid template or fewer, amplification reagents, and one or more detectable probes. The amplification reagents may include multiplexed PCR primers that along with the detectable probes may be specific to the modification-dependent target(s), reference target(s), or control nucleic acid(s). Methods of the invention also provide for detecting the nucleic acid template by forming such droplets and amplifying the nucleic acid templates using droplet based digital amplification.

Reactions within microfluidic droplets may yield very uniform fluorescence intensity at the end point, and ultimately the intensity depends on the efficiency of probe hydrolysis. Thus, in another aspect of the methods of the invention, different reactions with different efficiencies can be discriminated on the basis of end point fluorescence intensity alone even if they have the same color. Furthermore, in another method of the invention, the efficiencies can be tuned simply by adjusting the probe concentration, resulting in an easy-to-use and general purpose method for multiplexing. In another aspect of the invention, adding multiple colors increases the number of possible reactions geometrically, rather than linearly as with qPCR, because individual reactions can be labeled with multiple fluorophores.

Nucleic Acids

Nucleic acid is generally is acquired from a sample or a subject. Target molecules for labeling and/or detection according to the methods of the invention include, but are not limited to, genetic and proteomic material, such as DNA, genomic DNA, RNA, expressed RNA, chromosomal and/or extra-chromosomal targets (e.g. mitochondrial, episomal, exosomal). Methods of the invention are applicable to DNA from whole cells or to portions of genetic or proteomic material obtained from one or more cells, or cell-free DNA. For a subject, the sample may be obtained in any clinically acceptable manner, and the nucleic acid templates are extracted from the sample by methods known in the art. Nucleic acid templates can be obtained as described in U.S. Patent Application Publication Number US2002/0190663 A1, published Oct. 9, 2003. Generally, nucleic acid can be extracted from a biological sample by a variety of techniques such as those described by Maniatis, et al. (Molecular Cloning: A Laboratory Manual, Cold Spring Harbor, N.Y., pp. 280-281, 1982), the contents of which are incorporated by reference herein in their entirety.

Nucleic acid templates include deoxyribonucleic acid (DNA) and/or ribonucleic acid (RNA). Nucleic acid templates can be synthetic or derived from naturally occurring sources. In one embodiment, nucleic acid templates are isolated from a biological sample containing a variety of other components, such as proteins, lipids and non-template nucleic acids. Nucleic acid templates can be obtained from any cellular material, obtained from an animal, plant, bacterium, fungus, or any other cellular organism. Biological samples for use in the present invention include viral particles or preparations. Nucleic acid templates can be obtained directly from an organism or from a biological sample obtained from an organism, e.g., from blood, urine, cerebrospinal fluid, seminal fluid, saliva, sputum, stool and tissue. In a particular embodiment, nucleic acid is obtained from fresh frozen plasma (FFP). Any tissue or body fluid specimen may be used as a source for nucleic acid for use in the invention. Nucleic acid templates can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA.

In some embodiments nucleic acid molecules obtained from biological samples is fragmented to produce suitable template molecules for analysis. In one embodiment, nucleic acid from a biological sample is fragmented by sonication. It will however be appreciated that there are numerous methods for fragmenting nucleic acid molecules known in the related art and any method may be used with the presently described embodiments.

A biological sample as described herein may be homogenized or fractionated in the presence of a detergent or surfactant. The concentration of the detergent in the buffer may be about 0.05% to about 10.0%. The concentration of the detergent can be up to an amount where the detergent remains soluble in the solution. In a preferred embodiment, the concentration of the detergent is between 0.1% to about 2%. The detergent, particularly a mild one that is nondenaturing, can act to solubilize the sample. Detergents may be ionic or nonionic. Examples of nonionic detergents include triton, such as the Triton® X series (Triton® X-100 t-Oct-C6H4-(OCH2-CH2)xOH, x=9-10, Triton® X-100R, Triton® X-114 x=7-8), octyl glucoside, polyoxyethylene(9) dodecyl ether, digitonin, IGEPAL® CA630 octylphenyl polyethylene glycol, n-octyl-beta-D-glucopyranoside (betaOG), n-dodecyl-beta, Tween® 20 polyethylene glycol sorbitan monolaurate, Tween® 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), .beta.-mercaptoethanol, DTE, GSH, cysteine, cysteamine, tricarboxyethyl phosphine (TCEP), or salts of sulfurous acid. Once obtained, the nucleic acid is denatured by any method known in the art to produce single stranded nucleic acid templates and a pair of first and second oligonucleotides is hybridized to the single stranded nucleic acid template such that the first and second oligonucleotides flank a target region on the template.

Nucleic acid molecules within a sample may include modified regions as discussed above. For example, prokaryotic nucleic acid is methylated at cytosine and adenosine residues (see, e.g., McClelland et al., Nuc. Acids. Res. 22:3640-3659 (1994). Methylation of prokaryotic nucleic may protect the nucleic from enzymatic reaction by cognate restriction enzymes, i.e., foreign DNAs (which are not methylated in this manner) that are introduced into the cell are enzymatically reacted by restriction enzymes which cannot enzymatically react with the methylated prokaryotic nucleic acid. Nucleic acid methylation patterns can be used to identify specific bacterial types (e.g., genus, species, strains, and isolates).

Mammalian nucleic acid is often methylated at cytosine residues, typically these cytosines are 5' neighbors of guanine (CpG). This methylation has been shown by several lines of evidence to play a role in gene activity, cell differentiation, tumorigenesis, X-chromosome inactivation, genomic imprinting and other major biological processes (Razin and Riggs eds. in DNA Methylation Biochemistry and Biological Significance, Springer-Verlag, N.Y., 1984). Research suggests that genes with high levels of methylation in a promoter region are transcriptionally silent, which may allow unchecked cell proliferation. When a promoter region has excessive methylation, the methylation is typically most prevalent in sequences having CpG repeats, so called "CpG islands." Undermethylation (hypomethylation) has also been implicated in the development and progression of cancer through different mechanisms.

In eukaryotic cells, methylation of cytosine residues that are immediately 5' to a guanosine, occurs predominantly in CG poor loci (Bird, Nature 321:209 (1986)). In contrast, discrete regions of CG dinucleotides called CpG islands remain unmethylated in normal cells, except during X-chromosome inactivation and parental specific imprinting (Li, et al., Nature 366:362 (1993)) where methylation of 5' regulatory regions can lead to transcriptional repression.

Aberrant methylation, including aberrant methylation at specific loci, is often associated with a disease state. For example, de novo methylation of the Rb gene has been demonstrated in a small fraction of retinoblastomas (Sakai, et al., Am. J. Hum. Genet., 48:880 (1991)), and a more detailed analysis of the VHL gene showed aberrant methylation in a subset of sporadic renal cell carcinomas (Herman, et al., PNAS USA, 91:9700 (1994)). Expression of a tumor suppressor gene can also be abolished by de novo DNA methylation of a normally unmethylated 5' CpG island. See, e.g., Issa, et al., Nature Genet. 7:536 (1994); Merlo, et al., Nature Med. 1:686 (1995); Herman, et al., Cancer Res., 56:722 (1996); Graff, et al., Cancer Res., 55:5195 (1995); Herman, et al., Cancer Res. 55:4525 (1995). Methylation of the p16 locus is associated with pancreatic cancer. See, e.g., Schutte et al., Cancer Res. 57:3126-3131 (1997). Methylation changes at the insulin-like growth factor II/H19 locus in kidney are associated with Wilms tumorigenesis. See, e.g., Okamoto et al., PNAS USA 94:5367-5371 (1997). The association of alteration of methylation in the p15, E-cadherin and von Hippel-Lindau loci are also associated with cancers. See, e.g., Herman et al., PNAS USA 93:9821-9826 (1997). The methylation state of GSTP 1 is associated with prostate cancer. See, e.g., U.S. Pat. No. 5,552,277. Tumors where certain genomic loci are methylated have been found to respond differently to therapies such as cis-platin or radiation treatment than tumors where the same genomic loci are un-methylated. It is clear that DNA from tumor cells at certain genomic loci can be different in the levels of DNA methylation and in this way can be distinguished from the DNA from adjacent normal cells. DNA from tumor cells has been found in various body fluids and other clinical specimens collected from cancer patients. For example, methylated DNA having the same sequence of tumor suppressor genes has been found in serum, urine, saliva, sputum, semen, lavages, cell scrapes, biopsies, resected tissues, and feces. Therefore, detection of altered methylation profiles at loci where such alterations are associated with disease can be used to provide diagnoses or prognoses of disease.

Other examples include aberrantly methylated SEPT9 DNA in plasma correlated with occurrence of colorectal cancer (See deVos et al. Clin Chem. 2009 July; 55(7):1337-46); MGMT promoter methylation predictive of response to radiotherapy and chemotherapy (See Rivera et al Neuro Oncol (2010) 12 (2): 116-121); and RASSF1A implicated in cancer (See Dis Markers. 2007; 23(1-2):73-87) as well as a fetal marker.

It will also be appreciated the RNA may exhibit differences in methylation state and is considered within the scope of the described embodiments.

Modification-Specific Enzymatic Reaction

Embodiments of the invention provides for performing modification specific enzymatic reaction of nucleic acid in the sample. In some cases, enzymatic reaction is performed prior to partitioning the nucleic acid for digital analysis, however enzymatic reaction may also be performed within the partitions. In some embodiments methylation-specific enzymatic reaction is used to enrich for a particular target-state to enable accurate quantification. For example, enrichment of one target-state (e.g. methylated or un-methylated) improves the precision and confidence of statistical accuracy of numbers derived from counting target copy numbers in a heterogeneous mixture (e.g. if a completely enriched 100% fetal fraction is prepared, then one needs to see a 50% increase in counts of chromosome 21 targets compared to a normal diploid chromosome target, whereas if the fetal fraction is 10% then one needs to see a 5% increase to call out an aneuploidy condition such as trisomy). The amount of input material and the precision of the measurement are very much improved by using enriched material.

The enrichment occurs from methylation-specific enzymatic reaction that prevents a target locus in a methylation state from being amplified such that target loci in the other methylation state are amplified and detected. In addition, methylation-specific enzymatic reaction is also used to enzymatically react with a known quantity of control nucleic acid, placed in the sample, containing MSRE cleavage sites in the recognized methylation state. As discussed, a comparison of the quantity of the control nucleic acid molecules after enzymatic reaction and the known quantity of control nucleic acid molecules placed in the sample allows one to determine the efficiency of the enzymatic reaction.

Methylation-specific enzymatic reaction techniques are known in the art, and utilize MSRE's. Some species of methylation-specific restriction enzymes cleave DNA at or in proximity to an un-methylated recognition sequence but does not cleave at or in proximity to the same sequence when the recognition sequence is methylated. Alternatively, some species of MSRE's cleave DNA at or in proximity to a methylated recognition sequence but does not cleave at or in proximity to the same sequence when the recognition sequence is un-methylated. Exemplary MSRE's are described in, e.g., McClelland et al., Nucleic Acids Res. 22(17):3640-59 (1994) and http://rebase.neb.com. In addition, MSRE's are described in PCR: Methods Express: Chapter 17 PCR-based methods to determine DNA methylation status at specific CpG sites using methylation-specific restriction enzymes. (S. Hughes and A. Moody, eds., 2007). Another PCR-based process that involves enzymatic reaction of genomic DNA with MSRE's prior to PCR amplification is described in Singer-Sam et al., Nucl. Acids Res. 18:687, 1990.

Suitable methylation-specific restriction enzymes that do not cleave DNA at or near their recognition sequence when a cytosine within the recognition sequence is methylated at position C5 include, e.g., Aat II, Aci I, Acl I, Age I, Alu I, Asc I, Ase I, AsiS I, Bbe I, BsaA I, BsaH I, BsiE I, BsiW I, BsrF I, BssH II, BssK I, BstB I. BstN I, BstU I, Cla I, Eae I, Eag I, Fau I, Fse I, Hha I, HinP1 I, HinC II, Hpa II, Hpy99 I, HpyCH4 IV, Kas I, Mbo I, Mlu I, MapA1 I, Msp I, Nae I, Nar I, Not I, Pml I, Pst I, Pvu I, Rsr II, Sac II, Sap I, Sau3A I, Sfl I, Sfo I, SgrA I, Sma I, SnaB I, Tsc I, Xma I, and Zra L Suitable methylation-specific restriction enzymes that do not cleave DNA at or near their recognition sequence when an adenosine within the recognition sequence is methylated at position N6 include, e.g., Mho I.

As discussed, control nucleic acids are nucleic acids that include methylation-specific cleavage sites in the recognized methylation state (e.g. always a substrate for enzymatic reaction). In the embodiments described herein, the control nucleic acids may include synthesized molecules, or purified control molecules. As one skilled in the art would appreciate, any nucleic acid molecule with a MSRE cleavage site can be used with its associated MSRE. In some embodiments, the cleavage site of the control nucleic acid is not methylated, such that the appropriate MSRE enzymatically reacts with all of the known control nucleic acid in the sample. This indicates that the enzymatic reaction is complete. If any of the control nucleic acid in the nucleic acid is not enzymatically reacted, unreacted control nucleic acid molecules are detected and quantified. The number of unreacted control nucleic acid molecules are then compared known amount of control nucleic acid molecules introduced to the sample prior to enzymatic reaction. The ratio of unreacted control molecules to the known amount of control molecules can be used as a measure of the efficiency or completeness of the methylation-specific enzymatic reaction.

Droplet Formation

Methods of the invention involve forming sample droplets where some droplets contain zero template nucleic acid molecules, some droplets contain one template nucleic acid molecule, and some droplets may or may not contain multiple template nucleic acid molecules. In some embodiments, a sample is divided into compartments such that only one or fewer of either reference target, methylation-dependent target, or control target is in any one droplet. In the described embodiments, the distribution of target nucleic acid molecules within droplets obeys the Poisson distribution. However, methods for non-Poisson loading of droplets are known to those familiar with the art, and include but are not limited to active sorting of droplets, such as by laser-induced fluorescence, or by passive one-to-one loading. The description that follows assumes Poisson loading of droplets, but such description is not intended to exclude non-Poisson loading, as the invention is compatible with all distributions of DNA loading.

The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41,780) and European publication number EP2047910 to Raindance Technologies Inc. The content of each of which is incorporated by reference herein in its entirety.

Figure 2:
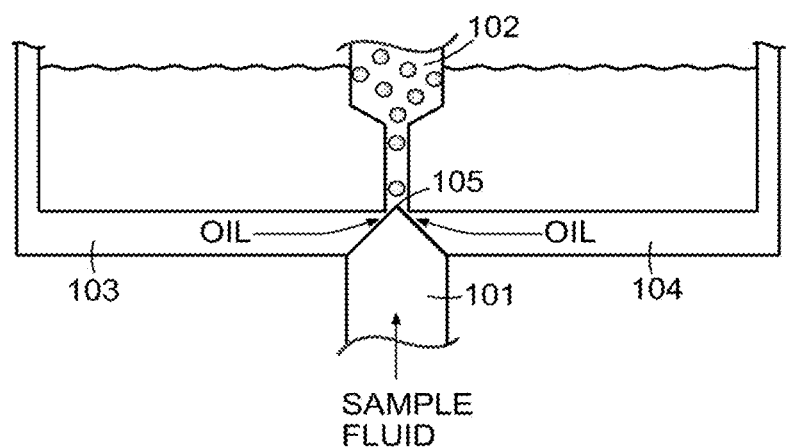
FIG. 2 depicts a portion of the droplet formation device of FIG. 1.

FIG. 1 shows an exemplary embodiment of a device 100 for droplet formation. Device 100 includes an inlet channel 101, an outlet channel 102, and two carrier fluid channels 103 and 104. Device 100 may additionally comprise a temperature block 120 to control the temperature of the fluids during droplet formation. Temperature block 120 may be used to heat or cool the fluids as needed, and may be connected to a temperature controller (not shown) to control the temperature during droplet formation. Channels 101, 102, 103, and 104 meet at a junction 105. Inlet channel 101 flows sample fluid to the junction 105. Carrier fluid channels 103 and 104 flow a carrier fluid that is immiscible with the sample fluid to the junction 105. Inlet channel 101 narrows at its distal portion wherein it connects to junction 105 (see FIG. 2). Inlet channel 101 is oriented to be perpendicular to carrier fluid channels 103 and 104. Droplets are formed as sample fluid flows from inlet channel 101 to junction 105, where the sample fluid interacts with flowing carrier fluid provided to the junction 105 by carrier fluid channels 103 and 104. Outlet channel 102 receives the droplets of sample fluid surrounded by carrier fluid.

The sample fluid is typically an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid is one that is immiscible with the sample fluid. The carrier fluid can be a non-polar solvent, decane (e g., tetradecane or hexadecane), fluorocarbon oil, silicone oil or another oil (for example, mineral oil).

In certain embodiments, the carrier fluid contains one or more additives, such as agents which increase, reduce, or otherwise create non-Newtonian surface tensions (surfactants) and/or stabilize droplets against spontaneous coalescence on contact. Surfactants can include Tween, Span, fluorosurfactants, and other agents that are soluble in oil relative to water. In some applications, performance is improved by adding a second surfactant, or other agent, such as a polymer or other additive, to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be coated with a surfactant or a mixture of surfactants. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglycerl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perflourinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., FLUORINERT (3M)), which then serves as the carrier fluid.

One approach to merging sample fluids, using a device called a lambda injector, involves forming a droplet, and contacting the droplet with a fluid stream, in which a portion of the fluid stream integrates with the droplet to form a mixed droplet. In this approach, only one phase needs to reach a merge area in a form of a droplet. Further description of such method is shown in pending U.S. patent application Ser. No. 13/371,222, the content of which is incorporated y reference herein in its entirety.

According to a method for operating the lambda injector, a droplet is formed as described above. After formation of the sample droplet from the first sample fluid, the droplet is contacted with a flow of a second sample fluid stream. Contact between the droplet and the fluid stream results in a portion of the fluid stream integrating with the droplet to form a mixed droplet.

The droplets of the first sample fluid flow through a first channel separated from each other by immiscible carrier fluid and suspended in the immiscible carrier fluid. The droplets are delivered to the merge area, i.e., junction of the first channel with the second channel, by a pressure-driven flow generated by a positive displacement pump. While droplet arrives at the merge area, a bolus of a second sample fluid is protruding from an opening of the second channel into the first channel. Preferably, the channels are oriented perpendicular to each other. However, any angle that results in an intersection of the channels may be used.

The bolus of the second sample fluid stream continues to increase in size due to pumping action of a positive displacement pump connected to channel, which outputs a steady stream of the second sample fluid into the merge area. The flowing droplet containing the first sample fluid eventually contacts the bolus of the second sample fluid that is protruding into the first channel. Contact between the two sample fluids results in a portion of the second sample fluid being segmented from the second sample fluid stream and joining with the first sample fluid droplet to form a mixed droplet. In certain embodiments, each incoming droplet of first sample fluid is merged with the same amount of second sample fluid.

In certain embodiments, an electric charge is applied to the first and second sample fluids. Description of applying electric charge to sample fluids is provided in Link et al. (U.S. patent application number 2007/0003442) and European Patent Number EP2004316 to Raindance Technologies Inc, the content of each of which is incorporated by reference herein in its entirety. Electric charge may be created in the first and second sample fluids within the carrier fluid using any suitable technique, for example, by placing the first and second sample fluids within an electric field (which may be AC, DC, etc.), and/or causing a reaction to occur that causes the first and second sample fluids to have an electric charge, for example, a chemical reaction, an ionic reaction, a photocatalyzed reaction, etc.

The electric field, in some embodiments, is generated from an electric field generator, i.e., a device or system able to create an electric field that can be applied to the fluid. The electric field generator may produce an AC field (i.e., one that varies periodically with respect to time, for example, sinusoidally, sawtooth, square, etc.), a DC field (i.e., one that is constant with respect to time), a pulsed field, etc. The electric field generator may be constructed and arranged to create an electric field within a fluid contained within a channel or a microfluidic channel. The electric field generator may be integral to or separate from the fluidic system containing the channel or microfluidic channel, according to some embodiments.

Techniques for producing a suitable electric field (which may be AC, DC, etc.) are known to those of ordinary skill in the art. For example, in one embodiment, an electric field is produced by applying voltage across a pair of electrodes, which may be positioned on or embedded within the fluidic system (for example, within a substrate defining the channel or microfluidic channel), and/or positioned proximate the fluid such that at least a portion of the electric field interacts with the fluid. The electrodes can be fashioned from any suitable electrode material or materials known to those of ordinary skill in the art, including, but not limited to, silver, gold, copper, carbon, platinum, copper, tungsten, tin, cadmium, nickel, indium tin oxide ("ITO"), etc., as well as combinations thereof. In some cases, transparent or substantially transparent electrodes can be used.

The electric field facilitates rupture of the interface separating the second sample fluid and the droplet. Rupturing the interface facilitates merging of bolus of the second sample fluid and the first sample fluid droplet. The forming mixed droplet continues to increase in size until it a portion of the second sample fluid breaks free or segments from the second sample fluid stream prior to arrival and merging of the next droplet containing the first sample fluid. The segmenting of the portion of the second sample fluid from the second sample fluid stream occurs as soon as the shear force exerted on the forming mixed droplet by the immiscible carrier fluid overcomes the surface tension whose action is to keep the segmenting portion of the second sample fluid connected with the second sample fluid stream. The now fully formed mixed droplet continues to flow through the first channel.

In other embodiments, the rupture of the interface can be spontaneous, or the rupture can be facilitated by surface chemistry. The invention is not limited in regard to the method of rupture at the interface, as rupture can be brought about by any means.

In the context of PCR, in a preferred embodiment, the first sample fluid contains template molecules of methylation state specific targets, reference targets, and control nucleic acid. The first sample fluid contains the template molecules of methylation state specific target nucleic acid, reference target nucleic acid, and control nucleic acid after methylation state specific enzymatic reaction. The methylation state specific enzymatic reaction is designed to cleave corresponding un-methylated sites of the methylation state specific target nucleic acid, and the methylation state specific enzymatic reaction of the control nucleic acid acts a measure of enzymatic reaction efficiency as discussed previously. The control nucleic acid can be added manually to the first sample fluid or introduced automatically by, for example, merging another fluid stream with the control nucleic acid templates into the first fluid stream. Droplets of the first sample fluid are formed as described above. Those droplets will include template molecules of methylation state specific targets, reference targets, and control nucleic acid molecules. In certain embodiments, some of the droplets will include only a single methylation state specific target molecule, reference target molecule, or control nucleic acid template while other droplets contain no template molecule, and thus digital PCR can be conducted. In a preferred embodiment, the droplets are formed in the presence of reagents and enzymes needed for subsequent PCR reactions. In other embodiments, a second sample fluid contains reagents for the PCR reaction. Such reagents generally include Taq polymerase, deoxynucleotides of type A, C, G and T, magnesium chloride, and forward and (optionally) reverse primers, all suspended within an aqueous buffer. The second fluid also includes detectably labeled probes for detection of the amplified methylation-dependent target, reference target, and control nucleic acid molecule. In an embodiment in which the PCR reagents are in a separate droplet, a droplet containing the nucleic acid is caused to merge with the PCR reagents in the second fluid as described above, producing a droplet that includes Taq polymerase, deoxynucleotides of type A, C, G and T, magnesium chloride, forward and reverse primers, detectably labeled probes, and the target nucleic acid. In another embodiment, the first fluid can contain the template DNA and PCR master mix (defined below), and the second fluid can contain the forward and reverse primers and the probe. The invention is not restricted in any way regarding the constituency of the first and second fluidics for PCR or digital PCR. For example, in some embodiments, the template DNA is contained in the second fluid inside droplets.

Target Amplification

Methods of the invention further involve amplifying the target nucleic acid in each droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. Primer sets introduced to the droplets can include primers specific to reference target, one or more different methylation-dependent targets (e.g. target methylation-dependent CpG regions), and control nucleic acid molecules (e.g. specific to the cleavage site of the control nucleic acid molecules).

To effect amplification, primers are annealed to their complementary sequence within the target molecule. Following annealing, the primers are extended with a polymerase so as to form a new complementary strand. The steps of denaturation, primer annealing and polymerase extension can be repeated many times (i.e., denaturation, annealing and extension constitute one cycle; there can be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The sample droplet may be pre-mixed with a primer or primers, or the primer or primers may be added to the droplet. In some embodiments, droplets created by segmenting the starting sample are merged with a second set of droplets including one or more primers for the target nucleic acid in order to produce final droplets. The merging of droplets can be accomplished using, for example, one or more droplet merging techniques described for example in Link et al. (U.S. patent application numbers 2008/0014589, 2008/0003142, and 2010/0137163) and European publication number EP2047910 to Raindance Technologies Inc.

In embodiments involving merging of droplets, two droplet formation modules are used. In one embodiment, a first droplet formation module produces the sample droplets consistent with limiting or terminal dilution of reference target nucleic acid, methylation-dependent nucleic acid, and control nucleic acid. A second droplet formation or reinjection module inserts droplets that contain reagents for a PCR reaction. Such droplets generally include the "PCR master mix" (known to those in the art as a mixture containing at least Taq polymerase, deoxynucleotides of type A, C, G and T, and magnesium chloride) and forward and reverse primers (known to those in the art collectively as "primers"), all suspended within an aqueous buffer. The second droplet also includes detectably labeled probes for detection of the amplified target nucleic acids (whether the reference targets, control, methylation-dependent target), the details of which are discussed below. Different arrangements of reagents between the two droplet types is envisioned. For example, in another embodiment, the template droplets also contain the PCR master mix, but the primers and probes remain in the second droplets. Any arrangement of reagents and template DNA can be used according to the invention.

Primers can be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers can also be obtained from commercial sources such as Operon Technologies, Amersham Pharmacia Biotech, Sigma, and Life Technologies. The primers can have an identical melting temperature. The lengths of the primers can be extended or shortened at the 5' end or the 3' end to produce primers with desired melting temperatures. Also, the annealing position of each primer pair can be designed such that the sequence and, length of the primer pairs yield the desired melting temperature. The simplest equation for determining the melting temperature of primers smaller than 25 base pairs is the Wallace Rule (Td=2(A+T)+4(G+C)). Another method for determining the melting temperature of primers is the nearest neighbor method Computer programs can also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The $T_M$ (melting or annealing temperature) of each primer is calculated using software programs such as Oligo Design, available from Invitrogen Corp.

In one embodiment, the droplet formation modules are arranged and controlled to produce an interdigitation of sample droplets and PCR reagent droplets flowing through a channel. Such an arrangement is described for example in Link et al. (U.S. patent application numbers 2008/0014589, 2008/0003142, and 2010/0137163) and European publication number EP2047910 to Raindance Technologies Inc.

A sample droplet is then caused to merge with a PCR reagent droplet, producing a droplet that includes the PCR master mix, primers, detectably labeled probes, and the target nucleic acid. Droplets may be merged for example by: producing dielectrophoretic forces on the droplets using electric field gradients and then controlling the forces to cause the droplets to merge; producing droplets of different sizes that thus travel at different velocities, which causes the droplets to merge; and producing droplets having different viscosities that thus travel at different velocities, which causes the droplets to merge with each other. Each of those techniques is further described in Link et al. (U.S. patent application numbers 2008/0014589, 2008/0003142, and 2010/0137163) and European publication number EP2047910 to Raindance Technologies Inc. Further description of producing and controlling dielectrophoretic forces on droplets to cause the droplets to merge is described in Link et al. (U.S. patent application number 2007/0003442) and European Patent Number EP2004316 to Raindance Technologies Inc.

In another embodiment, called simple droplet generation, a single droplet formation module, or a plurality of droplet formation modules are arranged to produce droplets from a mixture already containing the template DNA, the PCR master mix, primers, and detectably labeled probes. In yet another embodiment, called co-flow, upstream from a single droplet formation module two channels intersect allowing two flow streams to converge. One flow stream contains one set of reagents and the template DNA, and the other contains the remaining reagents. In the preferred embodiment for co-flow, the template DNA and the PCR master mix are in one flow stream, and the primers and probes are in the other. However, the invention is not limited in regard to the constituency of either flow stream. For example, in another embodiment, one flow stream contains just the template DNA, and the other contains the PCR master mix, the primers, and the probes. On convergence of the flow streams in a fluidic intersection, the flow streams may or may not mix before the droplet generation nozzle. In either embodiment, some amount of fluid from the first stream, and some amount of fluid from the second stream are encapsulated within a single droplet. Following encapsulation, complete mixing occurs.

Once final droplets have been produced by any of the droplet forming embodiments above, or by any other embodiments, the droplets are thermal cycled, resulting in amplification of the target nucleic acid in each droplet. In certain embodiments, the droplets are collected off-chip as an emulsion in a PCR thermal cycling tube and then thermally cycled in a conventional thermal cycler. Temperature profiles for thermal cycling can be adjusted and optimized as with any conventional DNA amplification by PCR.

In certain embodiments, the droplets are flowed through a channel in a serpentine path between heating and cooling lines to amplify the nucleic acid in the droplet. The width and depth of the channel may be adjusted to set the residence time at each temperature, which can be controlled to anywhere between less than a second and minutes.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, $3^{rd}$ edition, Cold Spring Harbor Laboratory Press, Cold Spring Harbor, New York, 2001).

In certain embodiments, the three temperature zones are controlled to have temperatures as follows: 95° C. ($T_H$), 55° C. ($T_L$), 72° C. ($T_M$). The prepared sample droplets flow through the channel at a controlled rate. The sample droplets first pass the initial denaturation zone ($T_H$) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme. Methods for controlling the temperature in each zone may include but are not limited to electrical resistance, Peltier junction, microwave radiation, and illumination with infrared radiation.

The nucleic acids undergo the same thermal cycling and chemical reaction as the droplets passes through each thermal cycle as they flow through the channel. The total number of cycles in the device is easily altered by an extension of thermal zones or by the creation of a continuous loop structure. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. ($T_H$) and 60° C. ($T_L$). The sample droplet optionally flows through an initial preheat zone before entering thermal cycling. The preheat zone may be important for some chemistry for activation and also to ensure that double stranded nucleic acid in the droplets are fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

In another embodiment the droplets are created and/or merged on chip followed by their storage either on the same chip or another chip or off chip in some type of storage vessel such as a PCR tube. The chip or storage vessel containing the droplets is then cycled in its entirety to achieve the desired PCR heating and cooling cycles.

In another embodiment the droplets are collected in a chamber where the density difference between the droplets and the surrounding oil allows for the oil to be rapidly exchanged without removing the droplets. The temperature of the droplets can then be rapidly changed by exchange of the oil in the vessel for oil of a different temperature. This technique is broadly useful with two and three step temperature cycling or any other sequence of temperatures.

The invention is not limited by the method used to thermocycle the droplets. Any method of thermocycling the droplets may be used.

Target Detection

After amplification, droplets are flowed to a detection module for detection of amplification products. For embodiments in which the droplets are thermally cycled off-chip, the droplets require re-injection into either a second fluidic circuit for read-out—that may or may not reside on the same chip as the fluidic circuit or circuits for droplet generation— or in certain embodiments the droplets may be reinjected for read-out back into the original fluidic circuit used for droplet generation. The droplets may be individually analyzed and detected using any methods known in the art, such as detecting the presence or amount of a reporter. Generally, the detection module is in communication with one or more detection apparatuses. The detection apparatuses can be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In certain embodiments, amplified target (control, one or more different reference targets, and one or more different methylation-dependent targets) are detected using detectably labeled probes. In particular embodiments, the detectably labeled probes are optically labeled probes, such as fluorescently labeled probes. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'S"-dibromopyrogallol-sulfonaphthalein (Bromopyrogallol Red); 7-diethylamino-3-(4'-isothiocyanatophenyl)-4-methylcoumarin;

diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are FAM and VIC™ (from Applied Biosystems). Labels other than fluorescent labels are contemplated by the invention, including other optically-detectable labels.

In certain aspects, the droplets of the invention contain a plurality of detectable probes that hybridize to amplicons produced in the droplets. Members of the plurality of probes can each include the same detectable label, or a different detectable label. The plurality of probes can also include one or more groups of probes at varying concentration. The groups of probes at varying concentrations can include the same detectable label which vary in intensity, due to varying probe concentrations.

In some embodiments, the droplets of the invention contain a plurality of barcodes that hybridize to amplicons produced in the droplets or are incorporated into the amplicons. The barcodes may be used in lieu of fluorescent probes, to detect the presence of a target sequence, or the barcodes can be used in addition to fluorescent probes, to track a multitude of sample sources. A detectable barcode-type label can be any barcode-type label known in the art including, for example, barcoded magnetic beads (e.g., from Applied Biocode, Inc., Santa Fe Springs, CA), and nucleic acid sequences. Nucleic acid barcode sequences typically include a set of oligonucleotides ranging from about 4 to about 20 oligonucleotide bases (e.g., 8-10 oligonucleotide bases) and uniquely encode a discrete library member without containing significant homology to any sequence in the targeted sample.

The barcode sequence generally includes features useful in sequencing reactions. For example, the barcode sequences are designed to have minimal or no homopolymer regions, i.e., 2 or more of the same base in a row such as AA or CCC, within the barcode sequence. The barcode sequences are also designed so that they are at least one edit distance away from the base addition order when performing base-by-base sequencing, ensuring that the first and last base do not match the expected bases of the sequence. In certain embodiments, the barcode sequences are designed to be correlated to a particular subject, allowing subject samples to be distinguished. Designing barcodes is shown U.S. Pat. No. 6,235,475, the contents of which are incorporated by reference herein in their entirety.

In some instances, the primers used in the invention may include barcodes such that the barcodes will be incorporated into the amplified products. For example, the unique barcode sequence could be incorporated into the 5' end of the primer, or the barcode sequence could be incorporated into the 3' end of the primer. In some embodiments, the barcodes may be incorporated into the amplified products after amplification. For example, a suitable restriction enzyme (or other endonuclease) may be introduced to a sample, e.g., a droplet, where it will cut off an end of an amplification product so that a barcode can be added with a ligase. Attaching barcode sequences to nucleic acids is shown in U.S. Pub. 2008/0081330 and WO/2010/056728 A1, the content of each of which is incorporated by reference herein in its entirety. Methods for designing sets of barcode sequences and other methods for attaching barcode sequences are shown in U.S. Pat. Nos. 6,138,077; 6,352,828; 5,636,400; 6,172,214; 6,235,475; 7,393,665; 7,544,473; 5,846,719; 5,695,934; 5,604,097; 6,150,516; RE39,793; 7,537,897; 6172,218; and 5,863,722, the content of each of which is incorporated by reference herein in its entirety. For sequencing detection, the amplified contents of the droplets may be released for multiplex sequencing.

In a separate embodiment the detection can occur by the scanning of droplets confined to a monolayer in a storage device that is transparent to the wavelengths or method or detection. Droplets stored in this fashion can be scanned either by the movement of the storage device by the scanner or the movement of the scanner over the storage device.

The invention is not limited to the TaqMan assay, as described above, but rather the invention encompasses the use of all fluorogenic DNA hybridization probes, such as molecular beacons, Solaris probes, scorpion probes, and any other probes that function by sequence specific recognition of target DNA by hybridization and result in increased fluorescence on amplification of the target sequence.

Normalization

According to methods of the invention, the quantification of methylation-dependent targets in the assay can be normalized based on the efficiency of the methylation state specific enzymatic reaction. For example, the quantified results of the assay are normalized, after detection, based on a number of unreacted control molecules that had been spiked-in at a known number of molecules per µl of sample and are remain in the sample relative to the number of control molecules introduced into the sample (i.e. measured efficiency/completeness of the enzymatic reaction). In certain embodiments, a number of the detected methylation state specific targets are normalized based on the measured efficiency. In certain embodiments, a ratio of the detected methylation-dependent targets to the reference targets is determined, and then the ratio is normalized based on the measured efficiency.

Digital PCR Performance in Droplets

Figure 3A:
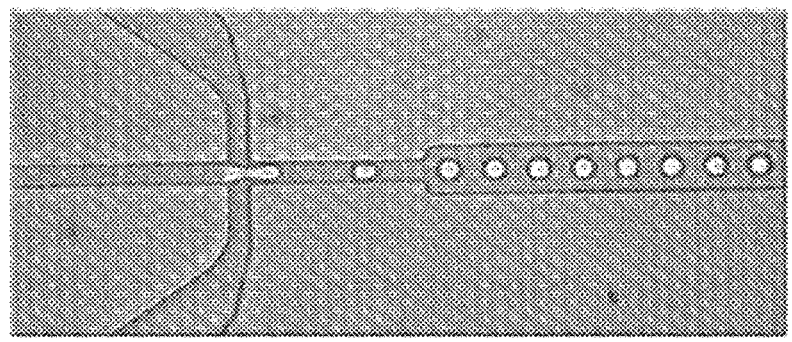
FIGS. 3A-3C depict an exemplary microfluidic system for droplet generation and readout.
Figure 3B:
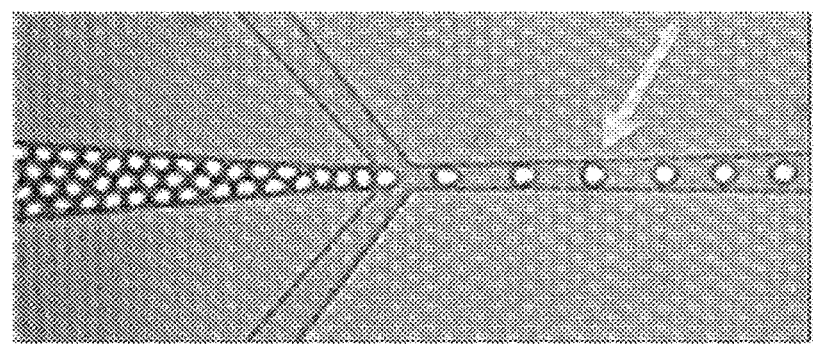
Figure 3C:
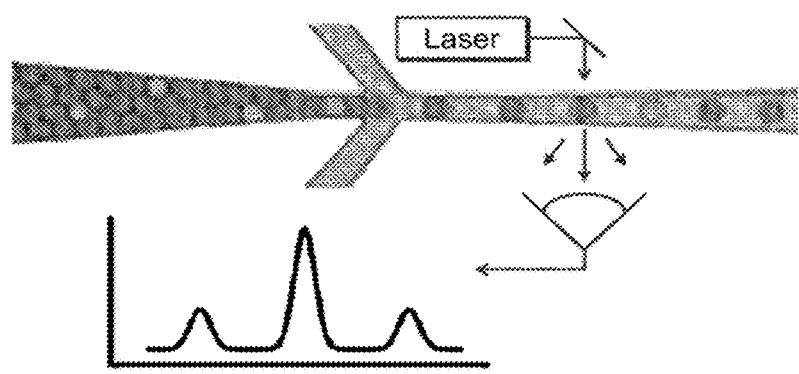

An exemplary microfluidic system for droplet generation and readout is depicted in FIG. 3. The microfluidic system is capable of both droplet generation and readout. As shown in FIG. 3A (droplet generation chip), a continuous aqueous phase containing the PCR master mix, primers, and probes, and template DNA flows into the fluidic intersection from the left, and the carrier oil enters from the top and bottom. An emerging bolus of aqueous liquid is imaged inside the intersection just prior to snapping off into a discrete 4 pL droplet as the fluidic strain begins to exceed the surface tension of the aqueous liquid. The steady train of droplets leaving the intersection toward the right is collected off chip as a stable emulsion for thermal cycling. FIG. 3B depicts the droplet spacing for readout. Flows are arranged as in 3A, except instead of a continuous phase, the emulsion from (A) is injected from the left into the intersection after thermal cycling. The oil is drained from the emulsion during off-chip handling, hence the emulsion appears tightly packed in the image before the intersection. The oil introduced in the intersection separates the droplets and the fluorescence of each droplet is measured at the location marked by the arrow. FIG. 3C depicts a cartoon of droplet readout by fluorescence. The relatively infrequent PCR(+) droplets (light gray) flow along with the majority of PCR(−) droplets (dark gray) toward the detector. The droplets are interrogated sequentially by laser induced fluorescence while passing through the detection region.

In a serial dilution, the average number of target DNA molecules per droplet—called the "occupancy" from this point forward—decreases in direct proportion to the DNA concentration. The occupancy is calculated from Poisson statistics using the following equation well known to those experienced in the art:

$$\text{occupancy} = \ln\left(\frac{P+N}{N}\right), \quad (1)$$

where P and N are the numbers of PCR(+) and PCR(−) droplets respectively.

Figure 4A:
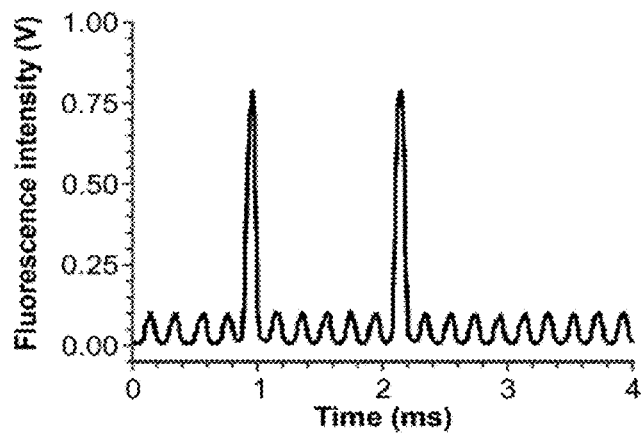
FIGS. 4A-4C depict the serial dilution of template DNA quantified by dPCR.
Figure 4B:
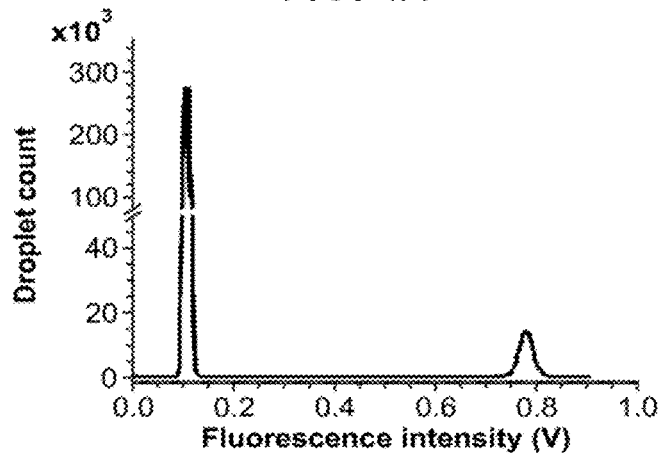
Figure 4C:
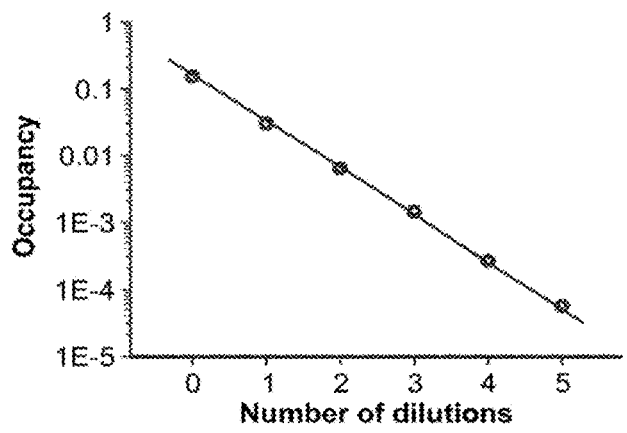
Figure 5A:
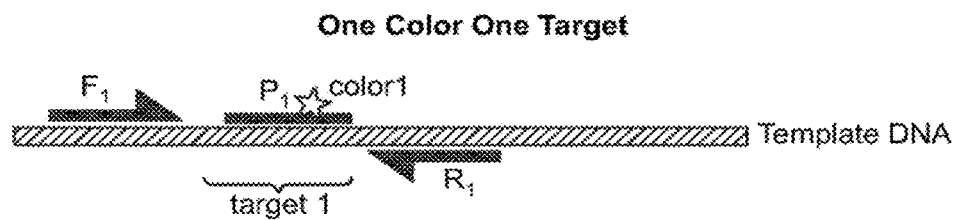
FIGS. 5A-5E are a series of schematic depicting one-color detection of a genetic sequence with a microfluidic device.
Figure 5B:
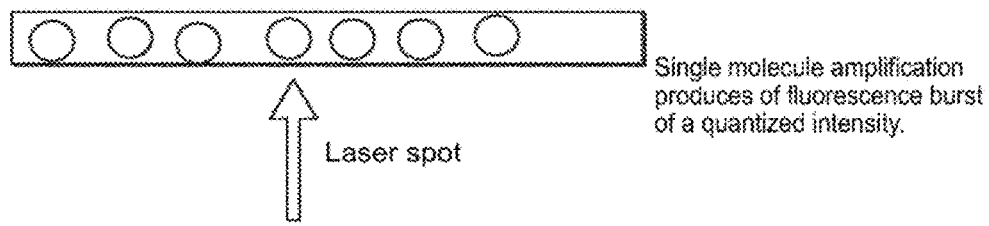
Figure 5C:
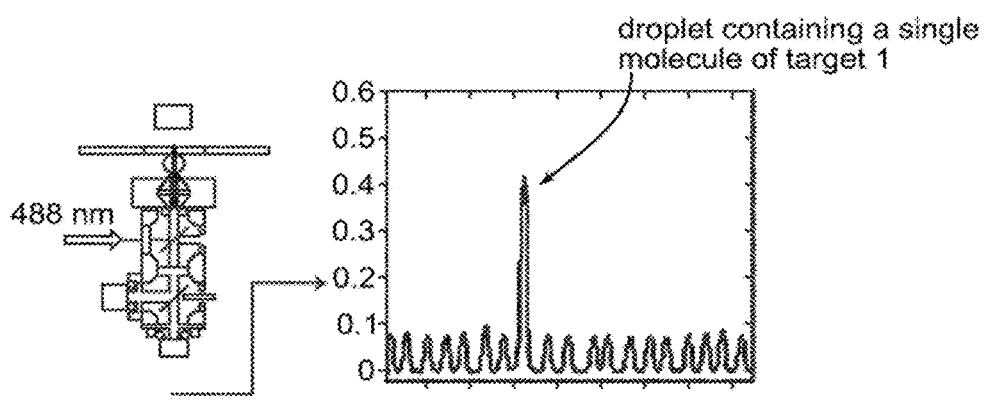
Figure 5D:
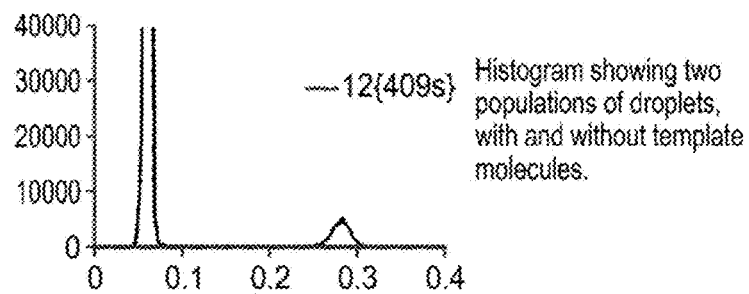
Figure 5E:
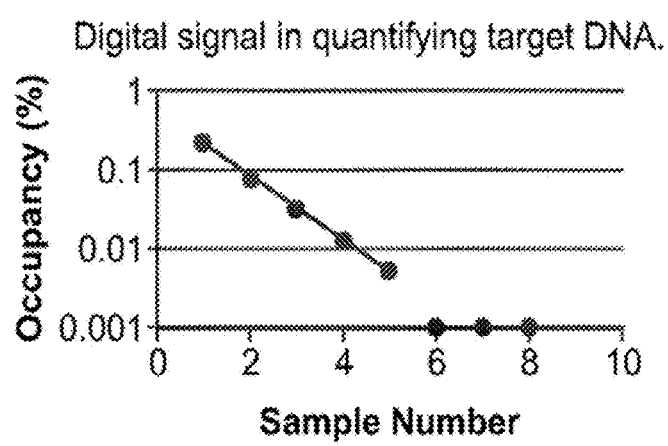

Droplets are analyzed by fluorescence while flowing through the readout chip to count the numbers of PCR(+) and PCR(−) droplets (see FIG. 3C). As each droplet passes the detection zone (marked with an arrow in FIG. 3B), a burst of fluorescence is observed. To account for small run-to-run differences in the fluorescence intensity that can occur due to different chip positioning, etc., each set of data is scaled such that the average fluorescence intensity of the empty droplets is 0.1 V. FIG. 4A shows a very short duration of a typical trace of fluorescence bursts from individual droplets for the sample with the highest DNA concentration in the series. PCR(+) and PCR(−) droplets are easily discriminated by fluorescence intensity. The two large bursts of fluorescence peaking at ~0.8 V arise from the PCR(+) droplets, whereas smaller bursts, due to incomplete fluorescence quenching in the PCR(−) droplets, peak at ~0.1 V. A histogram of peak intensities from the complete data set reveals two clear populations centered at 0.10 and 0.78 V (FIG. 4B), demonstrating that the trend evident in the short trace in FIG. 4A is stable over much longer periods of time. Integration over the two populations in FIG. 4B yields a total of 197,507 PCR(+) and 1,240,126 PCR(−) droplets. Hence the occupancy was 0.15 for this sample by Eqn. 1, corresponding to the expected occupancy of 0.18 based on the measured DNA concentration of 110 ng/µL. The occupancy is measured for each sample in the serial dilution and fit to the dilution equation:

$$\text{occupancy}(n) = \frac{A}{f^n}, \quad (2)$$

where n is the number of dilutions, A is the occupancy at the starting concentration (n=0), and f is the dilution factor. The linear fit was in excellent agreement with the data, with an $R^2$ value of 0.9999 and the fitted dilution factor of 4.8 in close agreement with the expected value of 5.0.

Copy Number Assay

Traditional digital PCR methods involve the use of a single labeled probe specific for an individual target. FIG. 5 is a schematic depicting one-color detection of a target dsDNA sequence using droplet based digital PCR. As shown in Panel A of FIG. 5, a template DNA is amplified with a forward primer (F1) and a reverse primer (R1). Probe (P1) labeled with a fluorophore of color 1 binds to the target genetic sequence (target 1). Microdroplets are made of diluted solution of template DNA under conditions of limiting or terminal dilution. Droplets containing the target sequence emit fluorescence and are detected by laser (Panels B and C). The number of microcapsules either containing or not containing the target sequence is shown in a histogram (D) and quantified (E).

Data Analysis

Analysis is then performed on the droplets. The analysis may be based on counting, i.e., i.e., determining a number of droplets containing a methylation-independent target, determining a number of droplets containing a methylated-dependent target. In some embodiments the first and second numbers are analyzed to determine whether a statistical difference exists, in other embodiments the first and second numbers are analyzed to determine a ratio with different values for the numerator/denominator compared to that expected in a 'normal' sample.

It will be appreciated that various counting schemes useful with embodiments of the invention can include: 1) ratios of targets located on the same contiguous molecule (e.g. chromosome, or chromosome segment); 2) ratio on different contiguous molecule (fetal case looks at chr21 vs. chr18 vs. 'normal diploid' chromosome); 3) ratios between 'control' targets for multiple measurements of enzymatic specificity or completion and additional input target metrics. 4) Imbalances measure amplification/deletion/enrichment/depletion of the targets.

Counting methods are well known in the art. See, e.g., Lapidus et al. (U.S. Pat. Nos. 5,670,325 and 5,928,870) and Shuber et al. (U.S. Pat. Nos. 6,203,993 and 6,214,558), the content of each of which is incorporated by reference herein in its entirety. Statistical difference may be indicative of a condition. In certain embodiments, the condition is a disease such as cancer. In other embodiments, the statistical different relates to fetal aneuploidy. In other embodiments, the difference between a number of reference targets and a number of methylated-dependent targets provides for quantification of an amount of fetal nucleic acid in maternal blood.

It is important to note that for the result to be highly quantitative, the "methylation-specific" target(s) should show the specific target-state with a high degree of penetrance. For example, for detection of fetal aneuploidy, the minor 'fetal' target should be 100% methylated/unreactable state for all fetal-derived target molecules, with the maternal targets showing the complete unmethylated/reactable state (e.g. 0% methylated). It will be appreciated by those of ordinary skill in the art that appropriate validation of the targets is important, and that embodiments of the invention are useful as validation process itself (i.e. one 'validated' target can be compared to a second 'candidate' target).

Numerous examples of methylated genes that have been linked to various types of cancer have been identified. Examples of methylated genes that have been linked with susceptibility to or incidence of colorectal cancer include, for example, FOXE1, SOX17, SYNE1, BOLL, CABYR, EFEMP1, FBLN2, FOXL2, GNB4, GSTM3, HoxD1, Jph3, Neuralized (NEURL), PPP1R14a, TP53AP1, RAB32, APC2, GPNMB, MMP2, EVL, STARD8, PTPRD, CD109, LGR6, RET, CHD5, RNF182, ICAM5, ARMCX2, CBR1, DDX43, DMRTB1, FBLN2, HIST2H2AA, ICAM1, LY6K, NEF3, POMC, STK31, SYCP3, TCL1A, TFPI-2, TLR2, UCHL1, ZFP42, ASCL2, ATP8A2, CTAG2, EPHA4, FANCF, FOXQ1, HUS1B, JAM3, LEF1, MOV10L1, NPPB, PWWP1, RASSF5, REC8L1, SALL4, BEX1, BNIP3, CCK, CDX1, CNN3, CXX1, IRX4, MC5R, RSNL2, SMARCA3, SPON1, SYT6, TRPC3, TSPYL6, ZNF345, DKK3, ZNF655, B4GALT1, C10orf119, C10orf13, CBR1, COPS4, COVA1, CSRP1, DARS, DNAJC10, FKBP14, FN3KRP, GANAB, HUS1, KLF11, MRPL4, MYLK, NELF, NETO2, PAPSS2, RBMS2, RHOB, SECTM1, SIRT2, SIRT7, SLC35D1, SLC9A3R1, TTRAP, TUBG2, FLJ20277, MYBL2, GPR116, QSMR, PC4, SLC39A4, UBE3A, PDLIM3, UBE21, or any combination thereof.

Examples of methylated genes that have been linked with susceptibility to or incidence of prostate cancer include, for example, GSTP1, APC, PTGS2, T1G1, EDNRB, RASS1a, GSTP1, APC, PTGS2, T1G1, EDNRB, CD3D, APOC1, NBL1, ING4, LEF1, CENTD3, MGC15396, FKBP4, PLTP, TFAP2A, ATXN1, BMP2, ENPEP, MCAM, SSBP2, PDLIM3, NDP, or any combination thereof.

Examples of methylated genes that have been linked with susceptibility to or incidence of breast cancer include, for example, PITX2, PITX2, BACH1, CKMT, GALE, HMG20B, KRT14, OGDHL, PON2, SESN1, KIF1A (kinesin family member 1A) PDLIM3, MAL (T cell proliferation protein), or any combination thereof.

Examples of methylated genes that have been linked with susceptibility to or incidence of lung cancer include, for example, p16INK4a, APC, TMS1, RASSF1, DAPK, PRSS3 (serine protease family member-trypsinogen IV—a putative tumor suppressor gene), human DAB2 interactive protein gene, apoptosis-associated speck-lick protein containing a CARD, p16, FHIT, H-cadherin, RARβ, RARB2, PHKA2, CBR3, CAMK4, HOXB5, ZNF198, RGS4, RBM15B, PDLIM3, PAK3, PIGH, TUBB4, NISCH or any combination thereof.

Examples of methylated markers that have been shown to be associated with susceptibility to or incidence of gastrointestinal cancer include, without limitation, NDRG4/NDRG2 subfamily gene, GATA4, OSMR, GATA5, SFRP1, ADAM23, JPH3, SFRP2, APC, MGMT, TFPI2, BNIP3, FOXE1, SYNE1, SOX17, PHACTR3, JAM3, or any combination thereof.

Examples of methylated genes that have been linked with susceptibility to or incidence of cervical cancer include, for example, ESR1, DAP-kinase, APC, TIMP-3, RAR-beta, CALCA, TSLC1, TIMP-2, DcR1, DcR2, BRCA1, p15, Rassf1A, MLH1, MGMT, PDCD4, TFPI2, ARMC7, TRM-HUMAN, OGDHL, PTGS2, CDK6, GPR39, HMGN2, C130RF18, ASMTL, DLL4, NP-659450.1, NP-078820.1, CLU, HPCA, PLCG2, RALY, GNB4, CCNA1, NPTX1, C90RF19, or any combination thereof.

Examples of "methylation-specific" genes that have been linked with fetal conditions include RASSF1/MASPIN/others. It will also be appreciated that un-methylated markers are also useful with embodiments of the invention.

Release of Target from Droplet

Methods of the invention may further involve releasing amplified target molecules from the droplets for further analysis. Methods of releasing amplified target molecules from the droplets are shown in for example in Link et al. (U.S. patent application numbers 2008/0014589, 2008/0003142, and 2010/0137163) and European publication number EP2047910 to RainDance Technologies Inc.

In certain embodiments, sample droplets are allowed to cream to the top of the carrier fluid. By way of non-limiting example, the carrier fluid can include a perfluorocarbon oil that can have one or more stabilizing surfactants. The droplet rises to the top or separates from the carrier fluid by virtue of the density of the carrier fluid being greater than that of the aqueous phase that makes up the droplet. For example, the perfluorocarbon oil used in one embodiment of the methods of the invention is 1.8, compared to the density of the aqueous phase of the droplet, which is 1.0.

The creamed liquids are then placed onto a second carrier fluid which contains a de-stabilizing surfactant, such as a perfluorinated alcohol (e.g. 1H,1H,2H,2H-Perfluoro-1-octanol). The second carrier fluid can also be a perfluorocarbon oil. Upon mixing, the aqueous droplets begins to coalesce, and coalescence is completed by brief centrifugation at low speed (e.g., 1 minute at 2000 rpm in a microcentrifuge). The coalesced aqueous phase can now be removed and the further analyzed.

The released amplified material can also be subjected to further amplification by the use tailed primers and secondary PCR primers. In this embodiment the primers in the droplet contain an additional sequence or tail added onto the 5' end of the sequence specific portion of the primer. The sequences for the tailed regions are the same for each primer pair and are incorporated onto the 5' portion of the amplicons during PCR cycling. Once the amplicons are removed from the droplets, another set of PCR primers that can hybridize to the tail regions of the amplicons can be used to amplify the products through additional rounds of PCR. The secondary primers can exactly match the tailed region in length and sequence or can themselves contain additional sequence at the 5' ends of the tail portion of the primer. During the secondary PCR cycling these additional regions also become incorporated into the amplicons. These additional sequences can include, but are not limited to adaptor regions utilized by sequencing platforms for library preparation and sequencing, sequences used as a barcoding function for the identification of samples multiplexed into the same reaction. molecules for the separation of amplicons from the rest of the reaction materials such as biotin, digoxin, peptides, or antibodies and molecules such as fluorescent markers that can be used to identify the fragments.

In certain embodiments, the amplified target molecules are sequenced. In a particular embodiment, the sequencing is single-molecule sequencing-by-synthesis. Single-molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety.

Briefly, a single-stranded nucleic acid (e.g., DNA or cDNA) is hybridized to oligonucleotides attached to a surface of a flow cell. The single-stranded nucleic acids may be captured by methods known in the art, such as those shown in Lapidus (U.S. Pat. No. 7,666,593). The oligonucleotides may be covalently attached to the surface or various attachments other than covalent linking as known to those of ordinary skill in the art may be employed. Moreover, the attachment may be indirect, e.g., via the polymerases of the invention directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Quantification of Fetal Nucleic Acid

Methods of the invention are useful for quantifying fetal nucleic acid in maternal blood in order to perform non-invasive tests for fetal genomic abnormalities. Such methods involve obtaining a sample, e.g., a tissue or body fluid that is suspected to include both maternal and fetal nucleic acids. Such samples may include urine, vaginal secretion, amniotic fluid, or tissue. In certain embodiments, this sample is drawn maternal blood, and circulating DNA is found in the blood plasma, rather than in cells. A preferred sample is maternal peripheral venous blood.

Because the amount of fetal nucleic acid in a maternal sample generally increases as a pregnancy progresses, less sample may be required as the pregnancy progresses in order to obtain the same or similar amount of fetal nucleic acid from a sample.

FIG. 6 illustrates expected results of a digital PCR 3-plex assay used to determine the percent of nucleic acid molecules in a sample deriving from the fetus in maternal blood. Specifically, the assay illustrates the ability to determine the percent of fetal nucleic acid when the methylation state specific target is a locus where the copy number is known (e.g. a normal diploid cell/patient typically has 2 copies of each gene) and is unlikely to exhibit copy number variation, and the methylation state in the fetus is different than the maternal methylation state that enables the calculation of a ratio between the two states (e.g. promoter of RASSF1A gene on chromosome 3).

FIG. 6 shows a typical dPCR cluster plot (VIC intensity on the y-axis; FAM intensity on the x-axis) with circular gates used to count the number of droplets containing certain content. As shown in FIG. 6, the bottom-left circular gate shows the number of droplets containing no target molecules (Negative). The top-left circular gate shows the number of droplets containing a reference target (Methylation state specific targets or MSRE enzymatic reaction-independent). The reference molecule is not a substrate for enzymatic reaction by the MSRE's and used to quantify the total number of amplifiable genome-equivalents in the sample. The bottom-right circular gate shows a number of droplets containing a methylation-enzymatic reaction-dependent target. The methylation state specific target is used to quantify the fetal-specific methylated nucleic acid in the sample. The top-right circular gate shows the number of control nucleic acid molecules remaining after enzymatic reaction. The unreacted control nucleic acid molecules are used to quantify the completion of a methylation state specific enzymatic reaction, and a known quantity of control molecules was added to the sample prior to methylation state specific enzymatic reaction. The number of unreacted control molecules compared to the known quantity of control molecules is used to measure the efficiency of the enzymatic reaction (e.g. percent efficiency). The number of methylation state specific targets is normalized based on that measured efficiency. The ratio of the adjusted number of methylation state specific target molecules to the number of reference molecules provides the percent of the sample nucleic acid that derives from the fetus.

In addition to determining the percent of sample nucleic acid that derives from the fetus, a similar 3-plex assay can be used to directly quantify and score a sample for a fetal aneuploidy if the methylation specific target is located on the aneuploid chromosome and the reference target molecule is on a diploid chromosome (e.g. where the ratio is different from 1:1). For example the percent fetal fraction (or tumor in the case of cancer) matters for the precision of the assay and may not be known a priori without performing an assay according to the embodiments described herein. Fetal aneuploidy (e.g., Down syndrome, Edward syndrome, and Patau syndrome) and other chromosomal aberrations affect 9 of 1,000 live births (Cunningham et al. in Williams Obstetrics, McGraw-Hill, New York, p. 942, 2002). Chromosomal abnormalities are generally diagnosed by karyotyping of fetal cells obtained by invasive procedures such as chorionic villus sampling or amniocentesis. Those procedures are associated with potentially significant risks to both the fetus and the mother. Noninvasive screening using maternal serum markers or ultrasound are available but have limited reliability (Fan et al., PNAS, 105(42):16266-16271, 2008).

Methods of the invention may be used to screen for fetal aneuploidy; for example, if the methylation state specific target is on a chromosome with potential trisomy (a type of aneuploidy), and the reference target is on a different chromosome that does not have trisomy. In such an example, a statistically-signification deviation from a 1:1 ratio in the number of droplets containing a methylation state specific target molecule and the number of droplets containing a reference molecule is indicative of trisomy. In such embodiment, the methylation state specific target is a target on chromosome 21 that has been validated as always and only being methylated in fetal nucleic acid, and the reference molecule is a target on a chromosome without copy number variation. In certain embodiments, the aneuploidy is trisomy of chromosome 21 (Down syndrome). In other embodiments, the aneuploidy may include trisomy of chromosomes 13 and 18.

As illustrated in FIG. 7, methods of the invention incorporate more than one methylation state specific target, reference molecule, and control nucleic acid in order to conduct multiple determinations in a single assay. As shown in FIG. 7, the typical dPCR cluster plot includes circular gates of droplets containing a first methylation state specific target molecule and droplets containing a second methylation state specific target molecule. This concept may be expanded further include multiple different methylation state specific target molecules and multiple different reference molecules. Referring back to FIG. 7, a count of droplets containing the first-methylation state specific target molecules can be used to determine a percentage fetal nucleic acid derived from the sample (as described above), and the second methylation state specific target molecules can be used to quantify and score the sample for a potential aneuploidy (as described above).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein.

What is claimed is:

1. A method of obtaining a normalized ratio between a fetal nucleic acid and a maternal reference nucleic acid in a mixture that provides a percent of the fetal nucleic acid in the mixture, the method comprising:
    preparing a mixture comprising (i) a fetal nucleic acid comprising only recognition sequences that are unmethylated and is capable of cleaving by a restriction enzyme that cleaves only the recognition sequences that are unmethylated, (ii) a maternal reference nucleic acid comprising only the recognition sequences that are methylated and is not capable of cleaving by the restriction enzyme that cleaves only the recognition sequences that are unmethylated, and (iii) a known initial amount of control nucleic acid having only the recognition sequences that are unmethylated and is capable of cleaving by the restriction enzyme that cleaves only the recognition sequences that are unmethylated;
    conducting a methylation-specific enzymatic reaction by exposing the mixture to the restriction enzyme that cleaves only the recognition sequences that are unmethylated;
    partitioning the mixture into droplets after the conducting step;
    measuring an amount of the fetal nucleic acid, an amount of the maternal reference nucleic acid, and an amount of the control nucleic acid in each of the droplets that remain intact by performing a digital polymerase chain reactions (PCR) in each of the droplets, wherein the measuring step includes the use of detectably labeled probes specifically hybridized to the fetal nucleic acid, the maternal reference nucleic acid, and the control nucleic acid;
    determining an efficiency value for the methylation-specific enzymatic reaction based on the known initial amount of the control nucleic acid and the amount of the control nucleic acid determined in the measuring step; and
    normalizing, using the efficiency value, the amount of the fetal nucleic acid and the amount of the maternal reference nucleic acid in the mixture, thereby obtaining the normalized ratio between the fetal nucleic acid and the maternal reference nucleic acid in the mixture that provides the percent of the fetal nucleic acid in the mixture.

2. The method of claim 1, wherein the maternal reference nucleic acid is not a substrate for the methylation-specific reaction.

3. The method of claim 1, wherein said measuring the amount of fetal nucleic acid includes counting a number of the droplets that include the fetal nucleic acid that remains intact after the digital PCRs and wherein said measuring the amount of control nucleic acid includes counting a number of the droplets that include the control nucleic acid that remains intact after the digital PCRs.

4. The method of claim 1, wherein each of the fetal nucleic acid, the maternal reference nucleic acid, and the control nucleic acid comprises a promoter of a RASSFIA gene.

5. The method of claim 4, further comprising detecting the amplified products in each of the droplets using fluorescent hydrolysis probes wherein the detectably labeled probes are the fluorescent hydrolysis probes.

6. The method of claim 4, wherein the droplets are surrounded by an immiscible carrier fluid.

7. The method of claim 6, wherein the immiscible carrier fluid comprises an oil.

8. The method of claim 7, wherein the oil comprises a fluorosurfactant.

* * * * *